(12) United States Patent
Nguyen-Ba et al.

(10) Patent No.: US 6,194,576 B1
(45) Date of Patent: Feb. 27, 2001

(54) PROCESS FOR PREPARING ANTIVIRAL 2-PHOSPONATE NUCLEOTIDE ANALOGS

(75) Inventors: Nghe Nguyen-Ba, La Prairie; Miguel Quimpere, Laval des Rapides; Laval Chan Chun Kong, Kirkland; William L. Brown, Laval; Gervais Dionne, St-Laurent, all of (CA)

(73) Assignee: BioChem Pharma, Inc. (CA)

( * ) Notice: Subject to any disclaimer, the term of this patent is extended or adjusted under 35 U.S.C. 154(b) by 0 days.

(21) Appl. No.: 09/411,980

(22) Filed: Oct. 4, 1999

Related U.S. Application Data

(62) Division of application No. 08/868,782, filed on Jun. 4, 1997, now Pat. No. 6,005,107, which is a division of application No. 08/868,706, filed on Jun. 4, 1997, now Pat. No. 5,955,160, which is a division of application No. 08/465,921, filed on Jun. 6, 1995, now abandoned, which is a division of application No. 08/171,527, filed on Dec. 22, 1993, now abandoned.

(30) Foreign Application Priority Data

Dec. 23, 1992 (GB) .................................................. 9226879

(51) Int. Cl.$^7$ ...................... C07D 407/04; C07D 409/06; C07D 411/12; C07D 473/40; C07D 487/04
(52) U.S. Cl. ..................... 544/195; 544/214; 544/232; 544/243; 544/244; 546/23; 546/24; 548/112; 548/113
(58) Field of Search ................................... 544/244, 243, 544/232, 214, 195; 546/24, 23; 548/112, 113

(56) References Cited

U.S. PATENT DOCUMENTS

| | | |
|---|---|---|
| 4,950,758 | 8/1990 | Vince et al. . |
| 5,118,672 | 6/1992 | Schinazi et al. . |
| 5,159,067 | 10/1992 | Schinazi et al. . |
| 5,789,394 | 8/1998 | Nguyen-Ba et al. . |

FOREIGN PATENT DOCUMENTS

| | | |
|---|---|---|
| 0 337 713 | 10/1989 | (EP) . |
| 0 382 526 | 8/1990 | (EP) . |
| 0 452 935 | 10/1991 | (EP) . |
| 0 468 866 | 1/1992 | (EP) . |
| 0 515 156 | 11/1992 | (EP) . |
| 2 230 266 | 10/1990 | (GB) . |
| WO 92/08717 | 5/1992 | (WO) . |
| 92/11269 | 7/1992 | (WO) . |

OTHER PUBLICATIONS

Paul G. Stecher et al, The Merck Index, eighth edition, 1968, Rahway, NJ.*
D. J. Brown, "The Pyrimidines", 1962, Interscience, New York, p 282.*
Katrizsky et al, Tet... 46, 1990, 641–648.*
J. H. Lister, "Purines" Wiley–Interscience, 1971, New York, 418–419.*
N. S. Girgis et al, J. Heterocyclic Chem., 24, 1987, 821–827.*
Philipp Fresenium, "Organic Chemical Nomenclature", John Wiley, New York, 1989, pp. 86–87 and 142–143.*
Bednarski et al., *Biorganic & Medicinal Chemistry Letters*, vol. 5, pp. 1741–1744 (1995).
Cabasso et al., *Journal of Applied Polymer Science*, vol. 41 pp. 3025–3042 (1990).
Aly et al., *Liebigs Ann. Chem.*, pp. 127–129 (1992).
Bronson et al., *Bioorg. Med. Chem. Lett.*, pp. 685–690 (1992).
Charvet et al., *J. Med. Chem.*, vol. 37, pp. 2216–2223 (1994).
Duke et al., *Antiviral Res.*, vol. 6, pp. 299–308 (1986).
Kim et al., *Bioorg. Med. Chem. Letters.*, vol. 2, pp. 367–370 (1992).
J. Kraus, *Nucleosides & Nucleotides*, vol. 12, pp. 157–162 (1993).
Miyasaka et al., *Chem. Abstracts*, vol. 114, No. 122988w, p. 861 (1991).
Secrist III et al., *Nucleosides & Nucleotides*, vol. 11, pp. 947–956 (1992).
Starrett, Jr. et al. *Antiviral Res.*, vol. 19, pp. 267–273 (1992).
Tanaka et al., *Tetrahedron Letters*, vol. 30, pp. 2567–2570 (1989).
Kurbanov et al., *Russian Journal of Organic Chemistry*, pp. 937–939 (1992).
Otmar et al., *Collect. Czech Chem. Commun.*, vol. 58 pp. 2159–2179 (1993).
Otmar et al., *Collect. Czech Chem. Commun.*, vol. 58, pp. 2180–2196 (1993).

* cited by examiner

*Primary Examiner*—Mukund J. Shah
(74) *Attorney, Agent, or Firm*—Millen White Zelano & Branigan

(57) ABSTRACT

Nucleotide analogues having the general formula (I) and pharmaceutically acceptable derivatives:

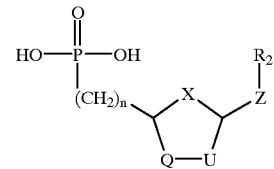

(I)

wherein n is 0 or an integer;

X is O or S, $CH_2$, CH-halogen, CH—$N_3$, or C=$CH_2$;

Q and U are independently selected from: O, S, and CH($R_a$) wherein $R_a$ is hydrogen, OH, halogen, $N_3$, $NH_2$, SH, carboxyl, $C_{1-6}$ alkyl or $R_a$ is $CH_2(R_b)$ wherein $R_b$ is hydrogen, OH, SH, $NH_2$, $C_{1-6}$ alkyl or carboxyl; or both Q and U are CH when Q and U are linked by a double bond;

Z is selected from: O, a $C_{1-6}$ alkoxy, a $C_{1-6}$ thioalkyl, a $C_{1-6}$ aminoalkyl, $(CH_2)_m$ wherein m is 0 or an integer, and $N(R_c)_2$ wherein both $R_c$ are independently hydrogen or a $C_{1-6}$ alkyl; and R2 is a purine or pyrimidine base or an analogue or derivative thereof. Members of this series of analogues possess anti-viral activity.

20 Claims, No Drawings

PROCESS FOR PREPARING ANTIVIRAL 2-PHOSPONATE NUCLEOTIDE ANALOGS

This is a divisional, of application Ser. No. 08/868,782 filed Jun. 4, 1997, now U.S. Pat. No. 6,005,107; which is a divisional of Ser. No. 08/868,706 filed Jun. 4, 1997 now U.S. Pat. No. 5,955,610 (patented); which is a divisional of Ser. No. 08/465,921 filed Jun. 6, 1995 (abandoned); which is a divisional of Ser. No. 08/171,527 filed Dec. 22, 1993 (abandoned).

The present invention relates to new nucleotide analogues. Particularly, it is concerned with the use of 2-phosphonate-nucleotide analogues in the treatment of viral infections.

Cytomegalovirus (CMV) is recognized as an important pathogen in patients with AIDS. The virus often contributes to the immunosuppression observed in such patients and may cause disseminated disease involving the lungs, gastrointestinal tract, central nervous system, or eyes. CMV retinitis is recognized as an important cause of blindness in patients with AIDS. Also, human cytomegalovirus (HCMV) infection is a major cause of death in AIDS patients. Currently, there are only two approved drugs, ganciclovir and foscarnet, for its treatment. Ganciclovir has exhibited bone marrow suppression as a serious side effect and resistant strains have also been isolated. Foscarnet presents side effects that are associated with its administration such as reversible renal dysfunction, thrombophlebitis at the infusion site, headaches and anemia. Also, foscarnet is not orally bioavailable, limiting its utility in clinical treatment. It is poorly soluble, and large doses are required because of its relatively low potency. Therefore, the development of a potent and non-toxic anti-CMV agents is highly desired.

All human herpesviruses have a worldwide distribution and are amongst the most difficult human pathogens to control. Currently, considerable efforts are being directed towards the development of vaccines and antiviral agents that will be active against herpesviruses, particularly Herpes Simplex viruses HSV-1 and HSV-2. A number of nucleoside and nucleotide derivatives are active against primary and recurrent HSV infection; of these, acyclovir is the most used drug. However, among patients with AIDS, acyclovir-resistant HSV-2 may lead to chronic progressive infections. There is therefore a need for development of a potent and non-toxic agent against HSV-1 and HSV-2.

Since their discovery in 1986, the acyclic phosphonate nucleotide analogs have generated considerable attention as broad spectrum antiviral agents. The guanine analogues HPMPG and PMEG, the adenine analogues HPMPA, and the cytosine analogue HPMPC have been shown to exhibit good anti-HCMV activity and HSV activity. PMEA has also demonstrated in vitro activity against retroviruses such as the human immunodeficiency virus (HIV), as well as DNA viruses such as herpes simplex virus (HSV), and in vivo activity against murine cytomegalovirus (CMV).

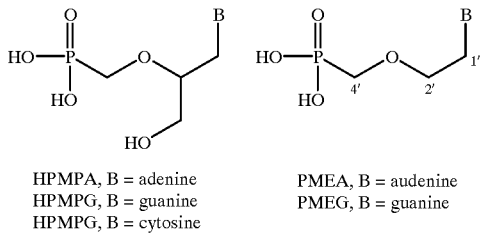

HPMPA, B = adenine
HPMPG, B = guanine
HPMPG, B = cytosine

PMEA, B = audenine
PMEG, B = guanine

Unfortunately, in general these compounds present problems in cytotoxicity, particularly, PMEG is very cytotoxic.

SUMMARY OF THE INVENTION

We have designed a novel class of 2-phosphonate-nucleotide analogues having the general formula (I), salts or esters thereof, and pharmaceutically acceptable derivatives. Members of this series of analogues possess anti-viral activity.

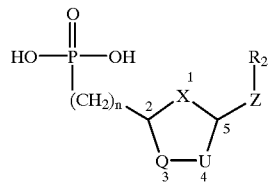

(I)

wherein n is 0 or an integer;

X is O or S, $CH_2$, CH-halogen, CH—$N_3$, or C=$CH_2$;

Q and U are independently selected from: O, S, and CH($R_a$) wherein $R_a$ is hydrogen, OH, halogen, $N_3$, $NH_2$ SH, carboxyl, $C_{1-6}$ alkyl or $R_a$ is $CH_2(R_b)$ wherein $R_b$ is hydrogen, OH, SH, $NH_2$, $C_{1-6}$ alkyl or carboxyl; or both Q and U are CH when Q and U are linked by a double bond;

Z is selected from: O, a $C_{1-6}$ alkoxy, a $C_{1-6}$ thioalkyl, a $C_{1-6}$ aminoalkyl, $(CH_2)_m$ wherein m is 0 or an integer, and $N(R_c)_2$ wherein both $R_c$ are independently hydrogen or a $C_{1-6}$ alkyl,; and R2 is a purine or pyrimidine base or an analogue or derivative thereof.

Also included within the scope of the invention are compounds of formula (I) when X, Q, or U is S, further oxidized to form SO or $SO_2$.

It will be appreciated by those of skill in the art that the compounds of formula (I) may contain several chiral centers and thus, amongst other forms, exist in the form of pairs of optical isomers (i.e. enantiomers) and mixtures thereof including racemic mixtures. Thus the compounds of formula (I) may be either cis isomers, as represented by formula (IA), or trans isomers, as represented by formula (IB), or mixtures thereof. Each of the cis and trans isomers can exist as one of two enantiomers or as mixtures thereof including racemic mixtures. All such isomers and mixtures thereof including racemic mixtures are included within the scope of the invention.

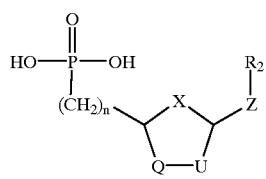
(IA)

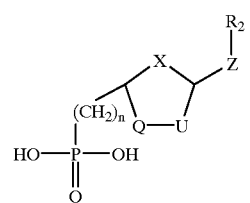
(IB)

By purine or pyrimidine base or an analogue thereof is meant a purine or pyrimidine base found in a nucleotide or an analogue thereof which mimics such bases in that their structures (the kinds of atoms and their arrangement) are similar to the normal bases but may possess additional or lack certain of the functional properties of the normal bases. Such analogues include imidazopyrimidines, iso-imidazopyrimidines, or those derived by replacement of a CH moiety by a nitrogen atom (for example, 5-azapyrimidines such as 5-azacytosine) or vice versa (for example 7-deazapurines, such as 7-deazadenosine or 7-deazaguanosine) or both (e.g. 7-deaza, 8-azapurines). By derivatives of such bases or analogues are meant those compounds wherein ring substituents are either incorporated, removed or modified by conventional substituents known in the art e.g. halogen, hydroxyl, amino, $C_{1-6}$ alkyl. Such purine or pyrimidine base, analogues and derivatives will be well known to those skilled in the art.

Conveniently, the group R2 is preferably selected from:

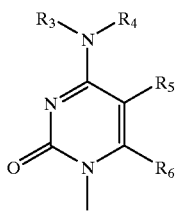
A)

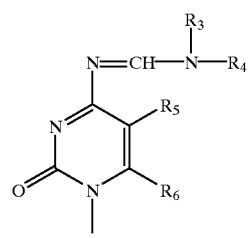
B)

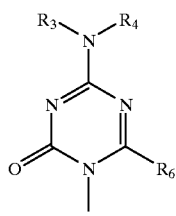
C)

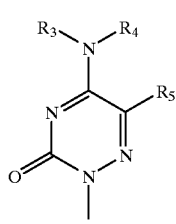
D)

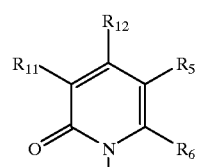
E)

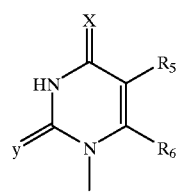
F)

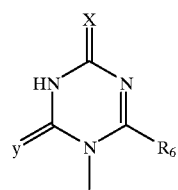
G)

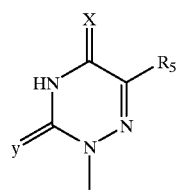
H)

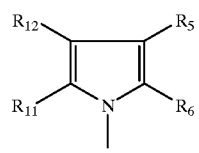
I)

wherein:

x is oxygen or sulfur;

y is oxygen or sulfur;

$R_3$ and $R_4$ are independently selected from the group consisting of hydrogen, hydroxyl, amino, $C_{1-6}$ alkyl or $C_{1-6}$ alkenyl, $C_{1-6}$ alkynyl, $C_{1-10}$ acyl, aryl or carboxyl;

$R_5$, $R_6$, $R_{11}$, and $R_{12}$ are each independently selected from the group consisting of hydrogen, halogen, hydroxyl, amino, cyano, carboxy, carbamoyl, alkoxycarbonyl, hydroxymethyl, trifluoromethyl, thioaryl, $C_{1-6}$ alkyl, $C_{1-6}$ alkenyl substituted or unsubstituted with halogen or azido, $C_{1-6}$ alkynyl, $C_{1-10}$ acyloxy, thiocarboxy, thiocarbamoyl, carbamate, ureido, amidino, or aryloxy; and wherein:
R$_7$, R$_8$, R$_9$, and R$_{10}$ are each independently selected from the group consisting of hydrogen, hydroxy, alkoxy, thiol, thioalkyl, amino, substituted amino, halogen, azido, cyano, carboxy, alkoxycarbonyl, carbamoyl, C$_{1-6}$ alkyl, C$_{1-6}$ alkenyl, or C$_{1-6}$ alkynyl, C$_{1-10}$ acyloxy, aryl, aryloxy, thiocarboxy, thiocarbamoyl, carbamate, ureido, amidino, and aryloxy.

The purine or pyrimidine base R2 is linked through the linker "Z" at any position on the base, but preferably at N9- for the purines, or N1- or N3-position for the pyrimidines.

Preferred compounds of formula (I) are in the cis configuration.

Preferably, n is 0 to 4.

Preferably, X is O, S, CH$_2$, CH-halo, or CH—N$_3$.

Preferably, Q and U are independently O, S, CH$_2$, CHOH, CH-halogen, CH—N$_3$ or both are CH and linked by a double bond.

Preferably, Z is a C$_{1-6}$ alkoxy or (CH$_2$)$_m$ wherein m is preferably from 0 to 6.

Preferred R2 include: A), B), C), D), E), F), G), H), L) and M), N), O), P), Q), R), S), T), U).

More preferably, n is 0 to 2.

More preferably, X is O, S, or CH$_2$.

More preferably, Q and U are independently O, S, CH$_2$, CHOH, CH-halo, or CH—N$_3$.

More preferably, Z is (CH$_2$)$_m$ wherein m is preferably 0 to 4. More preferably, R2 is A), F) or M).

Most preferably, n is 0 or 1.

Most preferably, X is O or S.

Most preferably, Q is O, S, CH$_2$ or CHOH.

Most preferably, U is CH$_2$ or S.

Most preferably, Z is (CH$_2$)$_m$ wherein m is preferably from 0 or 1.

Most preferably, R2 is cytosine, adenine, guanine, uracil, thymine, 2-amino-6-chloropurine, 6-chloropurine, or 2,6-diaminopurine.

In a further or alternative aspect of the invention, there is provided a method for the treatment of a viral infection comprising the step of administering an antivirally effective dose of a compound of formula (I) as defined hereinabove or a pharmaceutically acceptable derivative thereof.

As will be appreciated by those skilled in the art, references herein to treatment extends to prophylaxis as well as to the treatment of established infections of symptoms.

By the term "pharmaceutically acceptable derivative" is meant any pharmaceutically acceptable salt, ester, or salt of such ester of a compound of formula (I), or any other compound which, upon administration to the recipient, is capable of providing (directly or indirectly) a compound of formula (I) or an antivirally active metabolite or residue thereof.

It will be appreciated by those skilled in the art that the compounds of formula (I) may be modified to provide pharmaceutically acceptable derivatives thereof, at functional groups in the base moiety, at the phosphonate group or at the 3- or 4-hydroxy groups of the sugar ring. Modifications at all such functional groups are included within the scope of the invention. However, of particular interest are pharmaceutically acceptable derivatives (e.g. esters) obtained by modifications of the 2-alkyl phosphonate group, or of the 3-, or 4-hydroxy group of the sugar ring.

Preferred esters of the compounds of formula (I) include the compounds in which either one or both of the —OH groups of the phosphonate function is replaced by —OR$_z$, wherein R$_z$ is selected from a straight or branched chain alkyl (e.g. methyl, isopropyl), alkoxyalkyl (e.g. methoxymethyl), aralkyl (e.g. benzyl), aryloxyalkyl (e.g. phenoxymethyl), aryl, acyloxyalkyl (e.g. pivaloyloxymethyl), aryloyloxyalkyl, aracyl, C$_{1-10}$ acyl, and phosphate to provide a diphosphate or a triphosphate nucleotide analogue. Alternatively, the —OH function may be replaced by a substituted or unsubstituted amino group. Examples of substituted amino groups are amino acids.

The —OH function of the phosphonate group may also be replaced by a carboxyl function (CH$_2$)$_n$—C(O)R$_y$, wherein n is 0 to 6 and in which R$_y$ is selected from a hydroxy, alkoxy, substituted or unsubstituted aryloxy, or substituted or unsubstituted amino.

Also included as esters of compounds of formula (I) are nucleotides dimers linked by a phosphonate or phosphate linkage:

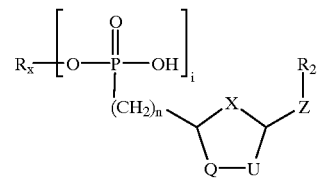

wherein R$_x$ is a nucleotide analogue of formula (I) or any other known cyclic or acyclic nucleosides or nucleotides, and i is 1, 2 or 3. Preferably, other known nucleosides or nucleotides may be chosen from: AZT, ddT, ddI, D4T, HPMPC, HPMPG, HPMPA, PMEA, PMEG, acyclovir, or 3TC. Most preferably, R$_x$ is a nucleotide analogue of formula (I).

Other preferred esters of the compounds of formula (I) include the compounds in which either one or both of the 3-, or 4-hydroxy group of the sugar ring [when Q or U is CHOH or CH—CH$_2$OH] is replaced by a phosphoramidite or by —OR$_z$ wherein R$_z$ is as defined above, or R$_z$ is a nucleotide analogue derived from R$_x$ wherein R$_x$ is as defined above.

With regard to the above described esters, unless otherwise specified, any alkyl moiety present advantageously contains 1 to 16 carbon atoms, particularly 1 to 4 carbon atoms and could contain one or more double bonds. In particular the esters may be C$_{1-16}$ alkyl esters, C$_{1-6}$ alkyl, saturated or unsaturated C$_{1-6}$ alkoxy, nitro or trifluoromethyl groups.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, p-toluenesulphonic, tartaric, acetic, citric, methanesulphonic, formic, benzoic, malonic, naphtalene-2-sulphonic and benzenesulphonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and N(R')$_4$$^+$(where R' is C$_{1-4}$alkyl) salts.

Generally, the compounds of formula (I) may be prepared by coupling a 2-dialkylphosphonate derivative of formula (II):

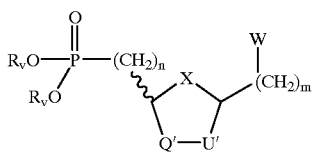

(II)

wherein n, m and X, are defined above,
Q' and U' are independently O, S, or CH—W' wherein W' is a hydroxy protecting group (such as acyloxy, aracyloxy, or silyloxy) or a displaceable group (such as mesyloxy, tosyloxy, or halogen) or an ester that may be modified to a displaceable group;
W is a displaceable group (such as tosylate or halogen) or a hydroxy group; and
$R_v$ is a hydroxy protecting group such as $C_{1-6}$ alkyl or an aryl;
with R2' which is a purine or pyrimidine base or analog or derivative thereof, modified or not, to yield a compound of formula (I):

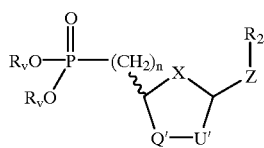

(I)

wherein Z is as defined above.

This reaction may be carried out directly when W is a displaceable group, or under Mitsunobu reaction conditions when W is hydroxy.

The ester of (I) may then, optionally, be converted to yield a phosphonate of formula (I).

By modified purine or pyrimidine base or analog or derivative thereof is meant a base that is previously hydroxylated or aminated to a position so that it will be linked to the sugar via an alkoxy or aminoalkyl group respectively. However, when Z is thioalkyl, it is the 5 position of the sugar that is thiolated prior to coupling of the base.

The intermediate of formula (II) may be produced by different processes depending on the different substituents of the sugar ring. For example, (II) will be made by different routes when n is 0 or when n>0. Similarly, a third route will be employed when Q and U are independently $CH_2$, CHOH, CH-halo, or CH—$N_3$, CH—$CH_2(R_b)$, or are both CH=CH. A fourth route is presented when U is O, or S.

The processes illustrated in the present application are not intended to be limiting but are intended to be representative of how a person skilled in the art of nucleotide chemistry may produce such compounds. It will be obvious for people skilled in the art to design similar processes for producing all compounds encompassed by the invention, without undue experimentation, by reading the schemes below.

The compounds of formula (I) where X is O or S, Q is O, S, U is $CH_2$ and n is 0 (i.e. where the phosphinoyl residue is linked directly to the sugar) may be prepared by the process outlined in Scheme 1. This scheme relates to examples 1 to 55, and 129 and 130 of the present application.

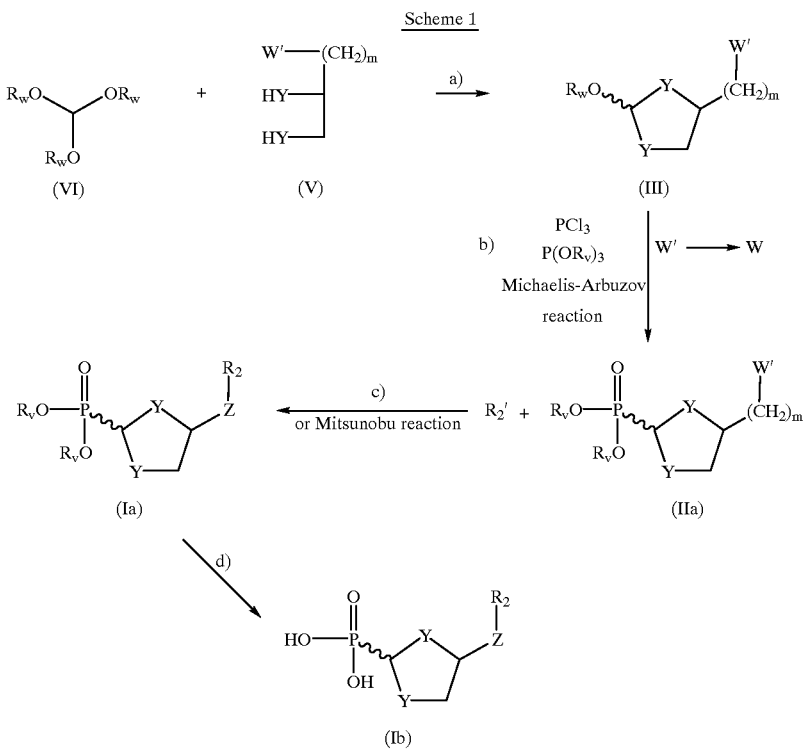

wherein Y is O or S;

OR$_w$ is a leaving group wherein R$_w$ is a C$_{1-6}$ alkyl (preferably, methyl, ethyl, or isopropyl);

R$_v$ is a hydroxy protecting group such as a C$_{1-6}$ alkyl or an aryl (preferably methyl, ethyl, isopropyl, or benzyl);

Z and R2 is as defined above;

R2' is R2 or a hydroxylated or an aminated R2 (preferably at position N9 for the purine and N1 or N3 for the pyrimidines);

m is 0 or an integer (preferably 1 to 6);

W' is a hydroxy protecting group (such as silyloxy, acyloxy or aracyloxy), a displaceable group (such as mesyloxy, tosyloxy, halogen), or an ester group that may be modified to a displaceable group; and W is a displaceable group (such as tosylate or halogen), or a hydroxy group (when the Mitsunobu reaction is carried out).

The steps illustrated in Scheme 1 can be briefly described as follows:

a) a linear alkane derivative (V) substituted at 1 and 2 positions by alcohol or mercapto groups and substituted at position 3 by a displaceable group was condensed with trialkylorthoformate (VI) in the presence of an acid catalyst (preferably p-toluenesulfonic acid) and refluxed in organic solvent (preferably benzene or toluene) to yield 2-alkoxy-sugar of formula (III) as a mixture of cis and trans isomers;

b) The 2-alkoxy functionality of the compound of formula (III) was converted to a 2-dialkylphosphonate derivative (IIa) with a phosphonate-containing agent such as trialkylphosphite and phosphorus trichloride in the presence of zinc chloride as a catalyst under Michaelis-Arbuzov conditions (A. E. Arbuzov, Pure Applied Chem., 9, 307–335 (1964));

At this stage, the compound of formula (IIa) was optionally separated to its cis and trans isomers before further steps were carried out;

c) After the function W' had been modified to a displaceable group W (if necessary), the compound (IIa) was condensed with a purine or pyrimidine base, modified or not, derivative or analogue thereof (R2'), by displacing W or by Mitsunobu reaction, to yield (Ia), which is an ester of compounds of formula (I);

At this stage, R2 can be converted to another R2 if necessary.

d) Once made, esters (Ia) were converted to the corresponding phosphonate derivatives of formula (Ib) by any method well known in the art such as hydrolysis using TMSI or TMSBr (C. E. McKenna, J. Schmidhauser, J. Chem. Soc. Chem. Commun., 1979, 739).

Moreover, if Y is S, it may be oxidized to SO or SO$_2$ by any method well known in the art.

As shown in Scheme 1, the length of the alkyl chain between the HY- function and the group W' can be elongated (m=2, 3, 4, 5, 6, etc.). In this case, the starting compound is chosen from linear 1,2,4-substituted butane-, linear 1,2,5-substituted pentane-, linear 1,2,6-substituted hexane-, etc. such that the linker is also linear. In addition, there is also the possibility of having R2 linked directly to the sugar ring, in which case, the linker is (CH$_2$)$_m$ where m is 0. For example, in this case, the starting compound (V) is:

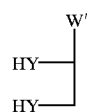

In the case of compounds of formula (I) when Z is oxygen, the intermediate of formula (II) where m is 0, is condensed with a base previously hydroxylated at position N1 or N3 for the pyrimidines or N9 for the purines. Such hydroxylation is effected by any method known or published in the art (S. Bailey, M. R. Harnden, R. L. Jarnest, A. Parkin and M. R. Boyd, J. Med. Chem., 1991, 34, 57–65). Alternatively, when Z is alkoxy, the intermediate (II) where m>0, is condensed with a hydroxylated base.

Similarly, when Z is N(R$_c$)$_2$, compound (II) where m is 0 is condensed with a previously aminated base at the same positions respectively, whereas when Z is aminoalkyl, compound (II) where m>0, is condensed with a aminated base.

The process of scheme 1 is illustrated using specific reagents and compounds, for example, in Scheme 1a.

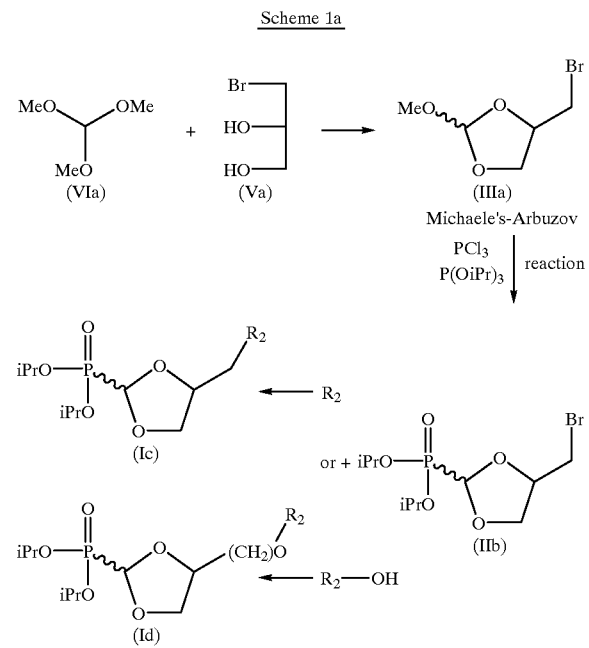

a) 3-bromo-1,2-propanediol (Va) was condensed with trimethylorthoformate (VIa) in presence of p-toluenesulfonic acid as a catalyst and reflux in benzene to yield 2-methoxy-1,3-dioxolane sugar of formula (IIIa);

b) The 2-methoxy function of (IIIa) was converted to a 2-diisopropyl phosphonate derivative under Michaelis-Arbuzov conditions by treatment with triisopropyl phosphite and phosphorus trichloride in the presence of zinc chloride as a catalyst to give a 2-diisopropylphosphinoyl-1,3-dioxolane of formula (IIb);

c) The compound (IIb) was condensed with a purine or pyrimidine base, derivative or analogue thereof, to yield cis- and/or trans-4-(purin- or pyrimidinyl)-2-(diisopropylphosphinoyl)-1,3-dioxolane of formula (Ic) or with a hydroxylated purine or pyrimidine to give (Id).

The esters of formula (Ic) or (Id) can be converted to phosphonates by any means known in the art.

Scheme 2 outlines an alternative process for producing compounds of formula (I) where X is O or S, Q is O or S, U is $CH_2$ and the linker chain between the phosphonate group and the sugar ring is elongated to $(CH_2)_n$, where n is an integer (preferably 1 to 4). Scheme 2 relates to examples 83 to 99 of the present application.

a) dialkylphosphonate alkylaldehyde (VIII) or its dialkylacetal derivative (VII) (n>0) were condensed with an alkane derivative (V) substituted at positions 1 and 2 by a hydroxy or a thiol function and substituted at position 3 by a displaceable group (W') in the presence of an acid catalyst under reflux in an organic solvent (preferably benzene or toluene) to yield 2-dialkylphosphinoylalkyl- sugar of formula (IIc) as a mixture of cis and trans isomers;

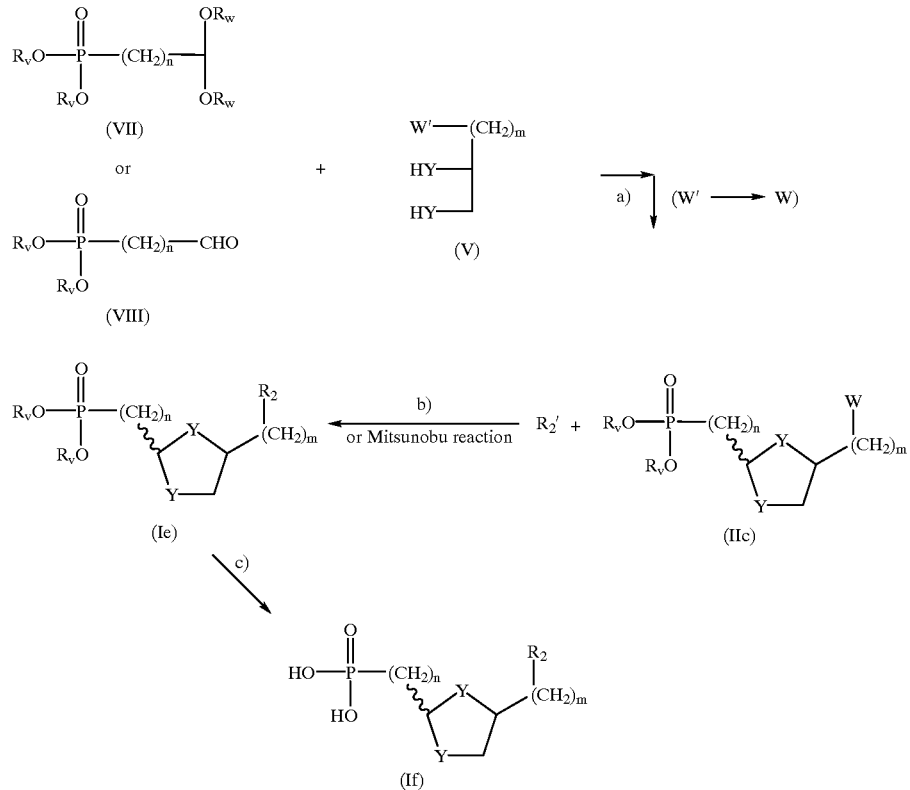

Scheme 2 wherein Y is O or S;

$OR_w$ is a leaving group wherein $R_w$ is a $C_{1-6}$ alkyl (preferably, methyl, ethyl, or isopropyl);

$R_v$ is a hydroxy protecting group such as a $C_{1-6}$ alkyl or an aryl (preferably methyl, ethyl, isopropyl, or benzyl);

Z and R2 is as defined above;

R2' is R2 or a hydroxylated or aminated R2;

n is 0 or an integer (preferably 1 to 4);

W' is a hydroxy protecting group (such as silyloxy, acyloxy or aracyloxy), a displaceable group (such as mesyloxy, tosyloxy, or halogen), or an ester group that may be modified to a displaceable group; and W is a displaceable group (such as tosylate or halogen), or hydroxy (when the Mitsunobu reaction is carried out).

The steps illustrated in Scheme 2 can be briefly described as follows:

At this stage, the compound of formula (IIc) may be optionally separated in its cis and trans isomers before further steps were carried out;

b) after the function (W') had been modified to a displaceable group (W) (if necessary), the compound (IIc) was condensed with a purine or pyrimidine base, modified or not, derivative or analogue thereof (R2'), by displacement of W or the Mitsunobu reaction, to yield compound (Ie) which is an ester of compounds of formula (I) where n>0;

At this stage, R2 can be converted to another R2 if necessary.

c) Once made, these esters (Ie) were converted to the phoshonate derivatives of formula (If) by any means well known in the art such as hydrolysis using TMSI or TMSBr.

Moreover, if Y is S, it may be oxidized to SO or $SO_2$ by any method known in the art.

The process of scheme 2 is illustrated using specific reagents and compounds, for example, in Scheme 2a.

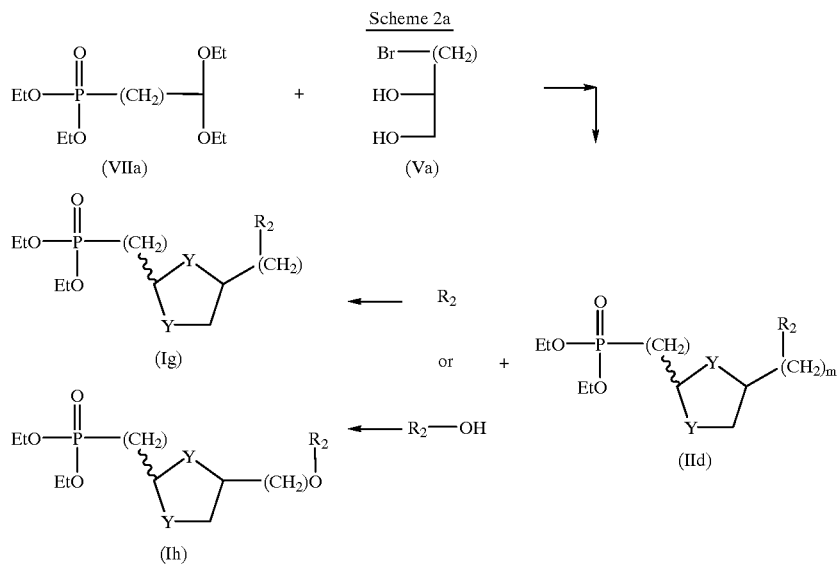

a) Diethylphosphonoacetaldehyde diethylacetal (VIIa) was condensed with 3-bromo-1,2-propanediol (Va) in the presence of p-toluenesulfonic acid as a catalyst and reflux in toluene to yield 2-diethylphosphinoylmethyl-1,3-dioxolane of formula (IId) as a mixture of cis and trans isomers;

b) The compound (IId) was condensed with a purine or pyrimidine base, derivative or analogues thereof, modified or not, to give cis- and/or trans-4-(purin- or pyrimidinyl)-2-(diethylphosphinoylmethyl)-1,3-dioxolane of formula (Ig) or with a hydroxylated purine or pyrimidine to give (Ih).

Scheme 3 outlines an alternative process for producing compounds of formula (I) where Q and U are independently $CH_2$, CHOH, CH-halogen, CH—$N_3$, CH—$CH_2(R_b)$, or both Q and U are CH linked by a double bond. Scheme 3 relates to examples 56 to 82 and 100 to 128 of the present application.

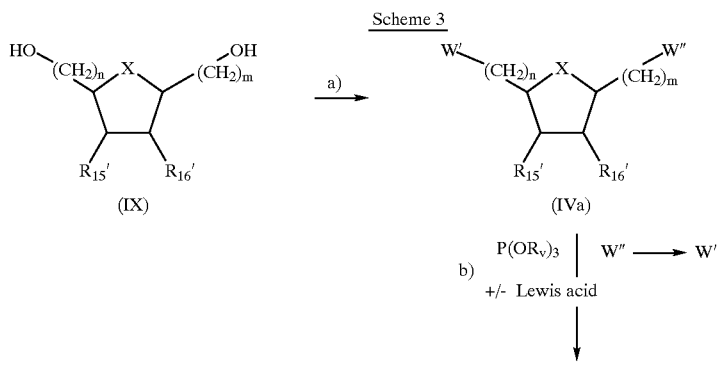

-continued

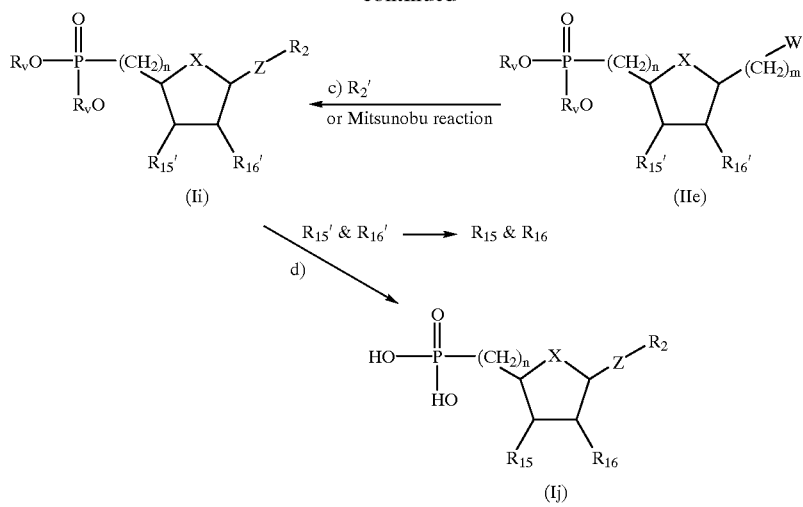

wherein W' is as defined above;
W" has the same definition as W' but may be the same or different;
$R_{15}'$ and $R_{16}'$ are independently H or W', or both form a double bond;
$R_{15}$ and $R_{16}$ are independently H, OH, halogen, azido, SH, $NH_2$, carboxyl, $C_{1-6}$ alkyl, or $CH\!-\!CH_2(R_b)$ wherein $R_b$ is H, OH, SH, $NH_2$, $C_{1-6}$ alkyl, or carboxyl, or both $R_{15}$ and $R_{16}$ form a double bond; and
X, R2', R2, $R_v$ and Z are as defined above.

The steps illustrated in Scheme 3 can be briefly described as follows:

a) Both hydroxy groups of compound (IX) were sequentially converted to form compound (IVa) where W' and W" are similar or different functional groups;

b) The W' functionality of compound (IVa) was then converted to a 2-dialkylphosphonate derivative (IIe) under Arbuzov conditions by treatment with trialkyl phosphite with or without the presence of a Lewis acid (such as $TiCl_4$) as a catalyst. Alternatively, when W' is a displaceable group, the coupling reaction may be carried out under Michaelis-Becker conditions using $O\!=\!P(OR_v)_2^- M\oplus$ wherein M is a metal (such as Li, Na, or K);

At this stage, the compound of formula (IIc) may be optionally separated to its cis and trans isomers before further steps were carried out;

c) After the function W' had been modified to a displaceable group W (if necessary), the compound (IIe) is condensed with a purine or pyrimidine base, modified or not, derivative or analogue thereof (R2'), to yield (Ii) which is an ester of the compound of formula (I).

At this stage, R2 can be converted to another R2 if necessary. Also, if $R_{15}'$ and $R_{16}'$ are W', they may be independently deprotected to $R_{15}$ and $R_{16}$.

d) Once made, esters (Ii) are converted to the corresponding phosphonate derivative of formula (Ij) as described in Schemes 1 and 2.

Scheme 4 outlines an alternative process for producing compounds of formula (I) where Q is $CH_2$ and U is O or S. Scheme 4 relates to example 131 of the present application.

Scheme 4

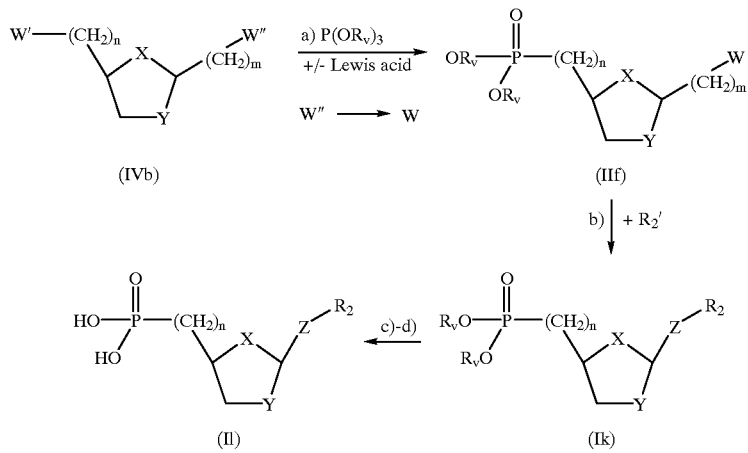

wherein Y is O or S,
W' and W" are as defined above;
X, R2', R2, R$_v$ and Z are as defined above.

The steps illustrated in Scheme 4 can be briefly described as follows:
a) The W' functionality of compound (IVb) was converted to a 2-dialkylphosphonate derivative (IIf) under Michaelis-Arbuzov conditions by treatment with trialkyl phosphite in the presence or absence of a Lewis acid (such as TiCl$_4$) as a catalyst. Alternatively, when W' is a displaceable group, the coupling reaction may be carried out under Michaelis-Becker conditions using O=P(OR$_v$)$_2$$^-$M⊕ wherein M is a metal (Li, Na, or K). At this stage, the compound of formula (IIf) may be optionally separated to its cis and trans isomers before further steps are carried out;
b) After the function W' has been modified to a displaceable group W (if necessary), the compound (IIf) is condensed with a purine or pyrimidine base, modified if necessary, derivative or analogue thereof (R2'), to yield (Ik) which is an ester of the compound of formula (I).
At this stage, R2 can be converted to another R2 if necessary.
c) Once made, esters (Ik) are converted to the corresponding phosphonate derivative of formula (II) as described in Schemes 1 and 2.

Moreover, if Y is S, it may be oxidized to SO or SO$_2$ by any method known in the art.

Therefore, in a further embodiment of the invention, there is provided processes for the synthesis of 2-phosphonate nucleotide analogs of formula (I) comprising the steps described hereinabove.

Intermediates of the compounds of formula (I) include compounds:

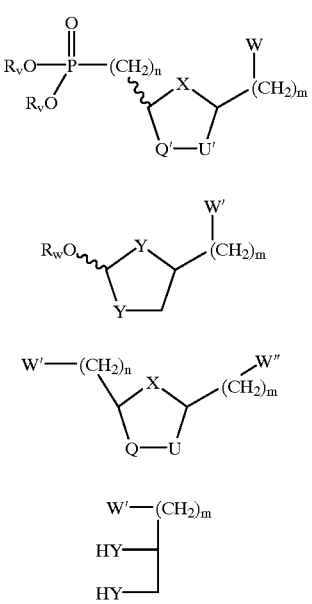

wherein X, Y, Q, U, W, W', W", R$_v$, and R$_w$ are as defined above.

References hereinafter to a compound according to the invention includes both the compound of formula (I) and its pharmaceutically acceptable derivatives. Specific compounds of formula (I) include:
CIS-4-(CYTOSIN-1'-YLMETHYL)-2-(DIHYDROXYPHOSPHINOYL)-1,3-DIOXOLANE, TRANS-4-(CYTOSIN-1'-YLMETHYL)-2-(DIHYDROXYPHOSPHINOYL)-1,3-DIOXOLANE AND MIXTURES THEREOF;
CIS-4-(ADENIN-9'-YLMETHYL)-2-(DIHYDROXYPHOSPHINOYL)-1,3-DIOXOLANE, TRANS-4-(ADENIN-9'-YLMETHYL)-2-(DIHYDROXYPHOSPHINOYL)-1,3-DIOXOLANE AND MIXTURES THEREOF;
CIS-4-(GUANIN-9'-YLMETHYL)-2-(DIHYDROXYPHOSPHINOYL)-1,3-DIOXOLANE, TRANS-4-(GUANIN-9'-YLMETHYL)-2-(DIHYDROXYPHOSPHINOYL)-1,3-DIOXOLANE AMMONIUM SALT AND MIXTURES THEREOF;
CIS-4-(CYTOSIN-1'-YLMETHYL)-2-(DIISOPROPYLOXYPHOSPHINOYL)-1,3-DIOXOLANE TRANS-4-(CYTOSIN-1'-YLMETHYL)-2-(DIISOPROPYLOXYPHOSPHINOYL)-1,3-DIOXOLANE AND MIXTURES THEREOF;
CIS-4-(ADENIN-9'-YLMETHYL)-2-(DIISOPROPYLOXYPHOSPHINOYL)-1,3-DIOXOLANE, TRANS-4-(ADENIN-9'-YLMETHYL)-2-(DIISOPROPYLOXYPHOSPHINOYL)-1,3-DIOXOLANE AND MIXTURES THEREOF;
CIS-4-(2'-AMINO-6'-CHLOROPURIN-9'-YLMETHYL)-2-(DIISOPROPYLOXYPHOSPHINOYL)-1,3-DIOXOLANE, TRANS-4-(2'-AMINO-6'-CHLOROPURIN-9'-YLMETHYL)-2-(DIISOPROPYLOXYPHOSPHINOYL)-1,3-DIOXOLANE AND MIXTURES THEREOF;
CIS-2-(DIISOPROPYLOXYPHOSPHINOYL)-4-(URACIL-1'-YLMETHYL)-1,3-DIOXOLANE, TRANS-2-(DIISOPROPYLOXYPHOSPHINOYL)-4-(URACIL-1'-YLMETHYL)-1,3-DIOXOLANE AND MIXTURES THEREOF;
CIS-2-(DIHYDROXYPHOSPHINOYL)-4-(URACIL-1'-YLMETHYL)-1,3-DIOXOLANE, MONOAMMONIUM SALT, TRANS-2-(DIHYDROXYPHOSPHINOYL)-4-(URACIL-1'-YLMETHYL)-1,3-DIOXOLANE, MONOAMMONIUM SALT AND MIXTURES THEREOF;
CIS-2-(DIISOPROPYLOXYPHOSPHINOYL)-4-(THYMIN-1'-YLMETHYL)-1,3-DIOXOLANE, TRANS-2-(DIISOPROPYLOXYPHOSPHINOYL)-4-(THYMIN-1'-YLMETHYL)-1,3-DIOXOLANE AND MIXTURES THEREOF;
CIS-2-(DIHYDROXYPHOSPHINOYL)-4-(THYMIN-1'-YLMETHYL)-1,3-DIOXOLANE, MONOAMMONIUM SALT, TRANS-2-(DIHYDROXYPHOSPHINOYL)-4-(THYMIN-1'-YLMETHYL)-1,3-DIOXOLANE, MONOAMMONIUM SALT AND MIXTURES THEREOF;
TRANS-2-DIETHYLOXYPHOSPHINOYL-5-(2'-AMINO-6'-CHLOROPURIN-9'-YLMETHYL)-1,3-OXATHIOLANE, CIS-5-(2'-AMINO-6'-CHLOROPURIN-9'-YLMETHYL)-2-(DIETHYLOXYPHOSPHINOYL)-1,3-OXATHIOLANE AND MIXTURES THEREOF;
TRANS 2-DIHYDROXYPHOSPHINOYL-5-(GUANIN-9'-YLMETHYL)-1,3-OXATHIOLANE (BCH-1550), CIS-2-(DIHYDROXYPHOSPHINOYL)- 5-(GUANIN-9'-YLMETHYL)-1,3-OXATHIOLANE, MONOAMMONIUM SALT (BCH-1819) AND MIXTURES THEREOF;
TRANS-2-(DIETHYLOXYPHOSPHINOYL)-5-(THYMIN-1'-YLMETHYL)-1,3-OXATHIOLANE;

TRANS-2-(DIETHYLOXYPHOSPHINOYL)-5-(THYMIN-3'-YLMETHYL)-1,3-OXATHIOLANE;
TRANS-2-(DIHYDROXYPHOSPHINOYL)-5-(THYMIN-1'-YLMETHYL)-1,3-OXATHIOLANE, MONOAMMONIUM SALT (BCH-1820);
TRANS-2-(DIHYDROXYPHOSPHINOYL)-5-(THYMIN-3'-YLMETHYL)-1,3-OXATHIOLANE, MONOAMMONIUM SALT (BCH-1821);
TRANS-2-(DIETHYLOXYPHOSPHINOYL)-5-(URACIL-1'-YLMETHYL)-1,3-OXATHIOLANE;
TRANS-2-(DIETHYLOXYPHOSPHINOYL)-5-(URACIL-3'-YLMETHYL)-1,3-OXATHIOLANE;
TRANS-2-(DIHYDROXYPHOSPHINOYL)-5-(URACIL-1'-YLMETHYL)-1,3-OXATHIOLANE, MONOAMMONIUM SALT;
TRANS-2-(DIHYDROXYPHOSPHINOYL)-5-(URACIL-3'-YLMETHYL)-1,3-OXATHIOLANE, MONOAMMONIUM SALT;
CIS-5-(ADENIN-9'-YLMETHYL)-2-(DIETHYLOXYPHOSPHINOYL)-1,3-OXATHIOLANE;
CIS-5-(ADENIN-9'-YLMETHYL)-2-(DIHYDROXYPHOSPHINOYL)-1,3-OXATHIOLANE, MONOAMMONIUM SALT (BCH-1831);
CIS 4-(2'-AMINO-6'-CHLOROPURIN-9'-YLMETHYL)-2-(DIETHYLOXYPHOSPHINOYL)-1,3-OXATHIOLANE, TRANS 4-(2'-AMINO-6'-CHLOROPURIN-9'-YLMETHYL)-2-(DIETHYLOXYPHOSPHINOYL)-1,3-OXATHIOLANE AND MIXTURES THEREOF;
CIS 2-(DIHYDROXYPHOSPHINOYL)-4-(GUANIN-9'-YLMETHYL)-1,3-OXATHIOLANE, MONOAMMONIUM SALT (BCH-2593), TRANS 2-(DIHYDROXYPHOSPHINOYL)-4-(GUANIN-9'-YLMETHYL)-1,3-OXATHIOLANE, MONOAMMONIUM SALT (BCH-2594) AND MIXTURES THEREOF;
CIS 4-(2'-AMINO-6'-CHLOROPURIN-9'-YLMETHYL)-2-(DIETHYLOXYPHOSPHINOYL)-1,3-DITHIOLANE, TRANS 4-(2'-AMINO-6'-CHLORO-9'-YLMETHYL)-2-(DIETHYLOXYPHOSPHINOYL)-1,3-DITHIOLANE AND MIXTURES THEREOF;
CIS 2-(DIHYDROXYPHOSPHINOYL)-4-(GUANIN-9'-YLMETHYL)-1,3-DITHIOLANE, MONOAMMONIUM SALT (BCH-2599), TRANS 2-(DIHYDROXYPHOSPHINOYL)-4-(GUANIN-9'-YLMETHYL)-1,3-DITHIOLANE, MONOAMMONIUM SALT (BCH-2665) AND MIXTURES THEREOF;
(±)-2-DIETHOXYPHOSPHINOYL-5-(CYTOSIN-1'-YLMETHYL)-TETRAHYDROFURAN;
(±)-CIS-2-DIHYDROXYPHOSPHINOYL-5-(CYTOSIN-1'-YLMETHYL)-TETRAHYDROFURAN MONOAMMONIUM SALT, TRANS-2-DIHYDROXYPHOSPHINOYL-5-(CYTOSIN-1'-YLMETHYL)-TETRAHYDROFURAN MONOAMMONIUM SALT AND MIXTURES THEREOF;
(±)-CIS-5-(6'-CHLOROPURIN-9'-YLMETHYL)-2-DIETHOXYPHOSPHINOYL-TETRAHYDROFURAN, TRANS-5-(6'-CHLOROPURIN-9'-YLMETHYL)-2-DIETHOXYPHOSPHINOYL-TETRAHYDROFURAN AND MIXTURES THEREOF;
(±)-CIS-5-(ADENIN-9'-YLMETHYL)-2-DIHYDROXYPHOSPHINOYL-TETRAHYDROFURAN, (±)-TRANS-5-(ADENIN-9'-YLMETHYL)-2-DIHYDROXYPHOSPHINOYL-TETRAHYDROFURAN AND MIXTURES THEREOF;
(±)-CIS-5-(2'-AMINO-6'-CHLOROPURIN-9'-YLMETHYL)-2-DIETHOXYPHOSPHINOYL-TETRAHYDROFURAN, (±)-TRANS-5-(2'-AMINO-6'-CHLOROPURIN-9'-YLMETHYL)-2-DIETHOXYPHOSPHINOYL-TETRAHYDROFURAN AND MIXTURES THEREOF;
(±)-CIS-5-(2'-AMINO-6'-CHLOROPURIN-9'-YLMETHYL)-2-DIHYDROXYPHOSPHINOYL-TETRAHYDROFURAN, MONOAMMONIUM SALT,
(±)-TRANS-5-(2'-AMINO-6'-CHLOROPURIN-9'-YL)METHYL-2-DIHYDROXYPHOSPHINOYL-TETRAHYDROFURAN MONOAMMONIUM SALT AND MIXTURES THEREOF;
(±)-TRANS-2-DIHYDROXYPHOSPHINOYL-5-(GUANIN-9'-YLMETHYL)-TETRAHYDROFURAN, MONOAMMONIUM SALT (BCH-1573), (±)-CIS-2-30 DIHYDROXYPHOSPHINOYL-5-(GUANIN-9'-YLMETHYL)-TETRAHYDROFURAN, MONOAMMONIUM SALT (BCH-1570) AND MIXTURES THEREOF;
(±)-TRANS-2-DIHYDROXYPHOSPHINOYL-5-(2',6'-DIAMINOPURIN-9'-YLMETHYL)-TETRAHYDROFURAN, MONOAMMONIUM SALT (BCH-1572),
(±)-CIS-2-DIHYDROXYPHOSPHINOYL-5-(2',6'-DIAMINOPURIN-9'-YLMETHYL)-TETRAHYDROFURAN, MONOAMMONIUM SALT AND MIXTURES THEREOF;
(±)-CIS-2-DIETHOXYPHOSPHINOYL-5-(THYMIN-1'-YLMETHYL)-TETRAHYDROFURAN, (±)-TRANS-2-DIETHOXYPHOSPHINOYL-5-(THYMIN-1'-YLMETHYL)-TETRAHYDROFURAN AND MIXTURES THEREOF;
(±)-CIS-2-DIHYDROXYPHOSPHINOYL-5-(THYMIN-1'-YLMETHYL)-TETRAHYDROFURAN, MONOAMMONIUM SALT, (±)-TRANS-2-DIHYDROXYPHOSPHINOYL-5-(THYMIN-1'-YLMETHYL)-TETRAHYDROFURAN MONOAMMONIUM SALT AND MIXTURES THEREOF;
(±)-CIS-2-DIETHOXYPHOSPHINOYL-5-(URACIL-1'-YLMETHYL)-TETRAHYDROFURAN, (±)-TRANS-2-DIETHOXYPHOSPHINOYL-5-(URACIL-1'-YLMETHYL)-TETRAHYDROFURAN AND MIXTURES THEREOF;
(±)-CIS-2-DIHYDROXYPHOSPHINOYL-5-(URACIL-1'-YLMETHYL)-TETRAHYDROFURAN, MONOAMMONIUM SALT, (±)-TRANS-2-DIHYDROXYPHOSPHINOYL-5-(URACIL-1'-YLMETHYL)-TETRAHYDROFURAN, MONOAMMONIUM SALT AND MIXTURES THEREOF;
CIS-4-(2'-AMINO-6'-CHLOROPURIN-9'-YLMETHYL)-2-(DIETHYLOXYPHOSPHINOYLMETHYL)-1,3-DIOXOLANE, TRANS-4-(2'-AMINO-6'-CHLOROPURIN-9'-YLMETHYL)-2-(DIETHYLOXYPHOSPHINOYLMETHYL)-1,3-DIOXOLANE AND MIXTURES THEREOF;
CIS-2-(DIETHYLOXYPHOSPHINOYLMETHYL)-4-(GUANIN-9'-YLMETHYL)-1,3-DIOXOLANE, TRANS-2-(DIETHYLOXYPHOSPHINOYLMETHYL)-4-(GUANIN-9'-YLMETHYL)-1,3-DIOXOLANE AND MIXTURES THEREOF;
CIS-2-(DIHYDROXYPHOSPHINOYLMETHYL)-4-(GUANIN-9'-YLMETHYL)-1,3-DIOXOLANE, MONOAMMONIUM SALT (BCH-1845), TRANS-2-

(DIHYDROXYPHOSPHINOYLMETHYL)-4-(GUANIN-9'-YLMETHYL)-1,3-DIOXOLANE, MONOAMMONIUM SALT (BCH-1846) AND MIXTURES THEREOF;
CIS-4-(2',6'-DIAMINOPURIN-9'-YLMETHYL)-2-(DIHYDROXY PHOSPHINOYLMETHYL)-1,3-DIOXOLANE, MONOAMMONIUM SALT, TRANS-4-(2',6'-DIAMINOPURIN-9'-YLMETHYL)-2-(DIHYDROXY PHOSPHINOYLMETHYL)-1,3-DIOXOLANE, MONOAMMONIUM SALT (BCH-2589) AND MIXTURES THEREOF;
CIS-4-(ADENIN-9'-YLMETHYL)-2-(DIETHYLOXYPHOSPHINOYLMETHYL)-1,3-DIOXOLANE, TRANS-4-(ADENIN-9'-YLMETHYL)-2-(DIETHYLOXYPHOSPHINOYLMETHYL)-1,3-DIOXOLANE AND MIXTURES THEREOF;
CIS-4-(ADENIN-9'-YLMETHYL)-2-(DIHYDROXYPHOSPHINOYLMETHYL)-1,3-DIOXOLANE, MONOAMMONIUM SALT, TRANS-4-(ADENIN-9'-YLMETHYL)-2-(DIHYDROXYPHOSPHINOYLMETHYL)-1,3-DIOXOLANE, MONOAMMONIUM SALT AND MIXTURES THEREOF;
(2R,4S)-4-(2'-AMINO-6'-CHLOROPURIN-9'-YLMETHYL)-2-(DIETHYLOXYPHOSPHINOYLMETHYL)-1,3-DIOXOLANE, (2S,4S)-4-(2'-AMINO-6'-CHLOROPURIN-9'-YLMETHYL)-2-(DIETHYLOXY PHOSPHINOYLMETHYL)-1,3-DIOXOLANE, (2R,4R)-4-(2'-AMINO-6'-CHLOROPURIN-9'-YLMETHYL)-2-(DIETHYLOXYPHOSPHINOYLMETHYL)-1,3-DIOXOLANE, (2S,4R)-4-(2'-AMINO-6'-CHLOROPURIN-9'-YLMETHYL)-2-(DIETHYLOXYPHOSPHINOYLMETHYL)-1,3-DIOXOLANE AND MIXTURES THEREOF;
(2R,4S)-2-(DIETHYLOXYPHOSPHINOYLMETHYL)-4-(GUANIN-9'-YLMETHYL)-1,3-DIOXOLANE, (2S,4S)-2-(DIETHYLOXY PHOSPHINOYLMETHYL)-4-(GUANIN-9'-YLMETHYL)-1,3-DIOXOLANE, (2S,4R)-2-(DIETHYLOXYPHOSPHINOYLMETHYL)-4-(GUANIN-9'-YLMETHYL)-1,3-DIOXOLANE, (2R,4R)-2-(DIETHYLOXY PHOSPHINOYLMETHYL)-4-(GUANIN-9'-YLMETHYL)-1,3-DIOXOLANE AND MIXTURES THEREOF;
(2R,4S)-2-(DIHYDROXYPHOSPHINOYLMETHYL)-4-(GUANIN-9'-YLMETHYL)-1,3-DIOXOLANE, MONOAMMONIUM SALT, (2S,4S)-2-(DIHYDROXYPHOSPHINOYLMETHYL)-4-(GUANIN-91-YLMETHYL)-1,3-DIOXOLANE, MONOAMMONIUM SALT, (2S,4R)-2-(DIHYDROXYPHOSPHINOYLMETHYL)-4-(GUANIN-9'-YLMETHYL)-1,3-DIOXOLANE, MONOAMMONIUM SALT, (2R,4R)-2-(DIHYDROXYPHOSPHINOYLMETHYL)-4-(GUANIN-9'-YLMETHYL)-1,3-DIOXOLANE, MONOAMMONIUM SALT AND MIXTURES THEREOF;
(+)-(2S,5S)-5-(2'-AMINO-6'-CHLOROPURIN-9'-YLMETHYL)-2-DIETHOXYPHOSPHINOYL-TETRAHYDROFURAN, (−)-(2R,5R)-5-(2'-AMINO-6'-CHLOROPURIN-9'-YLMETHYL)-2-DIETHOXYPHOSPHINOYL-TETRAHYDROFURAN, (+)-(2S,5S)-2-DIHYDROXYPHOSPHINOYL-5-(GUANIN-9'-YLMETHYL)-TETRAHYDROFURAN, MONOAMMONIUM SALT (BCH-1850), (−)-(2R,5R)-2-DIHYDROXYPHOSPHINOYL-5-(GUANIN-9'-YLMETHYL)-TETRAHYDROFURAN, MONOAMMONIUM SALT AND MIXTURES THEREOF;
(+)-(2S,5S)-5-(2',6'-DIAMINOPURIN-9'-YLMETHYL)-2-DIHYDROXYPHOSPHINOYL-TETRAHYDROFURAN, MONOAMMONIUM SALT, (−)-(2R,5R)-5-(2',6'-DIAMINOPURIN-9'-YLMETHYL)-2-DIHYDROXY PHOSPHINOYL-TETRAHYDROFURAN, MONOAMMONIUM SALT AND MIXTURES THEREOF;
(+)-(2S,5S)-5-(2'-AMINOPURIN-9'-YLMETHYL)-2-DIETHOXYPHOSPHINOYL-TETRAHYDROFURAN;
(+)-(2S,5S)-5-(2'-AMINOPURIN-9'-YLMETHYL)-2-DIHYDROXYPHOSPHINOYL-TETRAHYDROFURAN, MONOAMMONIUM SALT;
(−)-(2R,5S)-5-(2'-AMINO-6'-CHLOROPURIN-9'-YLMETHYL)-2-DIETHOXYPHOSPHINOYL-TETRAHYDROFURAN;
(+)-(2S,5R)-5-(2'-AMINO-6'-CHLOROPURIN-9'-YLMETHYL)-2-DIETHOXYPHOSPHINOYL-TETRAHYDROFURAN;
(−)-(2R,5S)-2-DIHYDROXYPHOSPHINOYL-5-(GUANIN-9'-YLMETHYL)-TETRAHYDROFURAN, MONOAMMONIUM SALT (BCH-1868), (+)-(2S,5R)-2-DIHYDROXYPHOSPHINOYL-5-(GUANIN-9'-YLMETHYL)-TETRAHYDROFURAN, MONOAMMONIUM SALT (BCH-1867) AND MIXTURES THEREOF;
(−)-(2R,5S)-5-(2',6'-DIAMINOPURIN-9'-YLMETHYL)-2-DIHYDROXYPHOSPHINOYL-TETRAHYDROFURAN, MONOAMMONIUM SALT, (+)-(2S,5R)-5-(2',6'-DIAMINOPURIN-9'-YLMETHYL)-2-DIHYDROXYPHOSPHINOYL-TETRAHYDROFURAN, MONOAMMONIUM SALT AND MIXTURES THEREOF;
(2S,3R,SS)-5-[2'-AMINO-6'-CHLOROPURIN-9'-YLMETHYL]-3-T-BUTYLDIMETHYLSILYLOXY-2-DIISOPROPYLOXYPHOSPHINOYL-TETRAHYDROFURAN; AND
(2S,3R,5S)-2-DIIHYDROXYPHOSPHINOYL-5-(GUANIN-9'-YLMETHYL)-3-HYDROXY-TETRAHYDROFURAN, MONOAMMONIUM SALT.

Preferred intermediates of the compounds of formula (I) include:
CIS-4-(BROMOMETHYL)-2-METHOXY-1,3-DIOXOLANE, TRANS-4-(BROMOMETHYL)-2-METHOXY-1,3-DIOXOLANE AND MIXTURES THEREOF;
CIS-4-(BROMOMETHYL)-2-ISOPROPOXY-1,3-DIOXOLANE, TRANS-4-(BROMOMETHYL)-2-ISOPROPOXY-1,3-DIOXOLANE AND MIXTURES THEREOF;
CIS-4-(BROMOMETHYL)-2-(DIISOPROPYLOXYPHOSPHINOYL)-1,3-DIOXOLANE, TRANS-4-(BROMOMETHYL)-2-(DIISOPROPYLOXYPHOSPHINOYL)-1,3-DIOXOLANE AND MIXTURES THEREOF;
1-T-BUTYLDIPHENYLSILYLOXY-3-MERCAPTO-2-PROPANOL CIS-5-(T-BUTYLDIPHENYLSILYLOXYMETHYL)-2-(DIETHYLOXYPHOSPHINOYL)-1,3-OXATHIOLANE, TRANS-5-(T-BUTYLDIPHENYLSILYLOXYMETHYL)-2-(DIETHYLOXYPHOSPHINOYL)-1,3-OXATHIOLANE AND MIXTURES THEREOF;
TRANS-2-DIETHYLOXYPHOSPHINOYL-5-HYDROXYMETHYL-1,3-OXATHIOLANE;
TRANS-2-DIETHYLOXYPHOSPHINOYL-5-P-TOLUENESULFONYLOXYMETHYL-1,3-OXATHIOLANE;

CIS-2-(DIETHYLOXYPHOSPHINOYL)-5-HYDROXYMETHYL-1,3-OXATHIOLANE, TRANS-2-(DIETHYLOXYPHOSPHINOYL)-5-HYDROXYMETHYL-1,3-OXATHIOLANE AND MIXTURES THEREOF;
METHYL-3-T-BUTYLDIPHENYLSILYLOXY-2-HYDROXYPROPIONATE;
METHYL 3-T-BUTYLDIPHENYLSILYLOXY-2-THIOACETOXYPROPIONATE;
3-T-BUTYLDIPHENYLSILYLOXY-2-MERCAPTOPROPANOL;
CIS-4-(T-BUTYLDIPHENYLSILYLOXYMETHYL)-2-(DIETHYLOXYPHOSPHINOYL)-1,3-OXATHIOLANE, TRANS-4-(T-BUTYLDIPHENYLSILYLOXYMETHYL)-2-(DIETHYLOXYPHOSPHINOYL)-1,3-OXATHIOLANE AND MIXTURES THEREOF;
CIS-2-(DIETHYLOXYPHOSPHINOYL)-4-HYDROXYMETHYL-1,3-OXATHIOLANE, TRANS-2-(DIETHYLOXYPHOSPHINOYL)-4-HYDROXYMETHYL-1,3-OXATHIOLANE AND MIXTURES THEREOF;
1-T-BUTYLDIMETHYLSILYLOXY-2,3-DIMERCAPTOPROPANE;
4-T-BUTYLDIMETHYLSILYLOXYMETHYL-2-ETHOXY-1,3-DITHIOLANE;
CIS-4-(T-BUTYLDIMETHYLSILYLOXYMETHYL)-2-(DIETHYLOXYPHOSPHINOYL)-1,3-DITHIOLANE, TRANS-4-(T-BUTYLDIMETHYLSILYLOXYMETHYL)-2-(DIETHYLOXYPHOSPHINOYL)-1,3-DITHIOLANE AND MIXTURES THEREOF;
CIS-2-(DIETHYLOXYPHOSPHINOYL)-4-HYDROXYMETHYL-1,3-DITHIOLANE, TRANS-2-(DIETHYLOXYPHOSPHINOYL)-4-HYDROXYMETHYL-1,3-DITHIOLANE AND MIXTURES THEREOF;
(±)-DIHYDRO-5-HYDROXYMETHYL-2(3H)-FURANONE;
(±)-DIHYDRO-5-(P-TOLUENESULFONYLOXYMETHYL)-2(3H)-FURANONE;
(±)2-HYDROXY-5-(P-TOLUENESULFONYLOXYMETHYL)-TETRAHYDROFURAN;
(±)-2-ACETOXY-5-(P-TOLUENESULFONYLOXYMETHYL)-TETRAHYDROFURAN;
(±)-2-DIETHOXYPHOSPHINOYL-5-(P-TOLUENESULFONYLOXYMETHYL)-TETRAHYDROFURAN;
(±)-CIS-5-BROMOMETHYL-2-DIETHOXYPHOSPHINOYL-TETRAHYDROFURAN. TRANS-5-BROMOMETHYL-2-DIETHOXYPHOSPHINOYL-TETRAHYDROFURAN AND MIXTURES THEREOF;
CIS-4-(BROMOMETHYL)-2-(DIETHYLOXYPHOSPHINOYLMETHYL)-1,3-DIOXOLANE, TRANS-4-(BROMOMETHYL)-2-(DIETHYLOXY PHOSPHINOYLMETHYL)-1,3-DIOXOLANE AND MIXTURES THEREOF;
(2R)-3-BROMO-1,2-PROPANEDIOL;
(2S)-3-BROMO-1,2-PROPANEDIOL;
(2R,4R)-4-(BROMOMETHYL)-2-(DIETHYLOXYPHOSPHINOYLMETHYL)-1,3-DIOXOLANE, (2S,4R)-4-(BROMOMETHYL)-2-(DIETHYLOXY PHOSPHINOYLMETHYL)-1,3-DIOXOLANE, (2R,4S)-4-(BROMOMETHYL)-2-(DIETHYLOXYPHOSPHINOYLMETHYL)-1,3-DIOXOLANE, (2S,4S)-4-(BROMOMETHYL)-2-(DIETHYLOXYPHOSPHINOYLMETHYL)-1,3-DIOXOLANE AND MIXTURES THEREOF;
(5S)-5-(BROMOMETHYL)-2-HYDROXY-TETRAHYDROFURAN, (5R)-5-(BROMOMETHYL)-2-HYDROXY-TETRAHYDROFURAN AND MIXTURES THEREOF;
(5S)-2-O-ACETYL-5-(BROMOMETHYL)-TETRAHYDROFURAN, (5R)-2-O-ACETYL-5-(BROMOMETHYL)-TETRAHYDROFURAN AND MIXTURES THEREOF;
(−)-(2S,5S)-5-(BROMOMETHYL)-2-DIETHOXYPHOSPHINOYL-TETRAHYDROFURAN, (−)-(2R,5S)-5-(BROMOMETHYL)-2-DIETHOXYPHOSPHINOYL-TETRAHYDROFURAN, (+)-(2S,5R)-5-(BROMOMETHYL)-2-DIETHOXYPHOSPHINOYL-TETRAHYDROFURAN, (+)-(2R,5R)-5-(BROMOMETHYL)-2-DIETHOXYPHOSPHINOYL-TETRAHYDROFURAN AND MIXTURES THEREOF;
5-O-BENZOYL 3-O-(4-FLUOROPHENYL THIONOCARBONATE)-1,2-O-ISOPROPYLIDENE-D-XYLOFURANOSE;
5-O-BENZOYL 3-DEOXY-1,2-O-ISOPROPYLIDENE-D-XYLOFURANOSE;
(2-METHOXYETHYL)-5-O-BENZOYL-3-DEOXY-D-XYLOFURANOSE;
(2-METHOXYETHYL)-5-O-BENZOYL-2-O-T-BUTYLDIMETHYLSILYL-3-DEOXY-D-XYLOFURANOSE;
(2S,3R,5S)-5-BENZOYLOXYMETHYL-3-T-BUTYLDIMETHYLSILYLOXY-2-DIISOPROPYLOXYPHOSPHINOYL-TETRAHYDROFURAN;
(2S,3R,5S)-5-HYDROXYMETHYL-3-T-BUTYLDIMETHYLSILYLOXY-2-DIISOPROPYLOXYPHOSPHINOYL-TETRAHYDROFURAN;
(2S,3R,5S)-5-METHANESULFONYLOXYMETHYL-3-T-BUTYLDIMETHYLSILYLOXY-2-DIISOPROPYLOXYPHOSPHINOYL-TETRAHYDROFURAN;
(2S,3R,5S)-5-[2'-AMINO-6'-CHLOROPURIN-9'-YLMETHYL]-3-T-BUTYLDIMETHYLSILYLOXY-2-DIISOPROPYLOXYPHOSPHINOYL-TETRAHYDROFURAN;
CIS-5-(T-BUTYLDIPHENYLSILYLOXYMETHYL)-2-(DIETHYLOXYPHOSPHINOYLMETHYL)-1,3-OXATHIOLANE, TRANS-5-(T-BUTYLDIPHENYLSILYLOXYMETHYL)-2-(DIETHYLOXYPHOSPHINOYLMETHYL)-1,3-OXATHIOLANE AND MIXTURES THEREOF;
CIS-2-(DIETHYLOXYPHOSPHINOYLMETHYL)-5-(HYDROXYMETHYL)-1,3-OXATHIOLANE, TRANS-2-(DIETHYLOXYPHOSPHINOYLMETHYL)-5-(HYDROXYMETHYL)-1,3-OXATHIOLANE AND MIXTURES THEREOF; AND
2-BENZOYLOXYMETHYL-5-DIISOPROPOXYPHOSPHINOYL-1,3-OXATHIOLANE.

The compounds of formula (I) either as the racemic mixture or as the individual enantiomer may be useful for the treatment of humans or mammalians to inhibit at least one of the following viruses: HCMV (Human Cytomegalovirus), HSV-1 or HSV-2 (Herpes Simplex 1 or 2), HIV (Human Immunodeficiency Virus), HTLV (Human T-lymphotropic virus), HBV (Hepatitis B Virus), or MCMV (murine cytomegalovirus).

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferable about 3 to about 30 $\mu$M. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial, antifungal, and antiviral agents, immunomodulators or preservatives.

The compounds of the invention may also be used in combination with other therapeutic or prophylactic agents for example other antiinfective agents. In particular the compounds of the invention may be employed together with known antiviral, antimicrobial, or antifungal agents or immunomodulators.

The invention thus provides, in a further aspect, a combination comprising a compound of formula (I) or a physiologically acceptable derivative thereof together with another therapeutically active agent, in particular an antiviral agent.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

The individual components of such combinations may be administered either sequentially or simultaneously in separate or combined pharmaceutical formulations.

When the compound (I) or a pharmaceutically acceptable derivative thereof is used in combination with a second therapeutic agent active against the same virus the dose of each compound may be either the same as or differ from that when the compound is used alone. Appropriate doses will be readily appreciated by those skilled in the art.

The compounds and process of this invention are illustrated by the following examples which should not be interpreted as a limitation thereof.

EXAMPLES

Example 1

CIS AND TRANS 4-(BROMOMETHYL)-2-METHOXY-1,3-DIOXOLANE

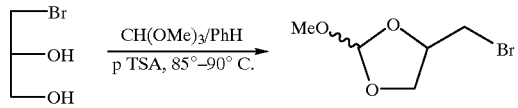

To a solution of 3-bromo-1,2-propanediol (6.0 g, 38.7 mmol) in benzene (90 mL) was added trimethylorthoformate (4.23 mL, 38.7 mmol, 1 eq.) and p-toluenesulfonic acid (pTSA, few crystals). The mixture was stirred for 20 hr at 85°–90° C., then cooled to room temperature and benzene was removed under reduced pressure. The crude material was obtained in 96% yield (7.26 g) as a mixture of cis and trans isomers in a 1:1 ratio.

$^1$H NMR (300 MHz, CDCl$_3$) δ: 3.34 and 3.35 (2s, 3H, OCH$_3$), 3.35 (m, 1H, C$\underline{H}_A$H$_B$Br), 3.44 and 3.58 (dd, 0.5H, J=5.0 Hz, 15.0 Hz, and dd, 0.5H, J=5.0 Hz, 9.9 Hz, CH$_{AH_B}$Br), 3.92 (dd, 0.5H, J=8.3 Hz, 10.7 Hz, and d, 0.5H, J=8.2 Hz, H-5a), 4.21 (dd, 0.5H, J=6.9 Hz, 15.0 Hz, and d, 0.5H, J=8.3 Hz, H-5b), 4.45 and 4.55 (2m, 1H, H-4), 5.80 and 5.82 (2s, 1H, H-2).

Example 2

CIS AND TRANS 4-(BROMOMETHYL)-2-ISOPROPOXY-1,3-DIOXOLANE

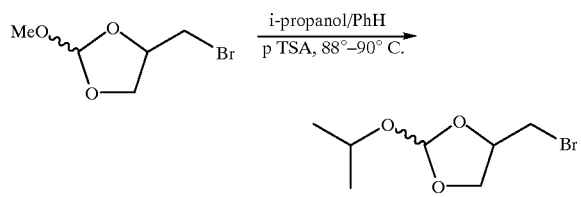

To a solution of cis and trans 4-(bromomethyl)-2-methoxy-1,3-dioxolane (example 1) (5.37 g, 27.3 mmol) in benzene (100 mL) was added isopropanol (2.2 mL, 28.6 mmol, 1.05 eq.) and p-toluenesulfonic acid (pTSA, few crystals). The mixture was stirred for 24 hr at 88°–90° C. followed by addition of isopropanol (0.5 mL, 0.24 eq.). The mixture was stirred for further 24 hr at 90° C., cooled to room temperature and benzene was removed under reduced pressure. The crude material was obtained in quantitative yield consisting of a mixture of isopropoxy and methoxy orthoesters in a 9:1 ratio respectively. The ratio of cis and trans isomers was about 1:1.

$^1$H NMR (300 MHz, CDCl$_3$) δ: 1.21 (d, 6H, CH(CH$_3$)$_2$), 3.45 (m, 2H, CH$_2$Br), 3.65 (m, 1H, CH(CH$_3$)$_2$), 3.92 (m, 1H, H-5a), 4.21 (m, 1H, H-5b), 4.42 and 4.55 (2m, 1H, H-4), 5.95 and 5.96 (2s, 1H, H-2).

Example 3

CIS AND TRANS 4-(BROMOMETHYL)-2-(DIISOPROPYLOXYPHOSPHINOYL)-1,3-DIOXOLANE

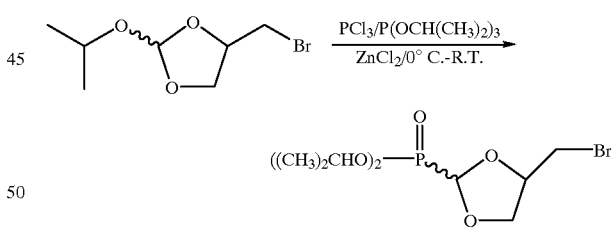

To the mixture of cis and trans 4-(bromomethyl)-2-isopropoxy-1,3-dioxolane (example 2) (6.13 g, 9:1 of isopropoxy:methoxy) was added triisopropyl phosphite (4.43 mL, 18.0 mmol, 0.66 eq.), phosphorus trichloride (0.784 mL, 8.99 mmol, 0.33 eq.) and zinc chloride (few milligrams) at 0° C. The mixture was stirred at 0° C. for 2 hr and at room temperature for 10 hr. The crude mixture of cis and trans isomers in a 2:5 ratio was purified by flash chromatography on silica gel using dichloromethane:ethyl acetate 4:1 as eluant to give the cis isomer (0.242 g), a mixture of cis and trans isomers (3.13 g) and the trans isomer (3.15 g) for a total yield of 72%. Several chromatographic purifications were performed to obtain the cis and trans isomers in pure form.

trans isomer:

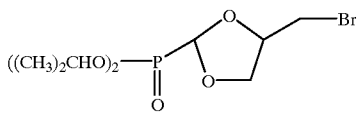

$^1$H NMR•(300 MHz, CDCl$_3$) δ: 1.36 (d, 12H, J=6.1 Hz, CH(CH$_3$)$_2$), 3.36 (dd, 1H, J=8.0 Hz, 10.2 Hz, C$\underline{H}_A$H$_B$Br), 3.48 (dd, 1H, J=4.4 Hz, 10.5 Hz, CH$_A\underline{H}_B$Br), 3.91 (dd, 1H, J=4.6 Hz, 8.0 Hz, H-5a), 4.39 (dd, 1H, J=6.3 Hz, 8.3 Hz, H-5b), 4.63 (m, 1H, H-4), 4.80 (m, 2H, CH(CH$_3$)$_2$), 5.32 (d, 1H, $^2$J$_{HP}$=30.4 Hz, H-2).

cis isomer:

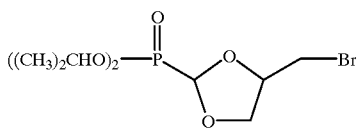

$^1$H NMR (300 MHz, CDCl$_3$) δ: 1.37 (d, 12H, J=6.1 Hz, CH(CH$_3$)$_2$), 3.50 (dd, 1H, J=8.9 Hz, 9.9 Hz, C$\underline{H}_A$H$_B$Br), 3.58 (dd, 1H, J=5.3 Hz, 9.9 Hz, CH$_A\underline{H}_B$Br), 4.14 (d, 2H, J=6.0 Hz, H-5), 4.41 (m, 1H, H-4), 4.80 (m, 2H, CH(CH$_3$)$_2$) and 5.18 (d, 1H, $^2$J$_{HP}$=29.6 Hz, H-2).

Example 4

CTS-4-(CYTOSIN-1'-YLMETHYL)-2-(DIISOPROPYLOXYPHOSPHINOYL)-1,3-DIOXOLANE

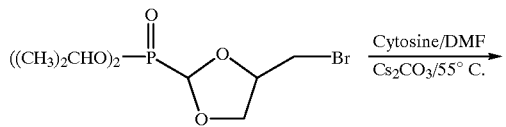

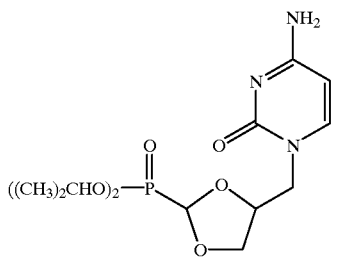

To a solution of cis-4-(bromomethyl)-2-(diisopropyloxyphosphinoyl)-1,3-dioxolane (example 3) (400 mg, 1.21 mmol) in DMF (30 mL) was added cytosine (148 mg, 1.33 mmol, 1.1 eq.), and Cs$_2$CO$_3$ (787 mg, 2.42 mmol, 2.0 eq.). The mixture was stirred at 55° C. for 72 hr, then cooled to room temperature and filtered. The filtrate was evaporated to dryness and the residue was purified on silica gel using dichloromethane:methanol 4:1 as eluant to give the desired product (135 mg) as an oil in 31% yield.

$^1$H NMR (300 MHz, CDCl$_3$) δ: 1.37 (d, 12H, J=6.1 Hz, 2 CH(CH$_3$)$_2$), 3.72 (dd, 1H, J=9.9 Hz, 13.7 Hz, C$\underline{H}_A$H$_B$N), 4.02 (d, 2H, J=5.5 Hz, H-5), 4.25 (dd, 1H, J=2.3 Hz, 13.6 Hz, CH$_A\underline{H}_B$N), 4.68 (bs, 1H, H-4), 4.78 (m, 2H, CH(CH$_3$)$_2$), 5.09 (d, 1H, $^2$J$_{HP}$=30.1 Hz, H-2), 5.81 (d, 1H, J=7.2 Hz, H-5'), 6.65 (bs, 2H, NH$_2$) and 7.92 (d, 1H, J=7.2 Hz, H-6').

Example 5

CIS-4-(CYTOSIN-1'-YLMETHYL)-2-(DIHYDROXYPHOSPHINOYL)-1,3-DIOXOLANE

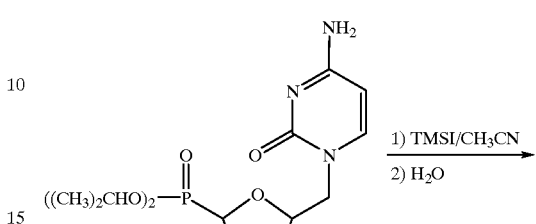

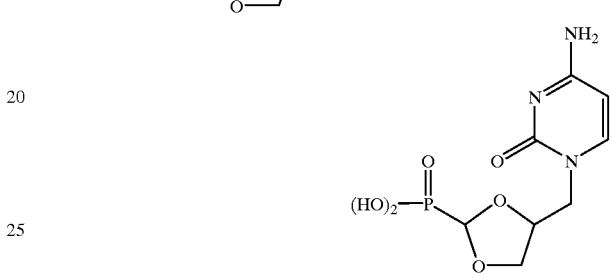

To a solution of cis-4-(cytosin-1'-ylmethyl)-2-(diisopropyloxyphosphinoyl)-1,3-dioxolane (example 4) (135 mg, 0.374 mmol) in CH$_3$CN (10 mL) was added trimethylsilyliodide (TMSI, 106 μL, 0.747 mmol, 2.0 eq.) at 0° C. The reaction mixture was stirred at room temperature for 4 days with successive addition of TMSI in two portions of 10 μL (0,2 eq.) after 30 hr and 75 hr. The solvent was removed under reduced pressure. The residue was taken in water and stirred for 18 hr. Water was removed by evaporation and the compound was triturated out upon the addition of methanol and ethyl acetate. The crude solid material (40 mg) was purified by reverse phase HPLC to give the desired product (19 mg) as a pale pink solid in 18% yield.

M.p. >210° C. (dec); UV λ$_{max}$ (H$_2$O): 273 nm;

$^1$H NMR (300 MHz, D$_2$O) δ: 3.64 (dd, 1H, J=8.7 Hz, 14.4 Hz, C$\underline{H}_A$H$_B$N), 3.80 (dd, 1H, J=4.7 Hz, 8.9 Hz, H-5a), 3.92 (dd, 1H, J=6.6 Hz, 8.8 Hz, H-5b), 4.06 (dd, 1H, J=2.9 Hz, 14.2 Hz, CH$_A\underline{H}_B$N), 4.36 (m, 1H, H-4), 4.83 (d, 1H, $^2$J$_{HP}$=23.1 Hz, H-2), 5.93 (d, 1H, J=7.7 Hz, H-5') and 7.75 (d, 1H, J=7.7 Hz, H-6').

Example 6

TRANS-4-(CYTOSIN-1'-YLMETHYL)-2-(DIISOPROPYLOXYPHOSPHINOYL)-1,3-DIOXOLANE

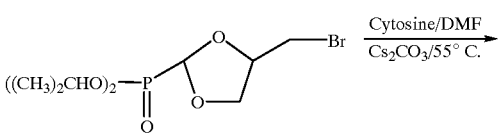

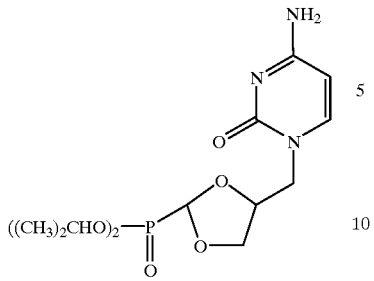

To a solution of trans-4-(bromomethyl)-2-(diisopropyloxyphosphinoyl)-1,3-dioxolane (example 3) (600 mg, 1.81 mmol) in DMF (50 mL) was added cytosine (221 mg, 1.99 mmol, 1.1 eq.) and Cs$_2$CO$_3$ (1.18 g, 3.62 mmol, 2.0 eq.). The mixture was stirred at 55° C. for 72 hr, then cooled to room temperature and filtered. The filtrate was evaporated to dryness under reduced pressure and the residue was purified by flash chromatography on silica gel using dichloromethane:methanol 75:25 as eluant to give the desired product (269 mg) as a foam in 41% yield.

$^1$H NMR (300 MHz, CDCl$_3$) δ: 1.32 (d, 12H, J=5.5 Hz, CH(CH$_3$)$_2$), 3.77 (dd, 1H, J=5.9 Hz, 8.4 Hz, H-5a), 3.86 (dd, 1H, J=6.6 Hz, 14.3 Hz, CH$_A$H$_B$N), 4.10 (dd, 1H, J=2.5 Hz, 14.6 Hz, CH$_A$H$_B$N), 4.30 (dd, 1H, J=6.6 Hz, 8.2 Hz, H-5b), 4.65 (m, 1H, H-4), 4.75 (m, 2H, CH(CH$_3$)$_2$), 5.22 (d, 1H, $^2$J$_{HP}$=30.7 Hz, H-2), 5.88 (d, 1H, J=7.2 Hz, H-5'), 6.9 (bs, 2H, NH$_2$) and 7.37 (d, 1H, J=7.2 Hz, H-6').

Example 7

TRANS-4-(CYTOSIN-1'-YLMETHYL)-2-(DIHYDROXYPHOSPHINOYL)-1,3-DIOXOLANE

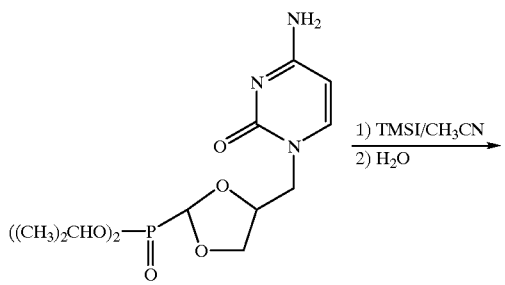

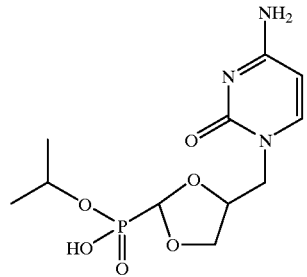

To a solution of trans-4-(cytosin-1'-ylmethyl)-2-(diisopropyloxyphosphinoyl)-1,3-dioxolane (example 6) (269 mg, 0.744 mmol) in CH$_3$CN (20 mL) was added trimethylsilyliodide (212 μL, 1.49 mmol, 2.0 eq.) at 0° C. The reaction mixture was stirred at room temperature for 4 days with successive additions of TMSI in two portions of 20 μL (0,2 eq.) after 30 hr and 75 hr. The solvent was removed under reduced pressure. The residue was taken in water and was stirred for 18 hr. Water was evaporated in vacuo and the product was triturated out upon the addition of methanol and ethyl acetate. This material was then treated again under the same condition using TMSI (318 μL, 3 eq.) in CH$_3$CN:DMF (20 mL:30 mL) for 4 days, and then quenched with water. After removal of water, the residue was crystallized from methanol and dichloromethane and consisted of a mixture of the desired compound and its monoisopropyl derivative in a 1:1 ratio. Further purification on reverse phase HPLC gave the fully deprotected desired product (55 mg) as a white solid in 27% yield.

M.p. >235° C. (dec); UV λ$_{max}$ (H$_2$O): 272 nm; $^1$H NMR (300 MHz, D$_2$O) δ: 3.55 (dd, 1H, J=5.7 Hz, 5.7 Hz, H-5a), 3.75 (dd, 1H, J=7.2 Hz, 14.5 Hz, CH$_A$H$_B$N), 3.87 (d, 1H, J=14.5 Hz, CH$_A$H$_B$N), 4.05 (dd, 1H, J=6.5 Hz, 8.5 Hz, H-5b), 4.36 (m, 1H, H-4), 4.88 (d, 1H, $^2$J$_{HP}$=22.8 Hz, H-2), 5.83 (d, 1H, J=7.4 Hz, H-5') and 7.49 (d, 1H, J=7.4 Hz, H-6');

$^{13}$C NMR (75.46 MHz, D$_2$O) δ: 57.2 (CH$_2$N), 74.6 (d, $^3$J$_{COCP}$=5.5 Hz, C-5), 81.8 (d, $^3$J$_{COCP}$=5.3 Hz, C-4), 102.6 (C-5'), 107.7 (d, $^1$J$_{CP}$=184 Hz, C-2), 154.8 (C-6') 165 (C-2') and 173 (C-4').

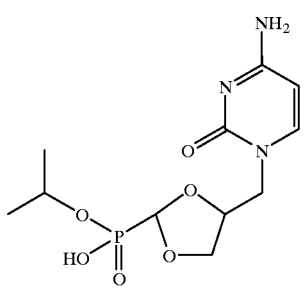

M.p. >180° C. (dec); UV $\lambda_{max}$ (H$_2$O): 272 nm; $^1$H NMR (300 MHz, D$_2$O) δ: 1.06 (d, 6H, J=6.2 Hz, CH(CH$_3$)$_2$), 3.59 (dd, 1H, J=5.6 Hz, 8.7 Hz, H-5a), 3.78 (dd, 1H, J=7.7 Hz, 14.5 Hz, C$\underline{H}_A$H$_B$N), 3.93 (dd, 1H, J=3.0 Hz, 14.5 Hz, CH$_A$ $\underline{H}_B$N), 4.08 (dd, 1H, J=6.3 Hz, 8.5 Hz, H-5b), 4.34 (m, 1H, H-4), 4.39 (m, 1H, CH(CH$_3$)$_2$), 4.94 (d, 1H, $^2$J$_{HP}$=24.6 Hz, H-2), 5.92 (d, 1H, J=7.5 Hz, H-5') and 7.61 (d, 1H, J=7.6 Hz, H-6').

Example 8

CIS-4-(ADENIN-9'-YLMETHYL)-2-(DIISOPROPYLOXYPHOSPHINOYL)-1,3-DIOXOLANE

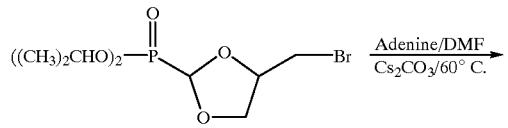

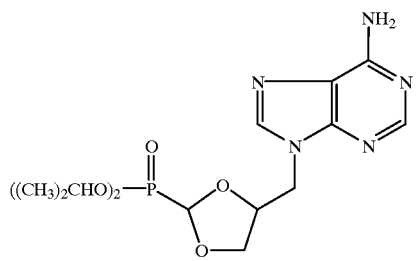

To a solution of cis-4-(bromomethyl)-2-(diisopropyloxyphosphinoyl)-1,3-dioxolane (example 3) (400 mg, 1.21 mmol) in DMF (30 mL) was added adenine (180 mg, 1.33 mmol, 1.1 eq.) and Cs$_2$CO$_3$ (787 mg, 2.42 mmol, 2.0 eq.). The mixture was stirred at 60° C. for 54 hr, cooled to room temperature and filtered. The filtrate was evaporated to dryness under reduced pressure and the residue was purified by flash chromatography on silica gel using dichloromethane:methanol 85:15 as eluant to give the desired compound (174 mg) as a foam in 37% yield.

$^1$H NMR (300 MHz, CDCl$_3$) δ: 1.38 (d, 12H, J=6.1 Hz, CH(CH$_3$)$_2$), 4.12 (m, 2H, H-5), 4.43 (dd, 1H, J=3.0 Hz, 14.0 Hz, C$\underline{H}_A$H$_B$N), 4.55 (dd, 1H, J=9.2 Hz, 13.9 Hz, CH$_A$$\underline{H}_B$N), 4.67 (m, 1H, H-4), 4.83 (m, 2H, CH(CH$_3$)$_2$), 5.14 (d, 1H, $^2$J$_{HP}$=29.8 Hz, H-2), 6.30 (bs, 2H, NH$_2$), 8.30 (s, 1H, H-2') and 8.34 (s, 1H, H-8').

Example 9

CIS-4-(ADENIN-9'-YLMETHYL)-2-(DIHYDROXYPHOSPHINOYL)-1,3-DIOXOLANE

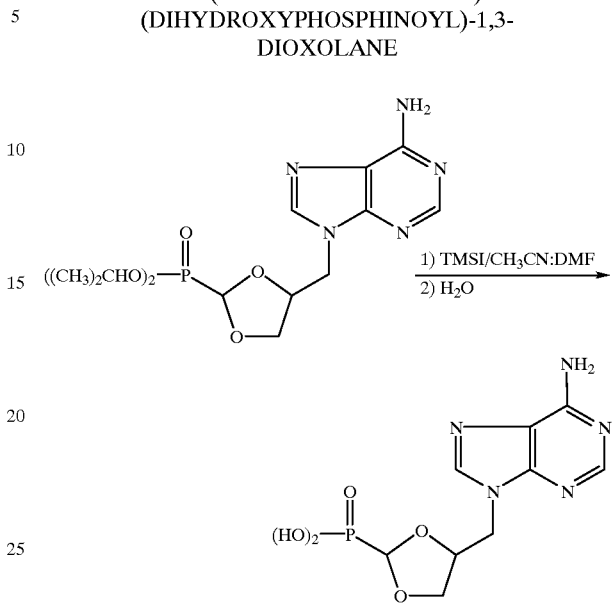

To a solution of cis-4-(adenin-9'-ylmethyl)-2-(diisopropyloxyphosphinoyl)-1,3-dioxolane (example 8) (174 mg, 0.452 mmol) in CH$_3$CN (20 mL,) and DMF (5 mL) was added trimethylsilyliodide (193 μL, 1.35 mmol, 3.0 eq.) at 0° C. The reaction mixture was stirred at room temperature for a week and successive additions of trimethylsilyliodide after 39 hr (150 μL, 1.05 mmol) and 64 hr (125 μL, 0.878 mmol), for a total of 7.3 eq. The solvent was removed under reduced pressure and the residue was dissolved in water. The mixture was stirred for 12hr, followed by removal of water. The product was triturated out upon the addition of dichloromethane and ether. The crude solid material was further purified by reverse phase HPLC to give the desired product (36.5 mg) as a white solid in 27% yield.

MP >230° C. (dec); UV $\lambda_{max}$ (H$_2$O): 261 nm; $^1$H NMR (300 MHz, D$_2$O) δ: 3.87 (dd, 1H, J=4.4 Hz, 8.8 Hz, H-5a), 3.95 (dd, 1H, J=6.7 Hz, 8.8 Hz, H-5b), 4.30 (dd, 1H, J=8.3 Hz, 14.9 Hz, C$\underline{H}_A$H$_B$N), 4.45 (d, 1H, J=14.9 Hz, CH$_A$$\underline{H}_B$N), 4.47 (m, 1H, H-4), 4.82 (d, 1H, $^2$J$_{HP}$=22.8 Hz, H-2), 8.29 (s, H, H-2') and 8.32 (s, H, H-8').

Example 10

TRANS-4-(ADENIN-9'-YLMETHYL)-2-(DIISOPROPYLOXYPHOSPHINOYL)-1,3-DIOXOLANE

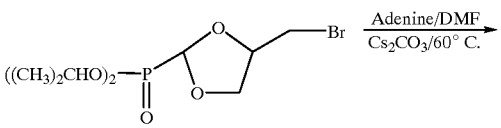

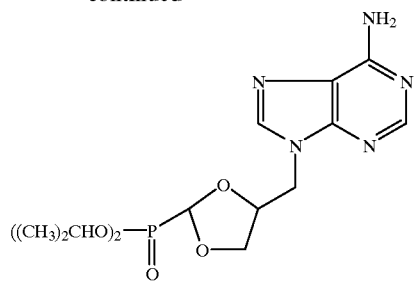

To a solution of trans-4-(bromomethyl)-2-(diisopropyloxyphosphinoyl)-1,3-dioxolane (example 3) (600 mg, 1.81 mmol) in DMF (50 mL) was added adenine (269 mg, 1.99 mmol, 1.1 eq.) and Cs$_2$CO$_3$ (1.18 g, 3.62 mmol, 2.0 eq.) and the mixture was stirred at 60° C. for 54 hr. The solution was cooled to room temperature, filtered and the solvent was removed under reduced pressure. The residue was purified by flash chromatography on silica gel using dichloromethane:methanol 85:15 as eluant to give the desired compound (339 mg) as a foam in 49% yield.

$^1$H NMR (300 MHz, CDCl$_3$) δ: 1.33 (d, 12H, J=6.2 Hz, CH(CH$_3$)$_2$), 3.77 (dd, 1H, J=5.3 Hz, 8.3 Hz, H-5a), 4.40 (m, 3H, CH$_2$N and H-5b), 4.75 (m, 3H, H-4 and CH(CH$_3$)$_2$), 5.24 (d, 1H, $^2$J$_{HP}$=29.7 Hz, H-2), 6.06 (bs, 2H, NH$_2$), 7.95 (s, 1H, H-2') and 8.35 (s, 1H, H-8').

Example 11

TRANS-4-(ADENIN-9'-YLMETHYL)-2-(DIHYDROXYPHOSPHINOYL)-1,3-DIOXOLANE

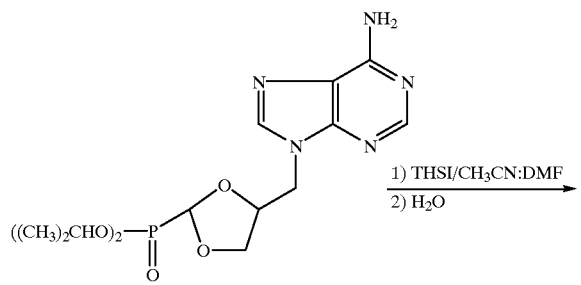

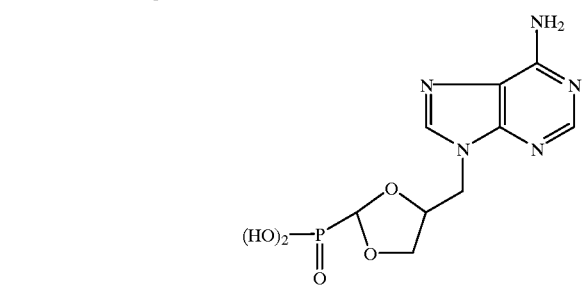

To a solution of trans-4-(adenin-9'-ylmethyl)-2-(diisopropyloxyphosphinoyl)-1,3-dioxolane (example 10) (339 mg, 0.880 mmol) in CH$_3$CN (40 mL) and DMF (10 mL) was added trimethylsilyliodide (375 μL, 2.64 mmol, 3.0 eq.) at 0° C. The reaction mixture was stirred at room temperature for a week with successive additions of trimethylsilyliodide after 39 hr (300 μL, 2.11 mmol) and 64 hr (250 μL (1.76 mmol), for a total of 7.4 eq. The solvents were removed under reduced pressure, the residue was dissolved in water and the mixture was stirred for12 hr. After removal of water the residue was dissolved in methanol and triturated out upon additions of acetone, dichloromethane and ether. The crude solid material (468 mg) was further purified by reverse phase HPLC to give the desired product (200.5 mg) as a white solid in 76% yield.

M.p. >240° C. (dec); UV λ$_{max}$ (H$_2$O): 258 nm; $^1$H-NMR (300 MHz, D$_2$O) δ: 3.69 (dd, 1H, J=5.1 Hz, 8.8 Hz, H-5a), 4.14 (dd, 1H, J=6.4 Hz, 8.8 Hz, H-5b), 4.36 (dd, 1H, J=6.8 Hz, 14.5 Hz, CH$_A$H$_B$N), 4.41 (dd, 1H, J=3.5 Hz, 14.5 Hz, CH$_A$H$_B$N), 4.56 (m, 1H, H-4), 4.92 (d, 1H, $^2$J$_{HP}$=24.2 Hz, H-2) and 8.28 (s, 2H, H-2' and H-8').

Example 12

CIS-4-(2'-AMINO-6'-CHLOROPURIN-9'-YLMETHYL)-2-(DIISOPROPYLOXYPHOSPHINOYL)-1,3-DIOXOLANE

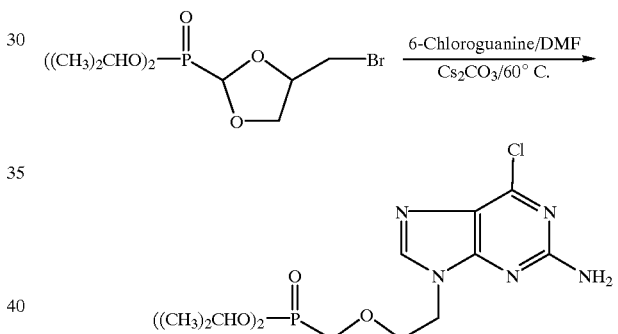

To a solution of cis-4-(bromomethyl)-2-(diisopropyloxyphosphinoyl)-1,3-dioxolane (example 3) (819 mg, 2.47 mmol) in DMF (75 mL) was added 6-chloroguanine (478 mg, 2.82 mmol, 1.1 eq.) and Cs$_2$CO$_3$ (1.66 g, 5.09 mmol, 2.1 eq.) and the mixture was stirred at 60° C. for 65 hr. The solution was cooled to room temperature, filtered and the solvent was removed under reduced pressure. The residue was purified by flash chromatography on silica gel using dichloromethane:methanol 93:7 as eluant to give the desired compound (310 mg) as a foam in 30% yield.

$^1$H NMR (300 MHz, CDCl$_3$) δ: 1.37 (d, 12H, J=6.1 Hz, CH(CH$_3$)$_2$), 4.11 (m, 2H, H-5), 4.28 (dd, 1H, J=3.0 Hz, 14.1 Hz, CH$_A$H$_B$N), 4.44 (dd, 1H, J=9.4 Hz, 14.1 Hz, CH$_A$H$_B$N), 4.63 (m, 1H, H-4), 4.81 (m, 2H, CH(CH$_3$)$_2$), 5.15 (bs, 2H, NH$_2$), 5.14 (d, 1H, $^2$J$_{HP}$=29.7 Hz, H-2) and 8.16 (s, 1H, H-8').

Example 13

CIS-2-(DIHYDROXYPHOSPHINOYL)-4-(GUANIN-9'-YLMETHYL)-1,3-DIOXOLANE (BCH-1299)

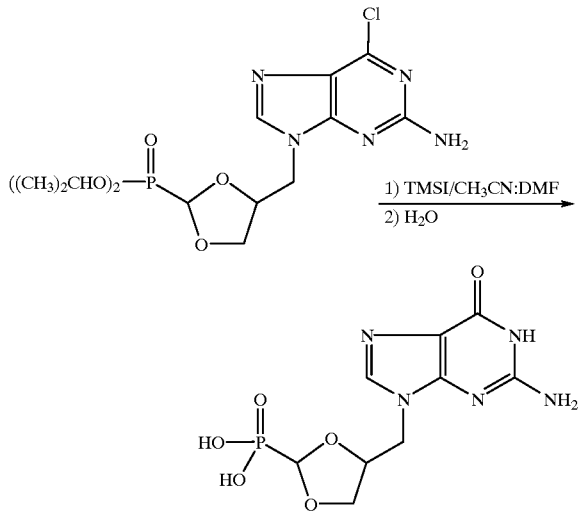

To a solution of cis-4-(2'-amino-6'-chloropurin-9'-ylmethyl)-2-(diisopropyloxyphosphinoyl)-1,3-dioxolane (example 12) (310 mg, 0.738 mmol) in CH$_3$CN (20 mL) and DMF (5 mL) was added trimethylsilyliodide (1050 μL, 7.38 mmol, 10.0 eq.) at 0° C. The reaction mixture was stirred at room temperature for 3 days and solvents were removed under reduced pressure. The residue was dissolved in water and the mixture was stirred for 24 hr. After removal of water the residue was dissolved in methanol-acetone and the product was triturated out upon addition of ether. This crude material (120 mg out of 397 mg) was further purified on reverse phase HPLC to give the desired product (37.5 mg) as a white solid in 16% yield M.p.: >260° C.; UV λ$_{max}$ (H$_2$O): 252 and 272 nm $^1$H NMR (300 MHz, D$_2$O) δ: 3.88 (dd, 1H, J=4.4 Hz, 9.1 Hz, H-5a), 3.93 (dd, 1H, J=6.4 Hz, 9.1 Hz, H-5b), 4.17 (dd, 1H, J=7.9 Hz, 14.5 Hz, CH$_A$H$_B$N), 4.34 (dd, 1H, J=3.0 Hz, 14.5 Hz, CH$_A$H$_B$N), 4.46 (m, 1H, H-4), 4.82 (d, 1H, $^2$J$_{HP}$=22.8 Hz, H-2) and 8.66 (s, 1H, H-8').

Example 14

TRANS-4-(2'-AMINO-6'-CHLOROPURIN-9'-YLMETHYL)-2-(DIISOPROPYLOXYPHOSPHINOYL)-1,3-DIOXOLANE

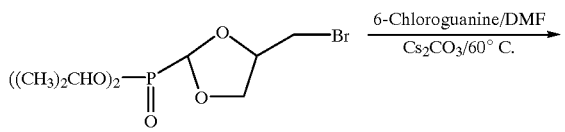

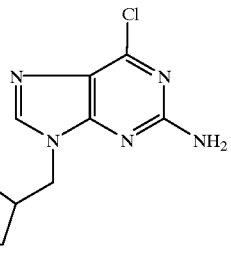

To a solution of trans-4-(bromomethyl)-2-(diisopropyloxyphosphinoyl)-1,3-dioxolane (example 3) (2.50 g, 7.55 mmol) in DMF (180 mL) was added 6-chloro-2-aminopurine (1.41 g, 8.31 mmol, 1.1 eq.) and Cs$_2$CO$_3$ (4.90 g, 15.0 mmol, 2.0 eq.) and the mixture was stirred at 60° C. for 65 hr. The solution was cooled to room temperature, filtered and the solvent was removed under reduced pressure. The residue was purified by flash chromatography on silica gel using dichloromethane:methanol 93:7 as eluant to give the product (1.874 g) as a foam in 59% yield.

$^1$H NMR (300 MHz, CDCl$_3$) δ: 1.32 (2d, 12H, J=6.1 Hz, CH(CH$_3$)$_2$), 3.77 (dd, 1H, J=5.2 Hz, 8.1 Hz, H-5a), 4.24 (dd, 1H, J=5.6 Hz, 14.7 Hz, CH$_A$H$_B$N), 4.32 (dd, 1H, J=3.6 Hz, 14.8 Hz, CH$_A$H$_B$N), 4.37 (dd, 1H, J=6.7 Hz, 8.3 Hz, H-5b), 4.76 (m, 3H, H-4 and CH(CH$_3$)$_2$), 5.12 (bs, 2H, NH$_2$), 5.24 (d, 1H, $^2$J$_{HP}$=29.4 Hz, H-2) and 7.88 (s, 1H, H-8').

Example 15

TRANS-2-(DIHYDROXYPHOSPHINOYL)-4-(GUANIN-9'-YLMETHYL)-1,3-DIOXOLANE, MONOAMMONIUM SALT

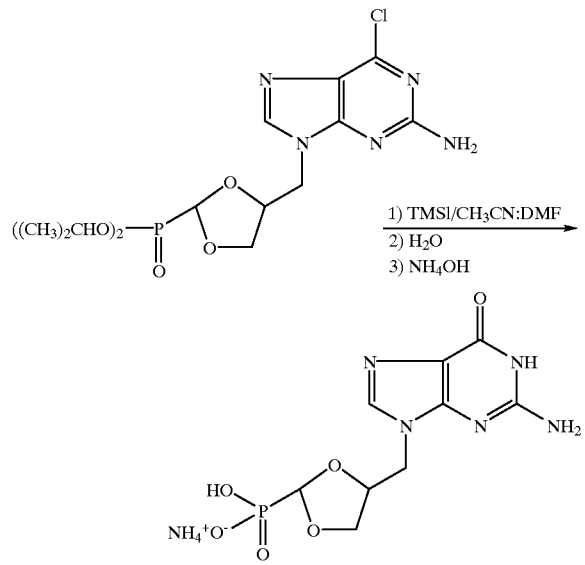

To a solution of trans-4-(2'-amino-6'-chloropurin-9'-ylmethyl)-2-(diisopropyloxyphosphinoyl)-1,3-dioxolane (example 14) (818 mg, 1.95 mmol) in CH$_3$CN (40 mL) and DMF (10 mL) was added trimethylsilyliodide (2.25 mL, 15.8 mmol, 8.1 eq.) at 0° C. The reaction mixture was stirred at room temperature for 3 days and the solvents were removed under reduced pressure. The residue was dissolved in water, stirred for 24 hr and water was removed under reduced pressure. The residue was dissolved in methanol and the product was precipitated out by adding acetone and ether. A part of this crude material (450 mg out of 1.041 g) was dissolved in water, poured on a SEPHADEX (microscopic polysaccharide dextran derivative beads) DEAE A-25 column and eluted with a gradient of 0 to 0.3 M of NH$_4$HCO$_3$ solution (1L), and with 0.3 M of NH$_4$HCO$_3$ solution (100 mL) to give the desired product (100 mg) as ammonium salt.

UV $\lambda_{max}$ (H$_2$O): 251.8 and 270.0 nm $^1$H NMR (300 MHz, DMSO) δ: 3.58 (dd, 1H, J=5.4 Hz, 7.5 Hz, H-5a), 4.05 (m, 3H, H-5b, CH$_2$N), 4.51 (m, 1H, H-4), 4.93 (d, 1H, $^2$J$_{HP}$=22.0 Hz, H-2), 6.54 (s, 2H, NH$_2$), 7.26 (bs, 4H, NH$_4$) and 7.66 (s, 1H, H-8').

Example 16

CIS-2-(DIISOPROPYLOXYPHOSPHINOYL)-4-(URACIL-1'-YLMETHYL)-1,3-DIOXOLANE

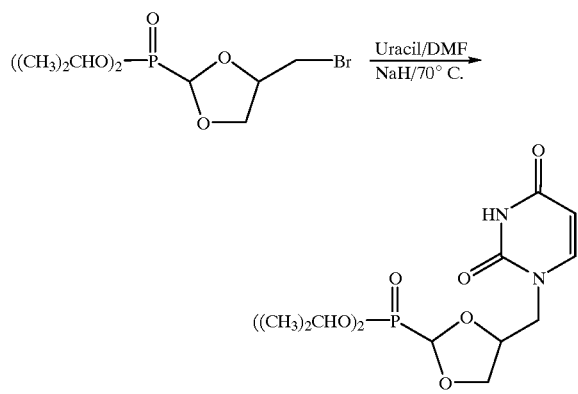

To a solution of uracil (223 mg, 1.99 mmol, 1.1 eq) in DMF (15 mL) was added sodium hydride (80 mg of a 60% dispersion in oil, 1.99 mmol, 1.1 eq) and the mixture was stirred at room temperature for 1 hr. Then a solution of cis-4-(bromomethyl)-2-(diisopropyloxyphosphinoyl)-1,3-dioxolane (600 mg, 1.81 mmol) (example 3) in DMF (15 mL) was added. The mixture was stirred at 70° C. for 48 hr. The solution was cooled to room temperature, and the solvent was evaporated. A saturated solution of ammonium chloride was added and the aqueous phase was extracted with dichloromethane. The organic layer was dried over anhydrous sodium sulphate and evaporated under reduced pressure. The crude material was purified by flash chromatography with a mixture of ethylacetate and methanol (95:5) to give the pure compound (97 mg) in 15% yield.

$^1$H NMR (300 MHz, CDCl$_3$) δ: 1.35 (2d, 12H, J=5.5 Hz, CH(CH$_3$)$_2$), 3.71 (dd, 1H, J=10.2 Hz, 13.8 Hz, CH$_A$H$_B$N), 4.03 (d, 2H, J=5.8 Hz, H-5), 4.17 (dd, 1H, J=2.3 Hz, 13.8 Hz, CH$_A$H$_B$N), 4.63 (m, 1H, H-4), 4.77 (m, 2H, CH(CH$_3$)$_2$), 5.10 (d, 1H, $^2$J$_{HP}$=29.9 Hz, H-2), 5.63 (dd, 1H, J=2.2 Hz, 7.9 Hz, H-5'), 7.90 (d, 1H, J=7.9 Hz, H-6') and 9.40 (bs, 1H, NH).

Example 17

CIS-2-(DIHYDROXYPHOSPHINOYL)-4-(URACIL-1'-YLMETHYL)-1,3-DIOXOLANE, MONOAMMONIUM SALT

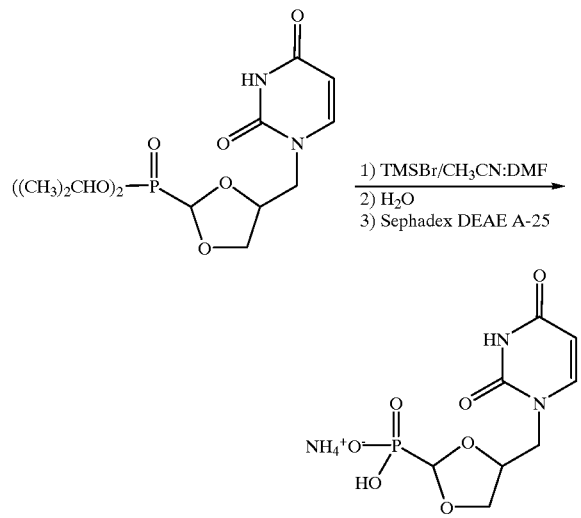

To a solution of cis-2-(diisopropyloxyphosphinoyl)-4-luracil-1'-ylmethyl)-1,3-dioxolane (example 16) (97 mg, 0.268 mmol) in CH$_3$CN (8 mL) and DMF (2 mL) was added trimethylsilylbromide (800 µL, 6.06 mmol, 23 eq.) at 0° C. The reaction mixture was stirred at R.T. for 2 days and the solvents were evaporated to dryness. Water and ammonium hydroxide were added and the mixture was stirred for 5 hr; then water was evaporated to get a solid. The crude compound was dissolved in water and poured on a SEPHADEX (microscopic polysaccharide dextran derivative beads) DEAE A-25 column and eluted with a gradient of 0 to 0.2 M of NH$_4$HCO$_3$ (500 mL of water and 500 mL of 0.2 M NH$_4$HCO$_3$). The appropriate fractions were evaporated to give 110 mg of a white solid, which was purified by reverse phase HPLC to remove the excess of NH$_4$HCO$_3$ and the pure compound was obtained in 58% yield (45.5 mg).

$^1$H NMR (300 MHz, DMSO) δ: 3.75 (m, 2H, H-5a and C H$_A$H$_B$N), 3.88 (dd, 1H, J=3.2 Hz, 8.3 Hz, H-5b), 3.94 (dd, 1H, J=2.6 Hz, 13.5 Hz, CH$_A$H$_B$N), 4.17 (m, 1H, H-4), 4.74 (d, 1H, $^2$J$_{HP}$=20.5 Hz, H-2), 5.45 (d, 1H, J=7.8 Hz, H-5') and 8.27 (d, 1H, J=7.8 Hz, H-6'). UV $\lambda_{max}$ (H$_2$O): 264.4 nm.

Example 18

TRANS-2-(DIISOPROPYLOXYPHOSPHINOYL)-4-(URACIL-1'-YLMETHYL)-1,3-DIOXOLANE

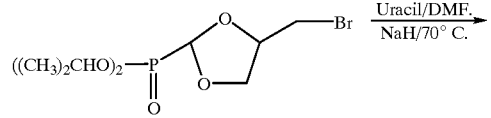

-continued

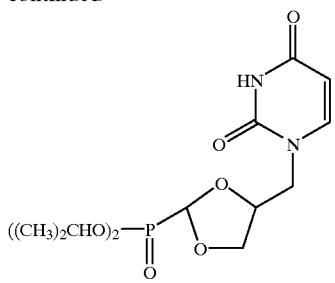

To a solution of uracil (223 mg, 1.99 mmol, 1.1 eq) in DMF (15 mL) was added sodium hydride (80 mg of a 60% dispersion in oil, 1.99 mmol, 1.1 eq) and the mixture was stirred at room temperature for 1 hr. Then a solution of trans-4-(bromomethyl)-2-(diisopropyloxyphosphinoyl)-1,3-dioxolane (example 3) (600 mg, 1.81 mmol) in DMF (15 mL) was added. The mixture was stirred at 70° C. for 48 hr. The solution was cooled to room temperature, and the solvent was evaporated. A saturated solution of ammonium chloride was added and the aqueous phase was extracted with dichloromethane. The organic layer was dried over anhydrous sodium sulphate and evaporated under reduced pressure. The crude material was purified by flash chromatography with a mixture of ethylacetate and methanol (95:5) to give the pure compound (114 mg) in 17% yield.

$^1$H NMR (300 MHz, CDCl$_3$) δ: 1.33 (2d, 12H, J=5.5 Hz, CH(CH$_3$)$_2$), 3.79 (dd, 1H, J=5.5 Hz, 8.5 Hz, H-5a), 3.86 (dd, 1H, J=6.3 Hz, 14.6 Hz, CH$_A$H$_B$N), 4.02 (dd, 1H, J=3.0 Hz, 14.6 Hz, CH$_A$H$_B$N), 4.36 (dd, 1H, J=6.6 Hz, 8.5 Hz, H-5b), 4.66 (m, 1H, H-4), 4.75 (m, 2H, CH(CH$_3$)$_2$), 5.25 (d, 1H, $^2$J$_{HP}$=29.7 Hz, H-2), 5.70 (dd, 1H, J=2.4 Hz, 8.0 Hz, H-5'), 7.29 (d, 1H, J=8.0 Hz, H-6') and 8.95 (bs, 1H, NH).

Example 19

TRANS-2-(DIHYDROXYPHOSPHINOYL)-4-(URACIL-1'-YLMETHYL)-1,3-DIOXOLANE, MONOAMMONIUM SALT

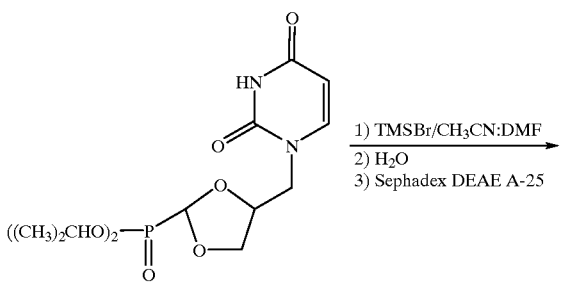

To a solution of trans-2-(diisopropyloxyphosphinoyl)-4-(uracil-1'-ylmethyl)-1,3-dioxolane (example 18) (114 mg, 0.315 mmol) in CH$_3$CN (8 mL) and DMF (2 mL) was added trimethylsilylbromide (800 μL, 6.06 mmol, 19 eq.) at 0° C. The reaction mixture was stirred at R.T. for 2 days and the solvents were evaporated to dryness. Water and ammonium hydroxide were added and the mixture was stirred for 5 hr; then water was evaporated to get a solid. The crude compound was dissolved in water and poured on a SEPHADEX (microscopic polysaccharide dextran derivative beads) DEAE A-25 column and eluted with a gradient of 0 to 0.3 M of NH$_4$HCO$_3$ (500 mL of water and 500 mL of 0,3 M NH$_4$HCO$_3$). The appropriate fractions were evaporated to give 70 mg of a white solid, which was purified by reverse phase HPLC to remove the excess of NH$_4$HCO$_3$ and the pure compound was obtained in 61% yield (56.6 mg).

$^1$H NMR (300 MHz, DMSO) δ: 3.49 (dd, 1H, J=5.1 Hz, 7.8 Hz, H-5a), 3.68 (dd, 1H, J=7.5 Hz, 14.2 Hz, CH$_A$H$_B$N), 3.84 (dd, 1H, J=3.6 Hz, 14.2 Hz, CH$_A$H$_B$N), 4.08 (dd, 1H, J=6.9 Hz, 7.8 Hz, H-5b), 4.35 (m, 1H, H-4), 4.85 (d, 1H, $^2$J$_{HP}$=19.9 Hz, H-2), 5.54 (d, 1H, J=7.9 Hz, H-5') and 7.58 (d, 1H, J=7.9 Hz, H-6').

$^{13}$C NMR (75.46 MHz, DMSO) δ: 49.6 (CH$_2$N), 67.1 (C-5), 73.6 (C-4), 100.9 (C-5'), 103.1 (d, $^1$J$_{CP}$=182 Hz, C-2), 146.8 (C-6'), 151.5 (C-2') and 164.1 (C-4'). UV λ$_{max}$ (H$_2$O): 264.9 nm.

Example 20

CIS-2-(DIISOPROPYLOXYPHOSPHINOYL)-4-(THYMIN-1'-YLMETHYL)-1,3-DIOXOLANE

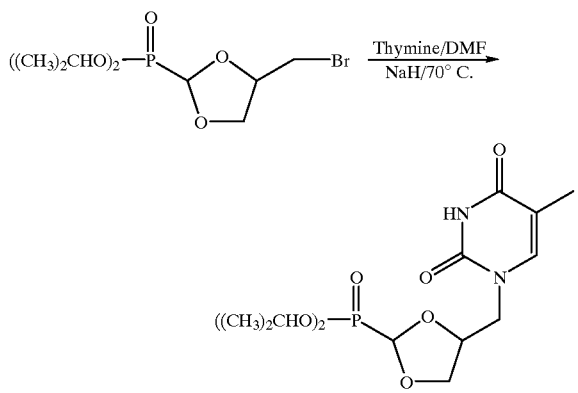

To a solution of thymine (209 mg, 1.66 mmol, 1.1 eq) in DMF (10 mL) was added sodium hydride (66 mg of a 60% dispersion in oil, 1.66 mmol, 1.1 eq) and the mixture was stirred at room temperature for 2 hr. Then a solution of cis-4-(bromomethyl)-2-(diisopropyloxyphosphinoyl)-1,3-dioxolane (example 3) (502 mg, 1.52 mmol) in DMF (10 mL) was added. The mixture was stirred at 70° C. for 72 hr. The solution was cooled to room temperature, and the solvent was evaporated. A saturated solution of sodium bicarbonate was added and the aqueous phase was extracted with dichloromethane. The organic layer was dried over anhydrous sodium sulphate and evaporated under reduced pressure. The crude material was purified by flash chromatography with a mixture of ethylacetate and methanol (95:5) to give the pure compound (78 mg) in 15% yield.

$^1$H NMR (300 MHz, CDCl$_3$) δ: 1.38 (2d, 12H, J=6.0 Hz, CH(CH$_3$)$_2$), 1.91 (s, 3H, CH$_3$), 3.69 (dd, 1H, J=10.1 Hz, 14.0 Hz, CH$_A$H$_B$N), 4.03 (d, 2H, J=5.7 Hz, H-5), 4.15 (dd, 1H, J=2.4 Hz, 13.9 Hz, CH$_A$H$_B$N), 4.63 (m, 1H, H-4), 4.79 (m, 2H, CH(CH$_3$)$_2$), 5.11 (d, 1H, $^2$J$_{HP}$=29.8 Hz, H-2), 7.71 (s, 1H, H-6') and 8.4 (bs, 1H, NH).

Example 21

CIS-2-(DIHYDROXYPHOSPHINOYL)-4-(THYMIN-1'-YLMETHYL)-1,3-DIOXOLANE, MONOAMMONIUM SALT

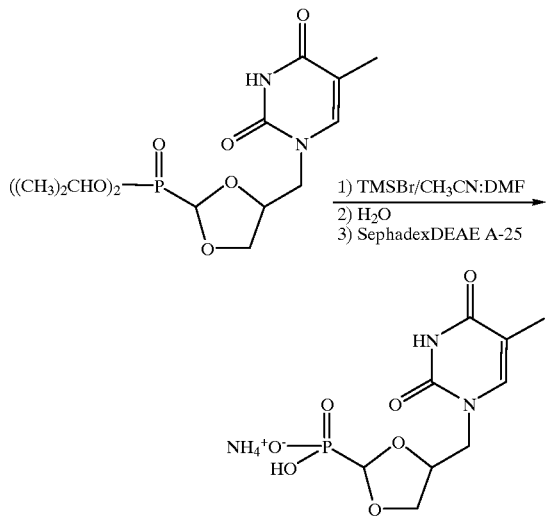

To a solution of cis-2-(diisopropyloxyphosphinoyl)-4-(thymin-1'-ylmethyl)-1,3-dioxolane (example 20) (77 mg, 0.205 mmol) in $CH_3CN$ (8 mL) and DMF (2 mL) was added trimethylsilylbromide (900 µL, 6.82 mmol, 33 eq.) at 0° C. The reaction mixture was stirred at R.T. for 4 days and the solvents were evaporated to dryness. Water and ammonium hydroxide were added and the mixture was stirred for a few hr; then water was evaporated to get a solid. The crude compound was dissolved in water and poured on a SEPHADEX (microscopic polysaccharide dextran derivative beads) DEAE A-25 column and eluted with a gradient of 0 to 0.2 M of $NH_4HCO_3$ (500 mL of water and 500 mL of 0,2 M $NH_4HCO_3$). The appropriate fractions were evaporated to give a white solid, which was purified by reverse phase HPLC to remove the excess of $NH_4HCO_3$ and the pure compound was obtained in 17% yield (11 mg).

$^1$H NMR (300 MHz, DMSO) δ: 1.73 (s, 3H, $CH_3$), 3.83 (m, 4H, $CH_2N$ and H-5), 4.16 (m, 1H, H-4), 4.74 (d, 1H, $^2J_{HP}$=20.0 Hz, H-2), and 8.13 (s, 1H, H-6'). UV $\lambda_{max}$ ($H_2O$): 270.2 nm.

Example 22

TRANS-2-(DIISOPROPYLOXYPHOSPHINOYL)-4-(THYMIN-1'-YLMETHYL)-1,3-DIOXOLANE

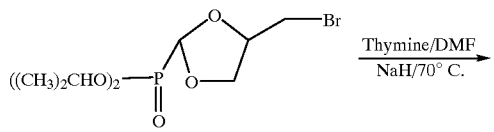

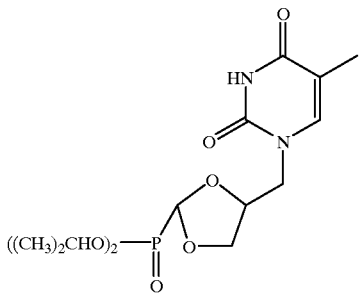

To a solution of thymine (251 mg, 1.99 mmol, 1.1 eq) in DMF (15 mL) was added sodium hydride (80 mg of a 60% dispersion in oil, 1.99 mmol, 1.1 eq) and the mixture was stirred at room temperature for 2 hr. Then a solution of trans-4-(bromomethyl)-2-(diisopropyloxyphosphinoyl)-1,3-dioxolane (example 3) (600 mg, 1.81 mmol) in DMF (10 mL) was added. The mixture was stirred at 70° C. for 72 hr. The solution was cooled to room temperature, and the solvent was evaporated. A saturated solution of ammonium chloride was added and the aqueous phase was extracted with dichloromethane. The organic layer was dried over anhydrous sodium sulphate and evaporated under reduced pressure. The crude material was purified by flash chromatography with a mixture of ethylacetate and methanol (95:5) to give the pure compound (99 mg) in 15% yield.

$^1$H NMR (300 MHz, $CDCl_3$) δ: 1.34 (2d, 12H, J=3.7 Hz, $CH(CH_3)_2$), 1.91 (s, 3H, $CH_3$), 3.80 (m, 2H, $CH_AH_BN$ and H-5a), 4.00 (dd, 1H, J=3.0 Hz, 14.6 Hz, $CH_AH_BN$), 4.34 (dd, 1H, J=6.6 Hz, 8.3 Hz, H-5b), 4.65 (m, 1H, H-4), 4.76 (m, 2H, $CH(CH_3)_2$), 5.25 (d, 1H, $^2J_{HP}$=30.0 Hz, H-2), 7.12 (s, 1H, H-6') and 9.13 (bs, 1H, NH).

Example 23

TRANS-2-(DIHYDROXYPHOSPHINOYL)-4-(THYMIN-1'-YLMETHYL)-1,3-DIOXOLANE, MONOAMMONIUM SALT

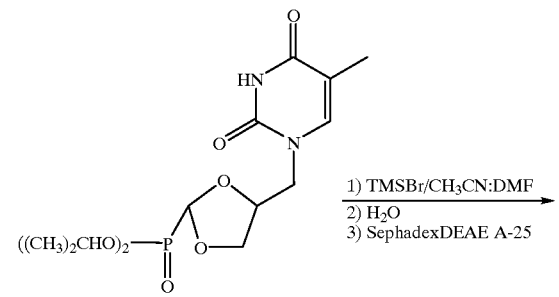

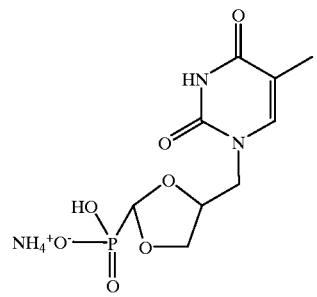

To a solution of trans-2-(diisopropyloxyphosphinoyl)-4-(thymin-1'-ylmethyl)-1,3-dioxolane (example 22) (99 mg, 0.263 mmol) in CH$_3$CN (8 mL) and DMF (2 mL) was added trimethylsilylbromide (800 μL, 6.06 mmol, 23 eq.) at 0° C. The reaction mixture was stirred at R.T. for 3 days and the solvents were evaporated to dryness. Water and ammonium hydroxide were added and the mixture was stirred for a few hr; then water was evaporated to get a solid. The crude compound was dissolved in water and poured on a SEPHADEX (microscopic polysaccharide dextran derivative beads) DEAE A-25 column and eluted with a gradient of 0 to 0,2 M of NH$_4$HCO$_3$ (500 mL of water and 500 mL of 0.2 M NH$_4$HCO$_3$). The appropriate fractions were evaporated to give 70 mg of a white solid, which was purified by reverse phase HPLC to remove the excess of NH$_4$HCO$_3$ and the pure compound was obtained in 31% yield (25.3 mg).

$^1$H NMR (300 MHz, DMSO) δ: 1.75 (s, 3H, CH$_3$), 3.50 (dd, 1H, J=5.1 Hz, 7.8 Hz, H-5a), 3.65 (dd, 1H, J=7.7 Hz, 14.1 Hz, C$\underline{H}_A$H$_B$N), 3.80 (dd, 1H, J=3.6 Hz, 14.0 Hz, CH$_A$$\underline{H}_B$N), 4.07 (dd, 1H, J=7.3 Hz, 7.3 Hz, H-5b), 4.36 (m, 1H, H-4), 4.88 (d, 1H, $^2$J$_{HP}$=20.6 Hz, H-2) and 7.47 (s, 1H, H-6'). UV λ$_{max}$ (H$_2$O): 270.4 nm.

Example 24

1-t-BUTYLDIPHENYLSILYLOXY-3-MERCAPTO-2-PROPANOL

To a solution of 3-mercapto-1,2-propanediol (5.00 g, 46.23 mmol) and imidazole (3.78 g, 55.47 mmol) in dimethylformamide (30 mL) was added t-butyldiphenylsilyl chloride (12.71 g, 46.23 mmol) at room temperature. After stirring for 18 h the reaction was quenched by the addition of saturated sodium bicarbonate and the mixture was extracted with ether (3x). The combined ether extracts were washed with water (2x), brine, dried and concentrated to give a yellow oil. The crude material was purified by flash chromatography with a mixture of hexanes and ethyl acetate (90:10) to give the compound as a colourless oil (14.12 g) in 88% yield.

$^1$H NMR (300 MHz, CDCl$_3$) d: 1.08 (s, 9H, t-butyl), 1.39 (t, 1H, J=9 Hz, SH), 1.95 (bs, 1H, OH), 2.68 (dd, 2H, J=9 Hz, 5.5 Hz, H-3), 3.72 (m, 3H, H-1 and H-2), 7.43 and 7.66 (m, 10H, Ar—H).

Example 25

CIS AND TRANS 5-(t-BUTYLDIPHENYLSILYLOXYMETHYL)-2-(DIETHYLOXYPHOSPHINOYL)-1,3-OXATHIOLANE

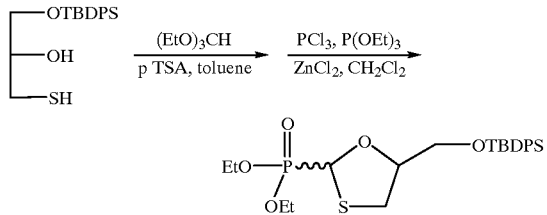

A solution of triethylorthoformate (0.64 g, 4.33 mmol), 1-t-butyldiphenylsilyloxy-3-mercapto-2-propanol (example 24) (5.00 g, 46.23 mmol) and p-toluenesulfonic acid (20 mg) in toluene (60 mL) was heated to reflux for 2 h. The solvent was removed under reduced pressure to give a yellow oil. The oil was dissolved in dichloromethane (20 mL), zinc chloride (20 mg) was added along with triethyl phosphite (0.32 g, 1.93 mmol) at 0° C., followed by the addition of phosphorous trichloride (0.13 g, 0.95 mmol). After stirring at room temperature for 18 h the solvent was removed under reduced pressure to give a colorless oil. The crude material was purified by flash chromatography with a mixture of hexanes and ethyl acetate (50:50) to give the compound as a colorless oil (0.97 g) in 67% yield as a mixture of cis and trans isomers (1:3.5).

$^1$H NMR (300 MHz, CDCl$_3$) d: 1.03 (s, 9H, t-butyl), 1.32 (t, 6H, J=7.0 Hz, CH$_3$), 3.02 (m, 1H, H-4a), 3.18 and 3.24 (2dd, 1H, J=10.0 Hz, 6.0 Hz, H-4b), 3.72 (m, 2H, CH$_2$OSi), 4.20 (m, 4H, C$\underline{H}_2$CH$_3$), 4.64 (p, 1H, J=6 Hz, H-5), 5.25 and 5.27 (2d, 1H, $^2$J$_{HP}$=9 Hz, H-2), 7.38 and 7.63 (m, 10H, Ar—H).

Example 26

TRANS-2-DIETHYLOXYPHOSPHINOYL-5-HYDROXYMETHYL-1,3-OXATHIOLANE

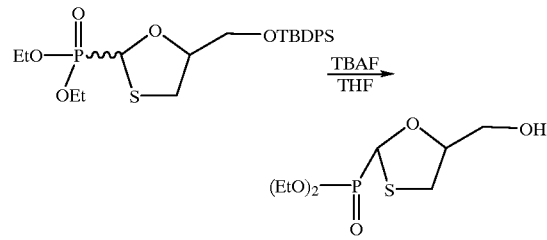

To a solution of cis and trans-5-t-butyldiphenylsilyloxymethyl-2-diethyloxyphosphinoyl-1,3-oxathiolane (example 25) (0.97 g, 1.94 mmol) in tetrahydrofuran (30 mL) was added a solution of tetrabutylammoniun fluoride (1.0 M in THF) (2.33 mL, 2.33 mmol). After stirring at room temperature for 18 hr the reaction was quenched by the addition of saturated ammonium chloride. The resulting mixture was extracted with ethyl acetate (3x), the combined organic extracts were washed with water, dried and concentrated to give a yellow oil. The crude material was purified by flash chromatography with ethyl acetate to give the compound as a colorless oil (0.25 g) in 55% yield.

$^1$H NMR (300 MHz, CDCl$_3$) d: 1.36 and 1.37 (2t, 6H, J=7 Hz, CH$_3$), 2.01 (bs, 1H, OH), 2.99 (dd, 1H, J=10 Hz, 7 Hz, H-4a), 3.25 (dd, 1H, J=10 Hz, 6 Hz, H-4b), 3.69 (dd, 1H, J=12 Hz, 5 Hz, C$\underline{H}_A$H$_B$OH), 3.86 (dd, 1H, J=12 Hz, 4 Hz, CH$_A$$\underline{H}_B$OH), 4.23 (m, 4H, CH$_2$CH$_3$), 4.66 (m, 1H, H-5), 5.36 (d, 1H, $^2$J$_{HP}$=9 Hz, H-2).

Example 27

TRANS 2-DIETHYLOXYPHOSPHINOYL-5-p-TOLUENESULFONYLOXYMETHYL-1,3-OXATHIOLANE

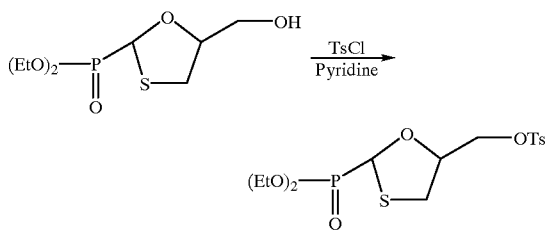

To a solution of trans-2-diethyloxyphosphinoyl-5-hydroxymethyl-1,3-oxathiolane (example 26) (0.24 g, 0.91 mmol) in pyridine (10 mL) was added p-toluenesulfonyl chloride (0.23 g, 1.18 mmol) at 0° C. The mixture was then placed in the refrigerator. After 18 h the reaction mixture was poured into ice-water and extracted with ethyl acetate (2x). The combined organic extracts were washed with water, 0.5N HCl (2x), water, dried and then concentrated to give a yellow oil. The crude material was purified by flash chromatography with a mixture of ethyl acetate and hexanes (60:40) to give the compound as a colorless oil (0.28 g) in 72% yield.

$^1$H NMR (300 MHz, CDCl$_3$) d: 1.31 (t, 6H, J=7 Hz, CH$_3$), 2.45 (s, 3H, ArCH$_3$), 2.88 (dd, 1H, J=11 Hz, 5 Hz, H-4a), 3.28 (dd, 1H, J=11 Hz, 6 Hz, H-4b), 4.05 (dd, 2H, J=5 Hz, 1 Hz, CH$_2$OTs), 4.16 and 4.17 (2q, 4H, C$\underline{H}_2$CH$_3$), 4.69 (p, 1H, J=6 Hz, H-5), 5.19 (d, 1H, J=8.5 Hz, H-2), 7.33 and 7.77 (m, 4H, Ar—H).

Example 28

TRANS-2-DIETHYLOXYPHOSPHINOYL-5-(2'-AMINO-6'-CHLOROPURIN-9'-YLMETHYL)-1,3-OXATHIOLANE

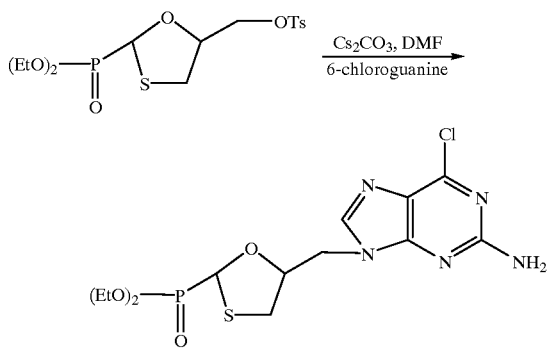

A mixture of trans-2-diethyloxyphosphinoyl-5-p-toluenesulfonyloxymethyl-1,3-oxathiolane (example 27) (0.27 g, 0.66 mmol), 2-amino-6-chloropurine (0.22 g, 1.29 mmol) and cesium carbonate (0.45 g, 1.24 mmol) in dimethylformamide (30 mL) was stirred at 65° C. for 18 h. The solvent was removed under reduced pressure and the residue was purified by flash chromatography with a mixture of ethyl acetate and methanol (93:7) to give the compound as a white foam (0.15 g) in 60% yield.

$^1$H NMR (300 MHz, CDCl$_3$) d: 1.25 and 1.27 (2t, 6H, J=7 Hz, CH$_3$), 2.76 (dd, 1H, J=11 Hz, 6 Hz, H-4a), 3.33 (dd, 1H, J=11 Hz, 6 Hz, H-4b), 4.12 and 4.13 (2q, 4H, C$\underline{H}_2$CH$_3$), 4.24 (dd, 1H, J=14.5 Hz, 6 Hz, CH$_A$H$_B$N), 4.32 (dd, 1H, J=14.5 Hz, 3.5 Hz, CH$_A$H$_B$N), 4.88 (m, 1H, H-5), 5.31 (d, 1H, $^2$J$_{HP}$=8 Hz, H-2), 7.82(s, 1H, H-8').

Example 29

TRANS 2-DIHYDROXYPHOSPHINOYL-5-(GUANIN-9'-YLMETHYL)-1,3-OXATHIOLANE (BCH-1550)

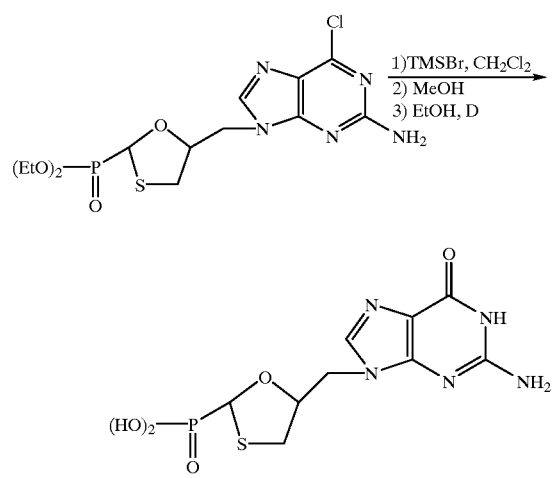

To a solution of trans-2-diethyloxyphosphinoyl-5-(2'-amino-6'-chloropurin-9'-ylmethyl)-1,3-oxathiolane (example 28) (0.086 g, 0.23 mmol) in dichloromethane (2 mL) was added trimethylsilylbromide (0.35 g, 2.31 mmol) at room temperature. After 18 hr, the solvent was removed under reduced pressure and the residue was triturated in methanol and the solvent removed (2x). The residue was recrystallized from ethanol. Upon heating in ethanol the 2-amino-6-chloropurine was converted to guanine to give the compound as a white solid (0.07 g) in 91% yield.

MP: >300° C.; UV l$_{max}$: (H$_2$O): 271, 252 nm.

$^1$H NMR (300 MHz, DMSO) d: 2.90 (dd, 1H, J=10 Hz, 5 Hz, H-4a), 3.16 (dd, 1H, J=10 Hz, 6 Hz, H-4b), 4.12 (dd, 2H, J=4 Hz, 3 Hz, CH$_2$N), 4.76 (p, 1H, J=5.5 Hz, H-5), 5.27 (d, 1H, $^2$J$_{HP}$=7 Hz, H-2), 6.46 (s, 2H, NH$_2$), 7.68 (s, 1H, H-8'), 10.54 (s, 1H, NH).

Example 30

CIS-2-(DIETHYLOXYPHOSPHINOYL)-5-YDROXYMETHYL-1,3-OXATHIOLANE

TRANS-2-(DIETHYLOXYPHOSPHINOYL)-5-HYDROXYMETHYL-1,3-OXATHIOLANE

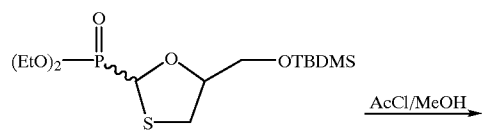

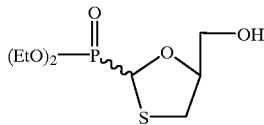

To a solution of cis and trans-5-t-butyldimethylsilyloxymethyl-2-(diethyloxyphosphinoyl)-1,3-oxathiolane (example 25) (4.00 g, 10.8 mmol) in MeOH (30 mL) was added a few drops of acetyl chloride (200 μL) at 0° C. The mixture was stirred at 0° C. for 1 hr. and at room temperature for 18 hr. A few drops of ammonium chloride was added and the solvent was evaporated under reduced pressure. The crude material was purified by several flash chromatography with a mixture of dichloromethane and methanol (96:4) to give 382 mg of the cis isomer, 1.19 g of the trans isomer and 332 mg of the mixture in a total yield of 80% after the first purification.

cis isomer

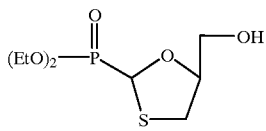

$^1$H NMR (300 MHz, CDCl$_3$) δ: 1.37 (t, 6H, J=7.0 Hz, CH$_3$), 3.03 (dd, 1H, J=5.4 Hz, 10.8 Hz, H-4a), 3.31 (dd, 1H, J=9.0 Hz, 10.9 Hz, H-4b), 3.74 (dd, 1H, J=4.0 Hz, 12.3 Hz, CH$_A$H$_B$OH), 3.98 (dd, 1H, J=2.9 Hz, 12.4 Hz, CH$_A$H$_B$OH), 4.24 (m, 4H, CH$_2$), 4.40 (m, 1H, H-5), 5.30 (d, 1H, $^2$J$_{HP}$=9.6 Hz, H-2).

trans isomer

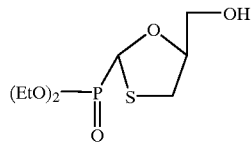

$^1$H NMR (300 MHz, CDCl$_3$) δ: 1.37 (m, 6H, CH$_3$), 2.05 (bs, 1H, OH), 3.00 (dd, 1H, J=7.0 Hz, 10.2 Hz, H-4a), 3.25 (dd, 1H, J=6.3 Hz, 10.4 Hz, H-4b), 3.69 (dd, 1H, J=4.9 Hz, 11.9 Hz, CH$_A$H$_B$OH), 3.85 (dd, 1H, J=3.9 Hz, 11.9 Hz, CH$_A$H$_B$OH), 4.23 (m, 4H, CH$_2$), 4.65 (m, 1H, H-5), 5.36 (d, 1H, $^2$J$_{HP}$=8.6 Hz, H-2).

Example 31

CIS-5-(2'-AMINO-6'-CHLOROPURIN-9'-YLMETHYL)-2-(DIETHYLOXYPHOSPHINOYL)-1,3-OXATHIOLANE

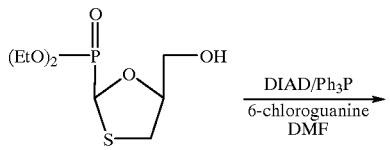

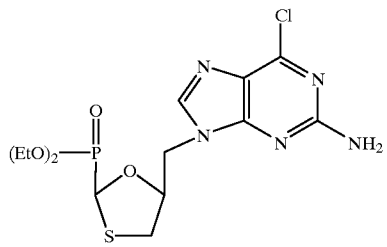

To a solution of cis-2-(diethyloxyphosphinoyl)-5-hydroxymethyl-1,3-oxathiolane (example 30) (220 mg, 0.859 mmol), triphenylphosphine (450 mg, 1.717 mmol, 2 eq) and 6-chloroguanine (291 mg, 1.717 mmol, 2 eq) in DMF (10 mL) was added diisopropylazodicarboxylate (338 μL, 1.717 mmol, 2 eq) at −10° C. The mixture was stirred at −10° C. for 3 hr. and at room temperature for 18 hr. The solvent was evaporated under reduced pressure and the crude material was purified by flash chromatography with a mixture of ethyl acetate and methanol (95:5) to give the compound (105 mg) in a 30% yield.

$^1$H NMR (300 MHz, CDCl$_3$) δ: 1.35 (2t, 6H, J=7.2 Hz, CH$_3$), 3.03 (dd, 1H, J=8.2 Hz, 11.0 Hz, H-4a), 3.18 (dd, 1H, J=5.2 Hz, 10.9 Hz, H-4b), 4.23 (m, 4H, CH$_2$), 4.42 (d, 2H, J=5 Hz, CH$_2$N), 4.59 (m, 1H, H-5), 5.08 (bs, 2H, NH$_2$), 5.28 (d, 1H, $^2$J$_{HP}$=8.8 Hz, H-2), 7.99 (s, 1H, H-8').

Example 32

CIS-2-(DIHYDROXYPHOSPHINOYL)-5-(GUANIN-9'-YLMETHYL)-1,3-OXATHIOLANE, MONOAMMONIUM SALT (BCH-1819)

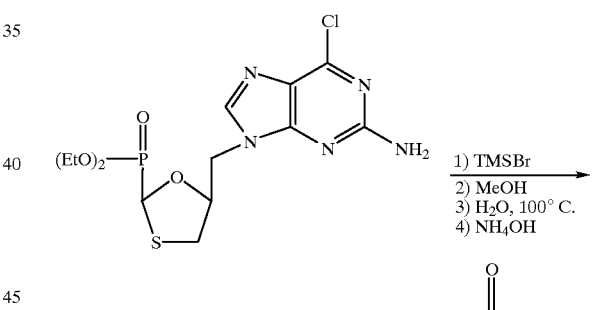

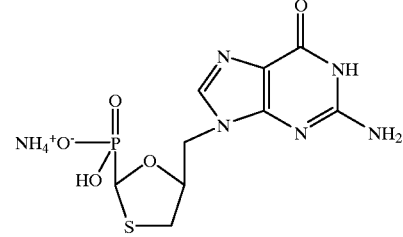

To a solution of cis-5-(2'-amino-6'-chloropurin-9'-ylmethyl)-2-(diethyloxyphosphinoyl)-1,3-oxathiolane (example 31) (105 mg, 0.257 mmol) in dichloromethane (10 mL) was added TMSBr (1.02 mL, 7.72 mmol, 30 eq) at room temperature. The mixture was stirred at room temperature for 16 hr and the solvent was evaporated to dryness. Methanol was added and evaporated. Then water was added and the solution was heated at 100° C. for 24 hr to convert 6-chloroguanine to guanine. Water was evaporated, followed by the addition of water and ammonium hydroxide and reevaporated again to get a solid which was purify by reverse phase HPLC to give the compound (13 mg) in a 14% yield.

$^1$H NMR (300 MHz, D$_2$O) δ: 2.60 (dd, 1H, J=7.7 Hz, 10.3 Hz, H-4a), 2.98 (dd, 1H, J=4.8 Hz, 10.3 Hz, H-4b), 4.19 (m, 3H, CH$_2$N and H-5), 4.84 (d, 1H, $^2$J$_{HP}$=3.4 Hz, H-2), 7.81 (s, 1H, H-8'). UV λ$_{max}$ (H$_2$O): 253.1 and 270.7 nm.

Example 33

TRANS-2-(DIETHYLOXYPHOSPHINOYL)-5-(THYMIN-1'-YLMETHYL)-1,3-OXATHIOLANE

TRANS-2-(DIETHYLOXYPHOSPHINOYL)-5-(THYMIN-3'-YLMETHYL)-1,3-OXATHIOLANE

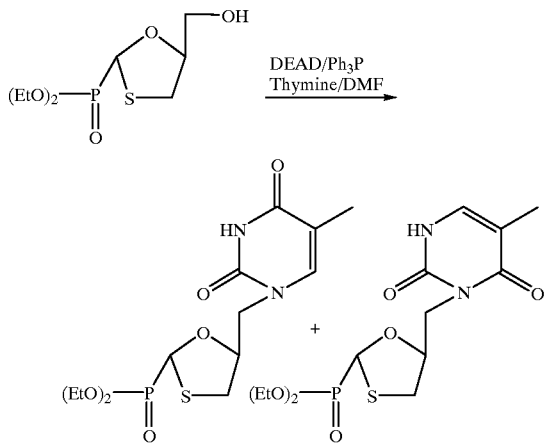

To a solution of trans-2-(diethyloxyphosphinoyl)-5-hydroxymethyl-1,3-oxathiolane (example 30) (400 mg, 1.56 mmol), triphenylphosphine (819 mg, 3.12 mmol, 2 eq) and thymine (394 mg, 3.12 mmol, 2 eq) in DMF (15 mL) was added DEAD (492 µL, 3.12 mmol, 2 eq) at −30° C. The mixture was stirred at −30° C. for 3 hr. and at room temperature for 18 hr. The solvent was evaporated and the crude material was purified by flash chromatography with a mixture of ethyl acetate and methanol (95:5) to give the compounds (223 mg) in a 39% yield. The ratio of N1:N3 is 1:2.

$^1$H NMR (300 MHz, CDCl$_3$) δ: 1.32 (m, 6H, CH$_3$), 1.90 and 1.91 (2s, 3H, CH$_3$), 2.87 (dd, 0.33H, J=6.0 Hz, 10.5 Hz, H-4a for N1), 3.00 (dd, 0.66H, J=3.0 Hz, 10.7 Hz, H-4a for N3), 3.27 (dd, 0.66H, J=6.0 Hz, 10.8 Hz, H-4b for N3), 3.35 (dd, 0.33H, J=6.0 Hz, 10.8 Hz, H-4b for N1), 3.89 (m, 1H, CH$_A$H$_B$N), 4.03 (dd, 0.33H, J=3.3 Hz, 14.5 Hz, CH$_A$H$_B$N for N1), 4.19 (m, 4H, CH$_2$), 4.41 (dd, 0.66H, J=8.5 Hz, 13.4 Hz, CH$_A$H$_B$N for N3), 4.79 (m, 0.33H, H-5 for N1), 4.97 (m, 0.66H, H-5 for N3), 5.34 (d, 0.33H, $^2$J$_{HP}$=8.2 Hz, H-2 for N1), 5.53 (d, 0.66H, $^2$J$_{HP}$=10.7 Hz, H-2 for N3), 7.03 (d and s, 1H, H-6'), 9.0 (bs, 0.33H, NH for N1), 9.7 (bs, 0.66H, NH for N3).

Example 34

TRANS-2-(DIHYDROXYPHOSPHINOYL)-5-(THYMIN-1'-YLMETHYL)-1,3-OXATHIOLANE, MONOAMMONIUM SALT (BCH-1820)

TRANS-2-(DIHYDROXYPHOSPHINOYL)-5-(THYMIN-3'-YLMETHYL)-1,3-OXATHIOLANE, MONOAMMONIUM SALT (BCH-1821)

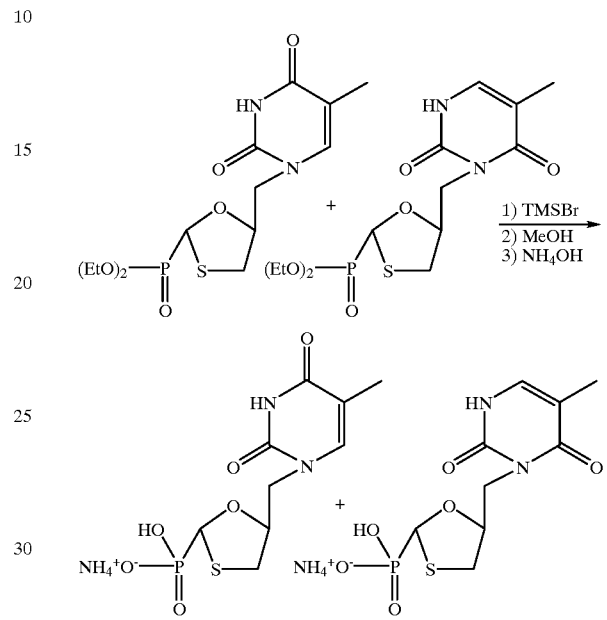

To a solution of trans-2-(diethyloxyphosphinoyl)-5-(thymin-1'-ylmethyl)-1,3-oxathiolane and trans-2-(diethyloxyphosphinoyl)-5-(thymin-3'-ylmethyl)-1,3-oxathiolane (example 33) (200 mg, 0.55 mmol) in dichloromethane (10 mL) was added TMSBr (1.8 mL, 13.7 mmol, 25 eq) at room temperature. The mixture was stirred at room temperature for 18 hr and the solvent was evaporated to dryness. Methanol was added and evaporated. Water and ammonium hydroxide were added and evaporated to get a solid which was purifed by reverse phase HPLC to give the compound 25 mg of the N1 isomer, 41 mg of the N3 isomer and 45.8 mg of mixture in a 66% total yield.

N1 isomer

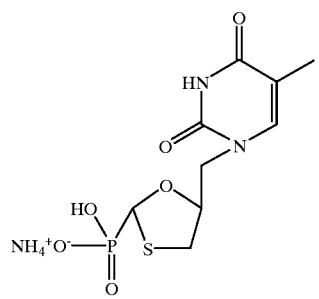

$^1$H NMR (300 MHz, DMSO) δ: 1.74 (s, 3H, CH$_3$), 2.62 (dd, 1H, J=6.3 Hz, 10.2 Hz, H-4a), 3.04 (dd, 1H, J=6.2 Hz, 10.2 Hz, H-4b), 3.78 (m, 2H, CH$_2$N), 4.61 (m, 1H, H-5), 4.96 (d, 1H, $^2$J$_{HP}$=3.5 Hz, H-2), 7.46 (s, 1H, H-6').

$^{13}$C NMR (75.46 MHz, DMSO) δ: 12.3 (CH$_3$), 34.1 (C-4), 49.3 (CH$_2$N), 79.9 (d, $^3$J$_{CP}$=4.2 Hz, C-5), 81.6 (d, $^1J_{CP}$=160.8 Hz, C-2), 108.5 (C-5'), 142.5 (C-6'), 151.5 (C-2'), 164.7 (C-4'). UV $\lambda_{max}$ (H$_2$O): 270.4 nm. MP: >230° C.
N3 isomer

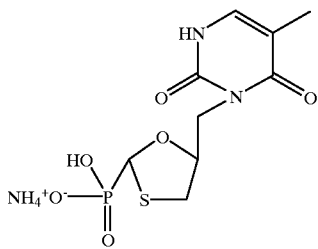

$^1$H NMR (300 MHz, DMSO) δ: 1.78 (s, 3H, CH$_3$), 2.72 (dd, 1H, J=4.8 Hz, 10.3 Hz, H-4a), 2.98 (dd, 1H, J=6.0 Hz, 10.3 Hz, H-4b), 3.76 (dd, 1H, J=5.8 Hz, 12.9 Hz, C$\underline{H}_AH_B$N), 4.10 (dd, 1H, J=7.1 Hz, 12.9 Hz, CH$_A\underline{H}_B$N), 4.66 (m, 1H, H-5), 4.97 (d, 1H, $^2J_{HP}$=4.5 Hz, H-2), 7.31 (s, 1H, H-6').
$^{13}$C NMR (75.46 MHz, DMSO) δ: 12.9 (CH$_3$), 34.8 (C-4), 42.1 (CH$_2$N), 79.6 (d, $^3J_{CP}$=4.9 Hz, C-5), 81.3 (d, $^1J_{CP}$=162.9 Hz, C-2), 107.5 (C-5'), 136.9 (C-6'), 151.9 (C-2'), 164.3 (C-4'). UV $\lambda_{max}$ (H$_2$O): 264.9 nm. MP: >230° C.

Example 35

TRANS-2-(DIETHYLOXYPHOSPHINOYL)-5-(URACIL-1'-YLMETHYL)-1,3-OXATHIOLANE

TRANS-2-(DIETHYLOXYPHOSPHINOYL)-5-(URACIL-3'-YLMETHYL)-1,3-OXATHIOLANE

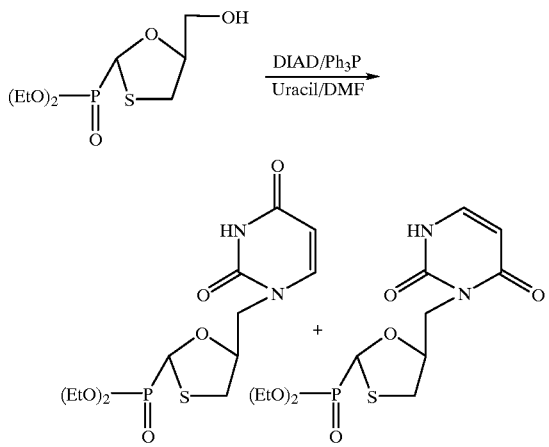

To a solution of trans-2-(diethyloxyphosphinoyl)-5-hydroxymethyl-1,3-oxathiolane (example 30) (300 mg, 1.17 mmol), triphenylphosphine (614 mg, 2.34 mmol, 2 eq) and uracil (262 mg, 2.34 mmol, 2 eq) in DMF (10 mL) was added DIAD (461 μL, 2.34 mmol, 2 eq) at –10° C. The mixture was stirred at –10° C. for 2 hr. and at room temperature for 18 hr. The solvent was evaporated and the crude material was purified by flash chromatography with a mixture of ethyl acetate and methanol (95:5) to give the compounds (139 mg) in a 34% yield. The ratio of N1:N3 is ~1:1.

$^1$H NMR (300 MHz, CDCl$_3$) δ: 1.34 (m, 6H, CH$_3$), 2.88 (dd, 0.5H, J=6.3 Hz, 10.7 Hz, H-4a for N1), 2.98 (dd, 0.5H, J=3.2 Hz, 10.6 Hz, H-4a for N3), 3.27 (dd, 0.5H, J=5.8 Hz, 10.5 Hz, H-4b for N3), 3.38 (dd, 0.5H, J=6.2 Hz, 10.8 Hz, H-4b for N1), 3.90 (m, 1H, C$\underline{H}_AH_B$N), 4.06 (dd, 0.5H, J=3.3 Hz, 14.8 Hz, CH$_A\underline{H}_B$N for N1), 4.20 (m, 4H, CH$_2$), 4.40 (dd, 0.5H, J=8.8 Hz, 13.7 Hz, CH$_A\underline{H}_B$N for N3), 4.80 (m, 0.5H, H-5 for N1), 4.97 (m, 0.5H, H-5 for N3), 5.33 (d, 0.5H, $^2J_{HP}$=8.1 Hz, H-2 for N1), 5.52 (d, 0.5H, $^2J_{HP}$=10.9 Hz, H-2 for N3), 5.71 (m, 1H, H-5'), 7.20 (dd, 0.5H, J=6.5 Hz, 6.5 Hz, H-6' for N3), 7.27 (d, 0.5H, J=7.8 Hz, H-6' for N1), 9.18 (bs, 0.5H, NH for N1), 9.96 (bs, 0.5H, NH for N3).

Example 36

TRANS-2-(DIHYDROXYPHOSPHINOYL)-5-(URACIL-1'-YLMETHYL)-1,3-OXATHIOLANE, MONOAMMONIUM SALT

TRANS-2-(DIHYDROXYPHOSPHINOYL)-5-(URACIL-3'-YLMETHYL)-1,3-OXATHIOLANE, MONOAMMONIUM SALT

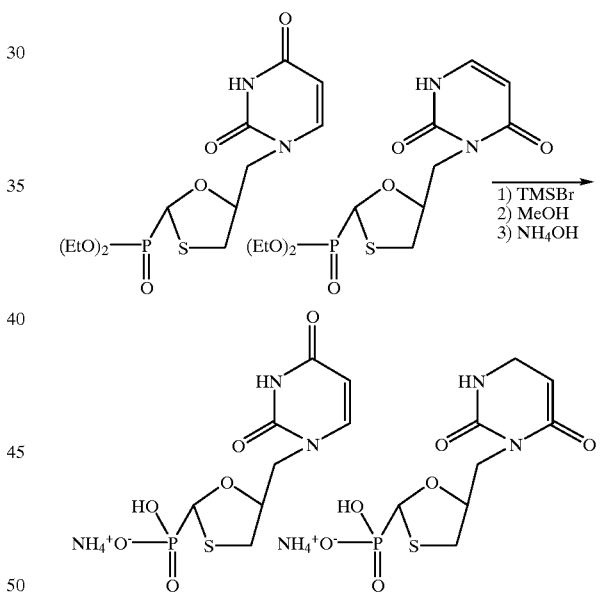

To a solution of trans-2-(diethyloxyphosphinoyl)-5-(uracil-1'-ylmethyl)-1,3-oxathiolane and trans-2-10 (diethyloxyphosphinoyl)-5-(uracil-3'-ylmethyl)-1,3-oxathiolane (example 35) (139 mg, 0.397 mmol) in dichloromethane (10 mL) was added TMSBr (1.3 mL, 9.9 mmol, 25 eq) at room temperature. The mixture was stirred at room temperature for 18 hr and the solvent was evaporated to dryness. Methanol was added and evaporated. Water and ammonium hydroxide were added and evaporated to get a solid which was purified by reverse phase HPLC to give 30 mg of the N1 isomer and 20.6 mg of N3 isomer in a 41% total yield.

N1 isomer

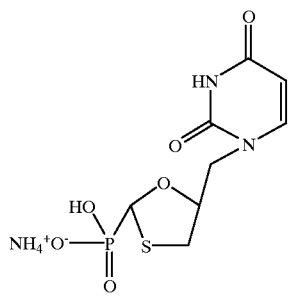

¹H NMR (300 MHz, DMSO) δ: 2.62 (dd, 1H, J=6.3 Hz, 10.4 Hz, H-4a), 3.05 (dd, 1H, J=6.2 Hz, 10.3 Hz, H-4b), 3.82 (m, 2H, CH₂N), 4.61 (m, 1H, H-5), 4.95 (d, 1H, $^2J_{HP}$=3.6 Hz, H-2), 5.52 (d, 1H, J=7.9 Hz, H-5'), 7.57 (d, 1H, J=7.9 Hz, H-6'). UV $\lambda_{max}$ (H₂O): 265.1 nm.

N3 isomer

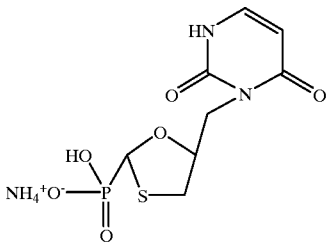

¹H NMR (300 MHz, DMSO) δ: 2.71 (dd, 1H, J=5.0 Hz, 10.1 Hz, H-4a), 2.98 (dd, 1H, J=5.8 Hz, 10.2 Hz, H-4b), 3.73 (dd, 1H, J=5.6 Hz, 13.1 Hz, C$\underline{H}_AH_BN$), 4.08 (dd, 1H, J=7.1 Hz, 13.0 Hz, CH$_A\underline{H}_BN$), 4.66 (m, 1H, H-5), 4.95 (d, 1H, $^2J_{HP}$=4.4 Hz, H-2), 5.57 (d, 1H, J=7.6 Hz, H-5'), 7.43 (d, 1H, J=7.6 Hz, H-6'). UV $\lambda_{max}$ (H₂O): 258.9 nm. MP: >230° C.

Example 37

CIS-5-(ADENIN-9'-YLMETHYL)-2-(DIETHYLOXYPHOSPHINOYL)-1,3-OXATHIOLANE

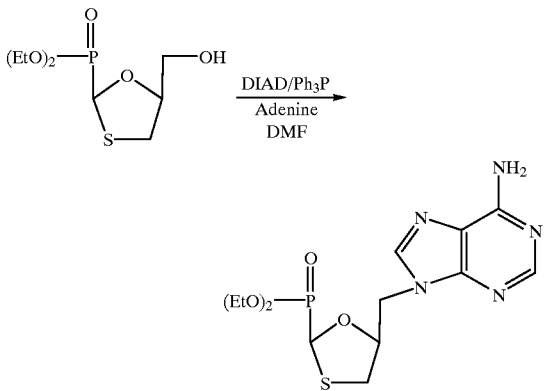

To a solution of cis-2-(diethyloxyphosphinoyl)-5-hydroxymethyl-1,3-oxathiolane (example 30) (279 mg, 1.09 mmol), triphenylphosphine (571 mg, 2.18 mmol, 2 eq) and adenine (294 mg, 2.18 mmol, 2 eq) in DMF (15 mL) was added DIAD (430 μL, 2.18 mmol, 2 eq) at −10° C. The mixture was stirred at −10° C. for 2 hr. and at room temperature for 44 hr. The solvent was evaporated and the crude material was purified twice by flash chromatography with a mixture of dichloromethane and methanol (90:10) to give the compound (82 mg) in a 20% yield.

¹H NMR (300 MHz, CDCl₃) δ: 1.31 and 1.36 (2t, 6H, J=7.4 Hz, CH₃), 2.99 (dd, 1H, J=8.1 Hz, 10.9 Hz, H-4a), 3.19 (dd, 1H, J=5.2 Hz, 11.0 Hz, H-4b), 4.22 (m, 4H, CH₂), 4.54 (d, 2H, J=2.8 Hz, CH₂N), 4.61 (m, 1H, H-5), 5.29 (d, 1H, $^2J_{HP}$=9.0 Hz, H-2), 5.75 (bs, 2H, NH₂), 8.02 (s, 1H, H-2') and 8.35 (s, 1H, H-8').

Example 38

CIS-5-(ADENIN-9'-YLMETHYL)-2-(DIHYDROXYPHOSPHINOYL)-1,3-OXATHIOLANE, MONOAMMONIUM SALT (BCH-1831)

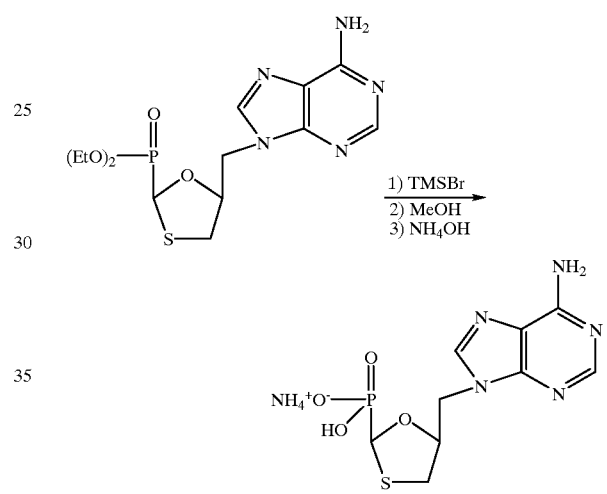

To a solution of cis-5-(adenin-9'-ylmethyl)-2-(diethyloxyphosphinoyl)-1,3-oxathiolane (example 37) (80 mg, 0.214 mmol) in dichloromethane (10 mL) was added TMSBr (1.0 mL, 7.58 mmol, 35 eq) at room temperature. The mixture was stirred at room temperature for 48 hr and the solvent was evaporated to dryness. Methanol was added and evaporated then water and ammonium hydroxide were added and evaporated, to get a solid which was purified by reverse phase HPLC to give the compound (24.8 mg) in a 35% yield.

¹H NMR (300 MHz, D₂O) δ: 2.64 (dd, 1H, J=8.4 Hz, 10.4 Hz, H-4a), 3.03 (dd, 1H, J=5.4 Hz, 10.4 Hz, H-4b), 4.30 (m, 3H, CH₂N and H-5), 4.87 (d, 1H, $^2J_{HP}$=4.2 Hz, H-2), 8.05 and 8.13 (2s, 2H, H-2' and H-8').

¹H NMR (300 MHz, DMSO) δ: 2.83 (dd, 1H, J=6.4 Hz, 10.3 Hz, H-4a), 3.02 (dd, 1H, J=5.8 Hz, 10.3 Hz, H-4b), 4.33 (m, 2H, C$\underline{H}_AH_BN$ and H-5), 4.55 (dd, 1H, J=8.5 Hz, 14.9 Hz, CH$_A\underline{H}_BN$), 4.88 (d, 1H, $^2J_{HP}$=2.8 Hz, H-2), 7.20 (bs, 2H, NH₂), 8.12 and 8.42 (2s, 2H, H-2' and H-8').

¹³C NMR (75.46 MHz, DMSO) δ: 34.3 (C-4), 46.2 (CH₂N), 82.4 (C-5), 83.4 (d, $^1J_{CP}$=167.1 Hz, C-2), 118.7 (C-5'), 142.6 (C-8'), 149.8 (C-4'), 152.6 (C-2'), 156.3 (C-6'). UV $\lambda_{max}$ (H₂O): 259.8 nm. MP: >230° C.

Example 39

METHYL 3-t-BUTYLDIPHENYLSILYLOXY-2-HYDROXYPROPIONATE

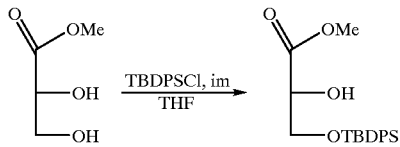

To a solution of methyl glycerate (25.88 g, 215 mmol) and imidazole (22.0 g, 323 mmol, 1.5 eq) in tetrahydrofuran (250 mL) was added t-butyldiphenylsilyl chloride (53.0 mL, 204 mmol, 0.95 eq) at 0° C. After stirring for 18 h the reaction was quenched by the addition of saturated ammonium chloride and the aqueous phase was extracted with dichloromethane. The organic layer was dried with magnesium sulfate and evaporated under reduced pressure. The crude material was purified by flash chromatography with a mixture of hexanes and ethyl acetate (80:20) to give the compound (68.89 g) in 94% yield.

$^1$H NMR (300 MHz, CDCl$_3$) δ: 1.04 (s, 9H, t-butyl), 3.80 (s, 3H, CO$_2$CH$_3$), 3.93 (dd, 1H, J=2.9 Hz, 9.0 Hz, H-3a), 3.98 (dd, 1H, J=2.9 Hz, 9.0 Hz, H-3b), 4.26 (dd, 1H, J=2.9 Hz, 2.9 Hz, H-2), 7.42 and 7.65 (m, 10H, Ar—H).

Example 40

METHYL 3-t-BUTYLDIPHENYLSILYLOXY-2-THIOACETOXYPROPIONATE

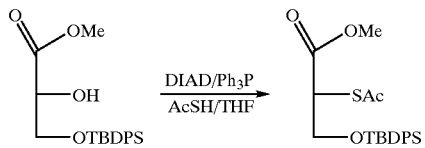

To a solution of triphenylphosphine (101 g, 385 mmol, 2 eq) in THF (1.5 L) was added diisopropylazodicarboxylate (76 mL, 386 mmol, 2 eq) at 0° C. The mixture was stirred at 0° C. for 1 hr and was followed by the addition of a solution of methyl 3-t-butyldiphenylsilyloxy-2-hydroxypropionate (example 39) (68.89 g, 192 mmol) and thioacetic acid (27.6 mL, 386 mmol, 2 eq.) in THF, to the same temperature. The mixture was stirred at 0° C. for 1 hr and at room temperature for 18 hr. The solution was concentrated to dryness and the solid was washed with hexane (5×300 mL). The organic solution was filtered and evaporated under reduced pressure. The crude material was purified by flash chromatography with a mixture of hexane and ethyl acetate (95:5) to give the pure compound (49.3 g) in 62% yield.

$^1$H NMR (300 MHz, CDCl$_3$) δ: 1.03 (s, 9H, t-butyl), 2.35 (s, 3H, SCOCH$_3$), 3.75 (s, 3H, CO$_2$CH$_3$), 3.93 (dd, 1H, J=6.6 Hz, 9.9 Hz, H-3a), 4.01 (dd, 1H, J=4.9 Hz, 9.9 Hz, H-3b), 4.45 (dd, 1H, J=6.8 Hz, 4.9 Hz, H-2), 7.42 and 7.64 (m, 10H, Ar—H).

Example 41

3-t-BUTYLDIPHENYLSILYLOXY-2-MERCAPTOPROPANOL

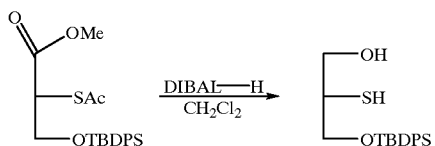

To a solution of methyl 3-t-butyldiphenylsilyloxy-2-thioacetoxypropionate (example 40) (14.3 g, 34.4 mmol) in dichloromethane (1.0 L) was added diisobutylaluminium hydride (96 mL of 1.5 M solution in toluene, 144 mmol, 4.2 eq) at −78° C. The solution was stirred at −78° C. for 1 hr and at −50° C. for another 1.5 hr. Sodium sulfate decahydrate (15 g) was added and the mixture was warmed at room temperature for 2 hr. Acetone was added and the solution was stirred overnight. Anhydrous sodium sulfate was added and the solution was stirred for 30 min and filtered over CELITE diatomeceous earth. The solid was washed several times with acetone and the solvents were evaporated under reduced pressure. The crude material was purified by flash chromatography with a mixture of hexane and ethyl acetate (85:15) to give the desired compound (4.25 g) in 36% yield.

$^1$H NMR (300 MHz, CDCl$_3$) δ: 1.08 (s, 9H, t-butyl), 1.56 (d, 1H, J=9.9 Hz, SH), 3.02 (m, 1H, H-2), 3.7–3.93 (m, 4H, CH$_2$), 7.43 and 7.67 (m, 10H, Ar—H).

Example 42

CIS AND TRANS 4-(t-BUTYLDIPHENYLSILYLOXYMETHYL)-2-(DIETHYLOXYPHOSPHINOYL)-1,3-OXATHIOLANE

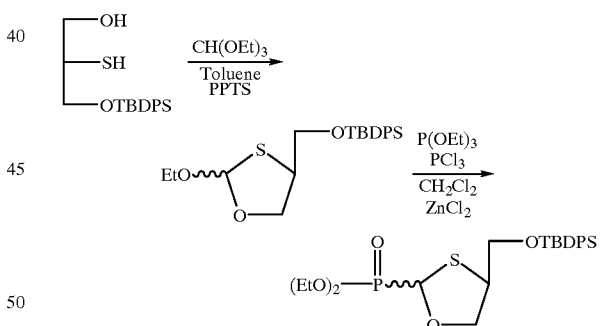

To a solution of 3-t-butyldiphenylsilyloxy-2-mercaptopropanol (example 41) (12.17 g, 35.12 mmol) in toluene (600 mL) were added triethylorthoformate (6.4 mL, 38.5 mmol, 1.1 eq) and pyridinium p-toluenesulfonate (catalytic) at 90° C. The solution was stirred at 90° C. for 40 min then was quenched at room temperature with sodium bicarbonate. The aqueous phase was extracted with dichloromethane and the organic layer was washed with water, dried with magnesium sulfate and evaporated under reduced pressure. The crude product was obtained in 92% yield (12.94 g) as a 2:1 mixture and was used without further purification.

To a solution of 4-(t-butyldiphenylsilyloxymethyl)-2-ethoxy-1,3-oxathiolane (12.32 g, 30.6 mmol) and triethylphosphite (3.5 mL, 20.4 mmol, 0.66 eq) in dichloromethane (50 mL) were added phosphorus trichloride (890 μL, 10.2 mmol, 0.33 eq) and zinc chloride (catalytic) at 0° C. The solution was stirred at 0° C. for 1 hr and at room temperature for 3 days. The solvent was evaporated and the crude material was purified by flash chromatography with a mixture of hexane and ethyl acetate (60:40) to give the pure compound (8.02 g) in 53% yield with a ratio of 2:1 (trans:cis).
Orthoester:

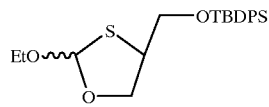

$^1$H NMR (300 MHz, CDCl$_3$) δ: 1.06 (s, 9H, t-butyl), 1.24 (t, 3H, J=7.1 Hz, CH$_3$), 3.5–3.9 (m, 5H, CH$_2$, CH$_2$O, H-4), 4.14 (m, 1H, C$\underline{H}_A$H$_B$O), 4.22 (dd, 0.33H, J=6.9 Hz, 9.2 Hz, CH$_A$$\underline{H}_B$O), 4.45 (d, 0.66H, J=10.0 Hz, CH$_A$$\underline{H}_B$O), 6.17 and 6.30 (2s, 1H, H-2), 7.41 and 7.64 (m, 10H, Ar—H).
Phosphonate:

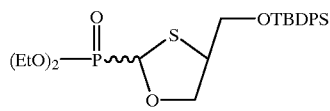

$^1$H NMR (300 MHz, CDCl$_3$) δ: 1.05 (s, 9H, t-butyl), 1.36 (m, 6H, CH$_3$), 3.63 (m, 2H, CH$_2$O), 3.85 (m, 0.33H, C$\underline{H}_A$H$_B$O for cis), 4.09–4.33 (m, 4H, CH$_2$; 1.33H, CH$_2$O for trans; 1H, H-4), 4.61 (d, 0.33H, J=9.0 Hz, CH$_A$$\underline{H}_B$O for cis), 5.21 (d, 0.33H, $^2$J$_{HP}$=9.4 Hz, H-2 for cis), 5.27 (d, 0.66H, $^2$J$_{HP}$=9.8 Hz, H-2 for trans), 7.41 and 7.64 (m, 10H, Ar—H).

Example 43

CIS AND TRANS 2-(DIETHYLOXYPHOSPHINOYL)-4-HYDROXYMETHYL-1,3- OXATHIOLANE

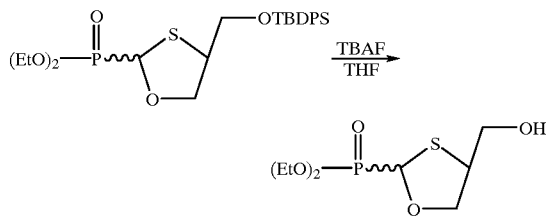

To a solution of cis and trans 4-(t-butyldiphenylsilyloxymethyl)-2-(diethyloxyphosphinoyl)-1,3-oxathiolane (example 42) (5.00 g, 10.07 mmol) in tetrahydrofurane (300 mL) was added tetrabutylammonium fluoride (15.0 mL, 15.0 mmol, 1.5 eq) at room temperature. The solution was stirred at room temperature for 45 min and acetic acid was added (850 μL) followed by evaporation under reduced pressure. The crude material was purified by flash chromatography with ethyl acetate to give the pure compound (2.47 g) in 96% yield.
$^1$H NMR (300 MHz, CDCl$_3$) δ: 1.36 (2t, 6H, J=7.1 Hz, CH$_3$), 3.20 (m, 0.33H, C$\underline{H}_A$H$_B$O for cis), 3.64 (m, 1.33H, CH$_2$O for trans), 3.75 (m, 1H, OH and 0.33H, CH$_A$$\underline{H}_B$O for cis), 3.95 (dd, 0.33H, J=6.1 Hz, 9.9 Hz, C$\underline{H}_A$H$_B$O for cis), 4.23 (m, 4H, CH$_2$; 1H H-4; 0.66H, C$\underline{H}_A$H$_B$O for trans), 4.33 (dd, 0.66H, J=7.6 Hz, 9.9 Hz, CH$_A$$\underline{H}_B$O for trans), 4.49 (dd, 0.33H, J=3.5 Hz, 9.9 Hz, CH$_A$$\underline{H}_B$O for cis), 5.23 (d, 0.33H, $^2$J$_{HP}$=9.9 Hz, H-2 for cis), 5.33 (d, 0.66H, $^2$J$_{HP}$=9.3 Hz, H-2 for trans).

Example 44

CIS 4-(2'-AMINO-6'-CHLOROPURIN-9'-YLMETHYL)-2-(DIETHYLOXYPHOSPHINOYL)-1,3-OXATHIOLANE

TRANS 4-(2'-AMINO-6'-CHLOROPURIN-9'-YLMETHYL)-2-(DIETHYLOXYPHOSPHINOYL)-1,3-OXATHIOLANE

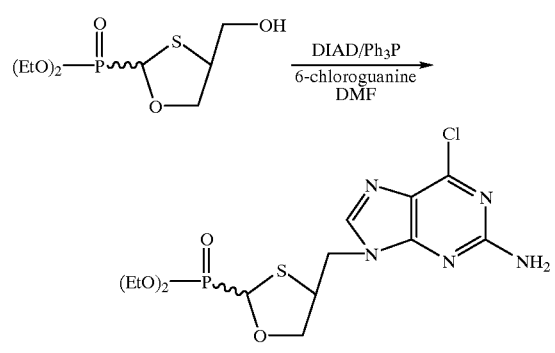

To a solution of cis and trans 2-(diethyloxyphosphinoyl)-4-(hydroxymethyl)-1,3-oxathiolane (example 43) (1.596 g, 6.2 mmol), 2-amino-6-chloropurine (2.117 g, 12.5 mmol, 2 eq) and triphenylphosphine (3.286 g, 12.5 mmol, 2 eq) in dimethylformamide (100 mL) was added slowly diisopropylazodicarboxylate (2.45 mL, 12.4 mmol, 2 eq) at −10° C. The solution was stirred at −10° C. for 3 hr and at room temperature for 18 hr and the solvent was evaporated under reduced pressure. The crude material was purified by flash chromatography with ethyl acetate and methanol (96:4) to give the cis compound (405 mg) and the trans (1.227 g) in 64% yield.

cis isomer

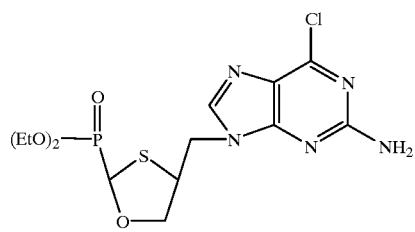

$^1$H NMR (300 MHz, CDCl$_3$) δ: 1.37 and 1.40 (2t, 6H, J=7.1 Hz, CH$_3$), 3.98 (dd, 1H, J=4.2 Hz, 9.6 Hz, H-5a), 4.12–4.31 (m, 6H, H-5b, H-4, CH$_2$), 4.40 (m, 2H, CH$_2$N), 5.13 (s, 2H, NH$_2$), 5.26 (d, 1H, $^2$J$_{HP}$=10.1 Hz, H-2), 8.14 (s, 1H, H-8').

trans isomer

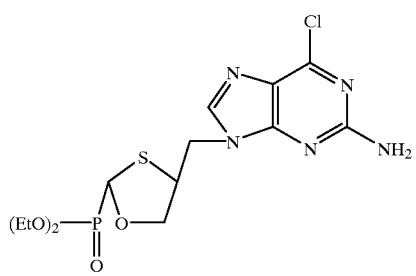

$^1$H NMR (300 MHz, CDCl$_3$) δ: 1.34 (m, 6H, CH$_3$), 4.14–4.38 (m, 9H, H-5, H-4, CH$_2$), 5.13 (s, 2H, NH$_2$), 5.35 (d, 1H, $^2J_{HP}$=9.0 Hz, H-2), 7.83 (s, 1H, H-8').

Example 45

CIS 2-(DIHYDROXYPHOSPHINOYL)-4-(GUANIN-9'-YLMETHYL)-1,3-OXATHIOLANE, MONOAMMONIUM SALT (BCH-2593)

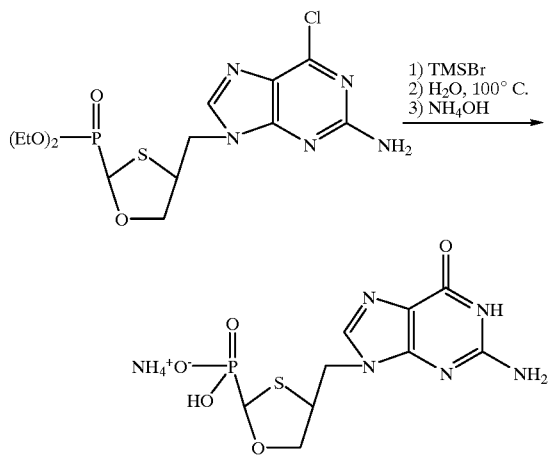

To a solution of cis 4-(2'-amino-6'-chloropurin-9'-ylmethyl)-2-(diethyloxyphosphinoyl)-1,3-oxathiolane (example 44) (198 mg, 0.486 mmol) in dichloromethane (10 mL) was added trimethylsilylbromide (1.3 mL, 9.7 mmol, 20 eq) at room temperature. The solution was stirred at room temperature for 18 hr and the solvent was evaporated. Water was added and the solution was heated at 100° C. for 48 hr for the conversion to guanine. Then water was evaporated, ammonium hydroxide wad added and the solution was reevaporated again. The crude material was purified by reverse phase HPLC to give the compound (71.3 mg) in 42% yield.

$^1$H NMR (300 MHz, D$_2$O) α: 3.65 (dd, 1H, J=4.3 Hz, 10.1 Hz, H-5a), 3.92 (m, 2H, CH$_2$), 4.18 (m, 2H, CH$_A$H$_B$, H-4), 4.98 (d, 1H, $^2J_{HP}$=8.0 Hz, H-2), 7.88 (s, 1H, H-8'). MP: >250° C. UV λ$_{max}$ (H$_2$O): 252.4, 270.2 nm.

Example 46

TRANS 2-(DIHYDROXYPHOSPHINOYL)-4-(GUANIN-9'-YLMETHYL)-1,3-OXATHIOLANE, MONOAMMONIUM SALT (BCH-2594)

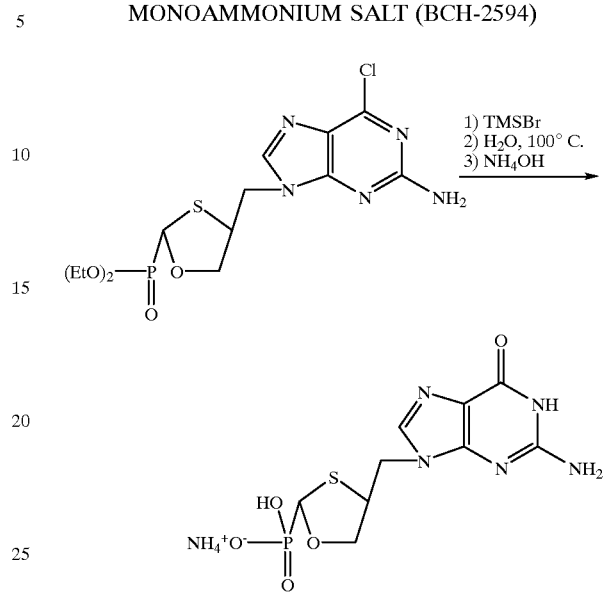

To a solution of trans 4-(2'-amino-6'-chloropurin-9'-ylmethyl)-2-(diethyloxyphosphinoyl)-1,3-oxathiolane (example 44) (398 mg, 0.976 mmol) in dichloromethane (15 mL) was added trimethylsilylbromide (2.6 mL, 19.5 mmol, 20 eq) at room temperature. The solution was stirred at room temperature for 18 hr and the solvent was evaporated. Water was added and the solution was heated at 100° C. for 48 hr for the conversion to guanine. Then water was evaporated, ammonium hydroxide was added and the solution was evaporated again. Half of the crude material was purified by reverse phase HPLC to give the compound (56.5 mg) in 33% total yield.

$^1$H NMR (300 MHz, D$_2$O) δ: 3.91 (m, 2H, CH$_2$), 4.10 (m, 3H, CH$_2$ and H-4), 5.02 (d, 1H, $^2J_{HP}$=6.0 Hz, H-2), 7.76 (s, 1H, H-8'). MP: >250° C.; UV λ$_{max}$ (H$_2$O): 252.4, 270.7 nm.

Example 47

1-t-BUTYLDIMETHYLSILYLOXY-2,3-DIMERCAPTOPROPANE

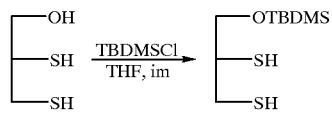

To a solution of 2,3-dimercapto-1-propanol (15.0 ml, 150 mmol) and imidazole (15.3 g, 224 mmol, 1.5 eq) in THF (300 mL) was added t-butyldimethylsilyl chloride (21.4 g, 142 mmol, 0.95 eq) at 0° C. The mixture was stirred at 0° C. for 1 hr and at room temperature for 18 hr. A saturated solution of ammonium chloride was added and the aqueous phase was extracted with dichloromethane. The organic layer was dried with anhydrous sodium sulphate and the solvent was evaporated under reduced pressure. The crude material was purified by flash chromatography with a mixture of hexane and ethyl acetate (90:10) to give the pure compound (32.04 g) in 94.5w yield.

$^1$H NMR (300 MHz, CDCl$_3$) δ: 0.08 (s, 6H, CH$_3$), 0.91 (s, 9H, t-butyl), 1.58 (t, 1H, J=8.5 Hz, 5H), 1.82 (d, 1H, J=9.2 Hz, 5H), 2.85 (m, 2H, H-3), 2.96 (m, 1H, H-2), 3.63 (dd, 1H, J=6.7 Hz, 10.1 Hz, H-1a), 3.86 (dd, 1H, J=4.4 Hz, 10.2 Hz, H-1b).

Example 48

4-t-BUTYLDIMETHYLSILYLOXYMETHYL-2-ETHOXY-1,3-DITHIOLANE

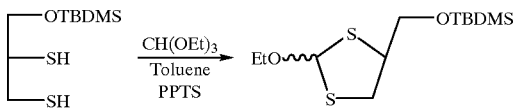

To a solution of 1-t-butyldimethylsilyloxy-2,3-dimercaptopropane (example 47) (32.00 g, 134 mmol) in toluene (400 mL) were added triethylorthoformate (29.0 mL, 174 mmol, 1.3 eq) and pyridinium p-toluenesulfonate (200 mg). The solution was stirred at 120°–130° C. for 6 hr then was quenched at room temperature with a solution of saturated sodium bicarbonate. The aqueous phase was extracted with dichloromethane and the organic layer was dried with magnesium sulfate and evaporated under reduced pressure. The crude product was obtained in 94% yield (37.17 g) as a 1:1 mixture and was used without further purification.

$^1$H NMR (300 MHz, CDCl$_3$) δ: 0.06 and 0.07 (2s, 6H, CH$_3$), 0.89 (s, 9H, t-butyl), 1.22 and 1.23 (2t, 3H, J=7.0 Hz, CH$_3$), 3.28–3.70 (m, 5H, H-5, CH$_2$Q, H-4), 3.75–4.00 (m, 2H, CH$_2$O), 6.19 and 6.20 (2s, 1H, H-2).

Example 49

CIS-4-(t-BUTYLDIMETHYLSILYLOXYMETHYL)-2-(DIETHYLOXYPHOSPHINOYL)-1,3-DITHIOLANE

TRANS-4-(t-BUTYLDIMETHYLSILYLOXYMETHYL)-2-(DIETHYLOXYPHOSPHINOYL)-1,3-DITHIOLANE

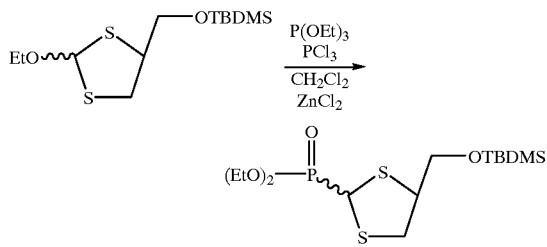

To a solution of 4-(t-butyldimethylsilyloxymethyl)-2-ethoxy-1,3-dithiolane (example 48) (37.1 g, 126 mmol) and triethylphosphite (14.3 mL, 83.0 mmol, 0.66 eq) in dichloromethane (100 mL) were added phosphorus trichloride (3.6 mL, 42.0 mmol, 0.33 eq) and zinc chloride (catalytic) at 0° c. The solution was stirred at 0° C. for 2 hr and at room temperature for 18 hr. The solvent was evaporated and the crude material was purified by flash chromatography with a mixture of hexane and ethyl acetate (80:20 to 60:40) to give 3.64 g of the cis isomer, 8.62 g of the trans isomer and 9.95 g of the mixture (2:1 trans:cis) for a total yield of 46%.

cis isomer

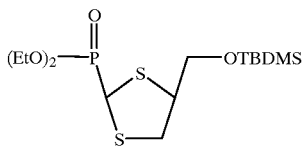

$^1$H NMR (300 MHz, CDCl$_3$) δ: 0.06 (s, 6H, CH$_3$), 0.89 (s, 9H, t-butyl), 1.35 (t, 6H, J=7.0 Hz, CH$_3$), 3.26 (dd, 1H, J=4.9 Hz, 11.9 Hz, H-5a), 3.38 (dd, 1H, J=6.3 Hz, 12.1 Hz, H-5b), 3.71 (dd, 1H, J=5.7 Hz, 9.9 Hz, C$\underline{H}_A$H$_B$O), 3.80 (dd, 1H, J=8.5 Hz, 9.9 Hz, CH$_A\underline{H}_B$O), 3.90 (m, 1H, H-4), 4.23 (m, 4H, CH$_2$), 4.39 (d, 1H, $^2J_{HP}$=4.0 Hz, H-2)

trans isomer

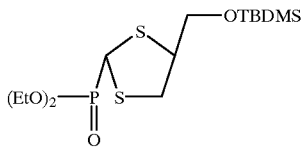

$^1$H NMR (300 MHz, CDCl$_3$) δ: 0.06 (s, 6H, CH$_3$), 0.89 (s, 9H, t-butyl), 1.35 (t, 6H, J=7.1 Hz, CH$_3$), 3.38 (dd, 1H, J=2.5 Hz, 11.9 Hz, H-5a), 3.45 (dd, 1H, J=4.9 Hz, 12.1 Hz, H-5b), 3.52 (dd, 1H, J=5.3 Hz, 10.1 Hz, C$\underline{H}_A$H$_B$O), 3.65 (dd, 1H, J=9.8 Hz, 10.1 Hz, CH$_A\underline{H}_B$O), 3.90 (m, 1H, H-4), 4.22 (m, 4H, CH$_2$), 4.28 (d, 1H, $^2J_{HP}$=3.8 Hz, H-2).

Example 50

CIS 2-(DIETHYLOXYPHOSPHINOYL)-4-HYDROXYMETHYL-1,3-DITHIOLANE

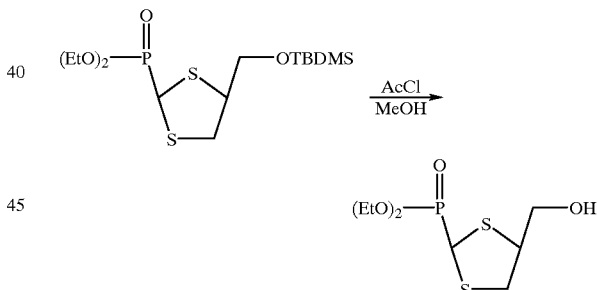

To a solution of cis-4-(t-butyldimethylsilyloxymethyl)-2-(diethyloxyphosphinoyl)-1,3-dithiolane (example 49) (3.70 g, 9.56 mmol) in anhydrous methanol (50 mL) was added acetyl chloride (6 drops) at 0° C. The solution was stirred at 0° C. for 30 min and then at room temperature for 4.5 hrs. A saturated solution of ammonium chloride (3 drops) was added and the solution was stirred for 15 min followed by evaporation of solvents. The crude material was purified by flash chromatography with a mixture of dichloromethane and methanol (95:5) to give the compound (2.02 g) in 77% yield.

$^1$H NMR (300 MHz, CDCl$_3$) δ: 1.34 (t, 6H, J=7.0 Hz, CH$_3$) 3.30 (dd, 1H, J=5.5 Hz, 12.0 Hz, H-5a), 3.42 (dd, 1H, J=6.0 Hz, 12.1 Hz, H-5b), 3.80 (m, 2H, CH$_2$OH and 1H, OH), 4.05 (m, 1H, H-4), 4.19 (m, 4H, CH$_2$), 4.35 (d, 1H, $^2J_{HP}$=4.1 Hz, H-2).

Example 51

CIS 4-(2'-AMINO-6'-CHLOROPURIN-9'-YLMETHYL)-2-(DIETHYLOXYPHOSPHINOYL)-1,3-DITHIOLANE

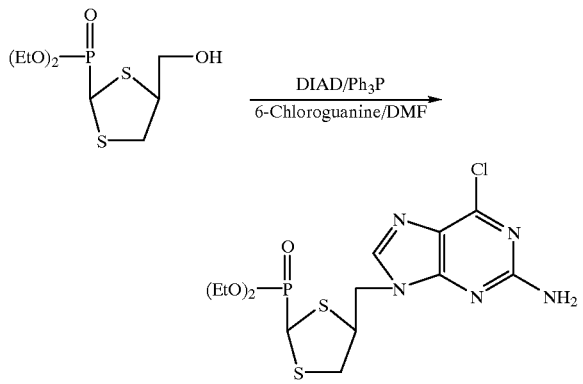

To a solution of cis-2-(diethyloxyphosphinoyl)-4-(hydroxymethyl)-1,3-dithiolane (example 50) (1.00 g, 3.67 mmol), 2-amino-6-chloropurine (1.25 g 7.34 mmol, 2.0 eq), and triphenylphosphine (1.93 g, 7.34 mmol, 2.0 eq) in dimethylformamide (75 mL) was added slowly diisopropylazodicarboxylate (1.53 ml, 7.34 mmol, 2.0 eq) at −10° C. The solution was stirred at −10° C. for 3 hrs, at room temperature for 18 hrs, and then the solvent was evaporated under reduced pressure. The crude material was purified by flash chromatography with a mixture of dichloromethane and methanol (95:5) to give a white foam (0.90 g) in 58% yield.

$^1$H NMR (300 MHz, CDCl$_3$) δ: 1.37 and 1.39 (2t, 6H, J=7.0 Hz, CH$_3$), 3.39 (dd, 1H, J=2.0 Hz, 12.6 Hz, H-5a), 3.45 (dd, 1H, J=4.7 Hz, 12.3 Hz, H-5b), 4.25 (m, 4H, CH$_2$), 4.37–4.46 (m, 3H, C$\underline{H}_A$H$_B$N, H-4 and H-2), 4.64 (dd, 1H, J=15.4 Hz, 11.3 Hz, CH$_A\underline{H}_B$N), 5.06 (s, 2H, NH$_2$), and 8.28 (s, 1H, H-8').

Example 52

CIS 2-(DIHYDROXYPHOSPHINOYL)-4-(GUANIN-9'-YLMETHYL)-1,3-DITHIOLANE, MONOAMMONIUM SALT (BCH-2599)

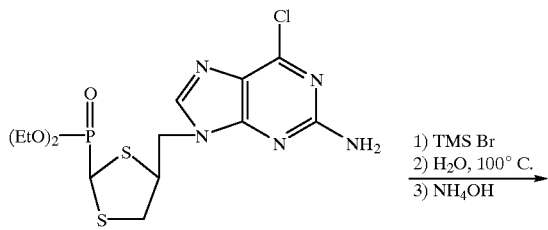

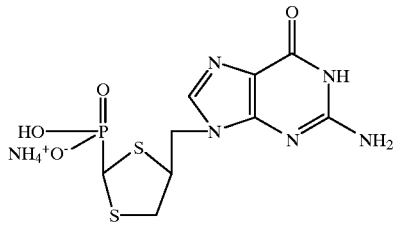

To a solution of cis-4-(2'-amino-6'-chloropurin-9'-ylmethyl)-2-(diethyloxyphosphinoyl)-1,3-dithiolane (example 51) (303 mg, 0.715 mmol) in dichloromethane (10 mL) was added trimethylsilylbromide (1.9 ml, 14.3 mmol, 20.0 eq) at room temperature. The solution was stirred at room temperature for 18 hrs and then the solvent was evaporated. Water was added (25 ml) and the solution was heated at 100° C. for 48 hrs for the conversion to guanine. The water was evaporated, ammonium hydroxide was added and the solution was evaporated again. The crude material was purified by reverse phase HPLC to give a white solid (47 mg) in 18% yield.

$^1$H NMR (300 MHz, D$_2$O) δ: 3.05 (d, 2H, J=3.6 Hz, H-5), 4.05–4.13 (m, 2H, C$\underline{H}_A$H$_B$N and H-4), 4.29 (m, 1H, CH$_A$C$\underline{H}_B$N), 4.34 (d, 1H, $^2$J$_{HP}$=5.2 Hz, H-2), and 7.76 (s, 1H, H-8'). UV λ$_{max}$ (H$_2$O): 252.0, 272.7 nm. MP: 250° C. (dec).

Example 53

TRANS 2-(DIETHYLOXYPHOSPHINOYL)-4-HYDROXYMETHYL-1,3-DITHIOLANE

To a solution of trans-4-(t-butyldimethylsilyloxymethyl)-2-(diethyloxyphosphinoyl)-1,3-dithiolane (example 49) (9.84 g, 25.46 mmol) in anhydrous methanol (150 mL) was added acetyl chloride (12 drops) at 0° C. The solution was stirred at 0° C. for 30 min and then at room temperature for 3.5 hrs. A saturated solution of ammonium chloride (5 drops) was added and the solution was stirred for 15 min followed by evaporation of the solvents. The crude material was purified by flash chromatography with a mixture of dichloromethane and methanol (94:6) to give a white solid (5.97 g) in 86% yield.

$^1$H NMR (300 MHz, CDCl$_3$) δ: 1.33 (t, 6H, J=7.1 Hz, CH$_3$), 3.30 (dd, 1H, J=2.5 Hz, 12.0 Hz, H-5a), 3.49 (dd, 1H, J=5.2 Hz, 12.1 Hz, H-5b), 3.60 (dd, 1H, J=6.3 Hz, 11.0 Hz, C$\underline{H}_A$H$_B$OH), 3.71 (dd, 1H, J=8.0 Hz, 11.1 Hz, CH$_A\underline{H}_B$OH), 3.98 (m, 1H, H-4), 4.19 (m, 4H, CH$_2$), 4.29 (d, 1H, $^2$J$_{HP}$=4.1 Hz, H-2).

Example 54

TRANS 4-(2'-AMINO-6'-CHLORO-9'-YLMETHYL)-2-(DIETHYLOXYPHOSPHINOYL)-1,3-DITHIOLANE

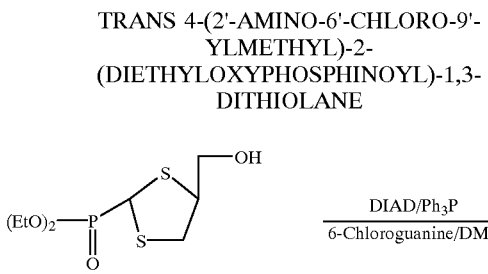

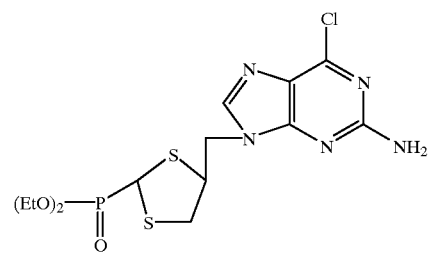

To a solution of trans-2-(diethyloxyphosphinoyl)-4-(hydroxymethyl)-1,3-dithiolane (example 53) (1.00 g, 3.67 mmol), 2-amino-6-chloropurine (1.26 g 7.34 mmol, 2.0 eq), and triphenylphosphine (1.95 g, 7.34 mmol, 2.0 eq) in dimethylformamide (75 mL) was added slowly diisopropylazodicarboxylate (1.53 ml, 7.34 mmol, 2.0 eq) at −10° C. The solution was stirred at −10° C. for 3 hrs, at room temperature for 18 hrs, and then the solvent was evaporated under reduced pressure. The crude material was purified by flash chromatography with a mixture of dichloromethane and methanol (97:3) to give a yellow foam (0.53 g) in 34% yield.

$^1$H NMR (300 MHz, CDCl$_3$) δ: 1.33 and 1.35 (2t, 6H, J=7.0 Hz, CH$_3$), 3.09 (dd, 1H, J=1.9 Hz, 12.6 Hz, H-5a), 3.58 (dd, 1H, J=5.5 Hz, 12.3 Hz, H-5b), 4.15–4.37 (m, 6H, CH$_2$N and CH$_2$), 4.39 (d, 1H, $^2J_{HP}$=4.4 Hz, H-2), 4.46 (m, 1H, H-4), 5.12 (s, 2H, NH$_2$), and 7.79 (s, 1H, H-8').

Example 55

TRANS 2-(DIHYDROXYPHOSPHINOYL)-4-(GUANIN-9'-YLMETHYL)-1,3-DITHIOLANE, MONOAMMONIUM SALT (BCH-2665)

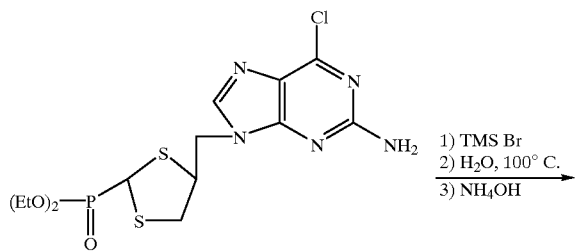

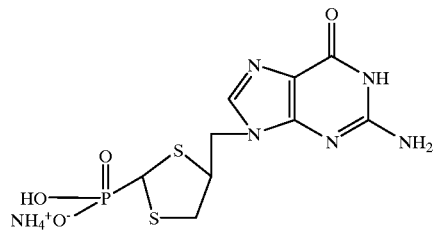

To a solution of trans-4-(2'-amino-6'-chloropurin-9'-ylmethyl)-2-(diethyloxyphosphinoyl)-1,3-dithiolane (example 54) (250 mg, 0.590 mmol) in dichloromethane (10 mL) was added trimethylsilylbromide (1.6 ml, 11.8 mmol, 2.0 eq) at room temperature. The solution was stirred at room temperature for 18 hrs and then the solvent was evaporated. Water was added (25 ml) and the solution was heated at 100° C. for 48 hrs for the conversion to guanine. The water was evaporated, ammonium hydroxide was added and the solution was evaporated again. The crude material was purified by reverse phase HPLC to give a white solid (40 mg) in 18% yield.

$^1$H NMR (300 MHz, D$_2$O) δ: 2.99 (bd, 1H, J=12.3 Hz, H-5a), 3.22 (dd, 1H, J=4.1 Hz, 12.1 Hz, H-5b), 4.01–4.22 (m, 3H, CH$_2$N and H-4), 4.30 (d, 1H, $^2J_{HP}$=3.9 Hz, H-2), and 7.71 (s, 1H, H-8'). UV λ$_{max}$ (H$_2$O): 252.2, 275.3 nm. MP: 250° C. (dec).

Example 56

(±)-DIHYDRO-5-HYDROXYMETHYL-2(3H)-FURANONE

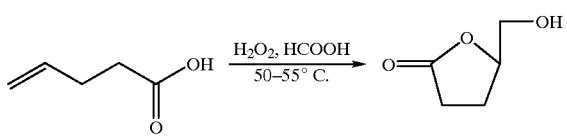

To a stirring solution of 19% hydrogen peroxide (35 mL, 0.20 mol) in 85% aqueous formic acid (60 mL) at 50–55° C. was added over a 15 min period a solution of 4-pentenoic acid (15 g, 0.15 mol) in 85% aqueous formic acid (30 mL). The solution was maintained at this temperature for 2 h. Concentration gave an oil which comprised of a mixture of the desired compound and the corresponding formate ester. The oil was then stirred in methanol (50 mL) containing concentrated hydrochloric acid (1 mL) for 3 h. Concentration gave the desired compound as an oil (17.2 g, 99%.).

$^1$H NMR (300 MHz, CDCl$_3$) δ: 4.60 (m, 1 H, H-5), 3.89 (dd, 1 H, H-6, J=2.7 HZ and 12.6 Hz), 3.63 (dd, 1H, H-6', J=4.5 HZ and 12.3 Hz), 2.6 (m, 2 H, H-3), 2.3 (m, 3 H, H-4, OH).

Example 57

(±)-DIHYDRO-5-(p-TOLUENESULFONYLOXYMETHYL)-2(3H)-FURANONE

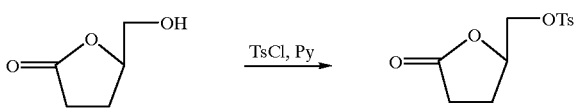

p-Toluenesulfonyl chloride (23.65 g, 124.03 mmol) was added portion wise to a solution of (±)-dihydro-5-hydroxymethyl-2(3H)-furanone (example 56) (11.07 g, 95.43 mmol) and pyridine (15.4 mL, 190.86 mmol) in methylene chloride (300 mL) at 0° C. The solution was allowed to. warm to rt and stirred overnight. The solution was then washed with water (2×100 mL), 0.5 n HCl until the washings were acidic and finally with saturated NaHCO$_3$. After drying and concentrating, the residue was triturated with toluene to give the title compound as a white solid (19.63 g, 76%).

$^1$H NMR (300 MHz, CDCl$_3$) δ: 7.79 (d, 2 H, Ar—H, J=8.3 Hz), 7.38 (d, 2 H, Ar—H, J=8.3 Hz), 4.69 (m, 1 H, H-5), 4.20 (dd, 1 H, H-6, J=3.4 HZ and 11.0 Hz), 4.14 (dd, 1 H, H-6', J=4.1 HZ and 11.0 Hz), 2.5 (m, 2 H, H-3), 2.44 (s, 3 H, Ar—CH$_3$), 2.3, 2.1 (m, 2 H, H-4).

Example 58

(±)2-HYDROXY-5-(p-TOLUENESULFONYLOXYMETHYL)-TETRAHYDROFURAN

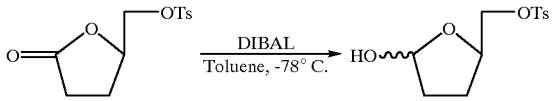

To a suspension of (±)-dihydro-5-(p-toluensulfonyloxymethyl)-2(3H)-furanone (example 57) (5.20 g, 19.26 mmol) in anhydrous toluene (125 mL) at −78° C. was added DIBAL (1.5 M in toluene, 13.5 mL, 20.22 mmol) dropwise. The solution was allowed to stir at −78° C. for 2 h. water was then added to the mixture and the reaction mixture was brought to rt. The mixture was filtered through a CELITE diatomaceous earth and the organic layer was collected, dried (MgSO$_4$) and concentrated to give the title compound as a 1:1 mixture of cis and trans isomers (4.2 g, 80%).

$^1$H NMR (300 MHz, CDCl$_3$) δ: 7.78 (2 d, 2 H, Ar—H), 7.34 (2 d, 2 H, Ar—H), 5.44 (m, 1 H, H-2), 3.9–4.4 (m, 3 H, H-6, H-6', H-5), 2.43 (s, 3 H, Ar—CH$_3$), 1.6–2.2 (m, 4 H, H-3 and H-4).

Example 59

(±)-2-ACETOXY-5-(p-TOLUENESULFONYLOXYMETHYL)-TETRAHYDROFURAN

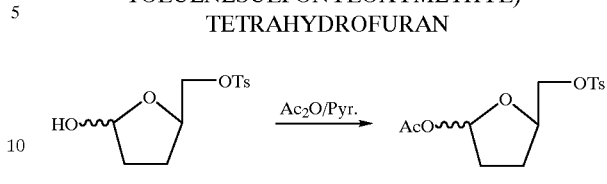

To a stirring solution of (±)2-hydroxy-5-(p-toluenesulfonyloxymethyl)-tetrahydrofuran (example 58) (4.20 g, 15.44 mmol), pyridine (2.75 mL, 33.97 mmol) and DMAP (catalytic) in methylene chloride (100 mL) at rt was added acetic anhydride (2.91 mL, 30.88 mmol). After stirring the solution for 1 h, it was washed with water (50 mL), 1 N HCl (50 mL), saturated NaHCO$_3$ (50 mL), dried (MgSO$_4$) and concentrated to give the title compound as a 1:1 mixture of cis and trans isomers (4.85 g, 100%).

$^1$H NMR (300 MHz, CDCl$_3$) δ: 7.76 (2 d, 2 H, Ar—H), 7.34 (2 d, 2 H, Ar—H), 6.20 (m, 1 H, H-2), 4.0–4.4 (m, 3 H, H6, H-6', H-5), 2.42 (s, 3 H, Ar—CH$_3$), 1.99 (s, 3 H, C(O)CH$_3$, 1.8–2.2 (m, 4 H, H-3 and H-4).

Example 60

(±)-2-DIETHOXYPHOSPHINOYL-5-(p-TOLUENESULFONYLOXYMETHYL)-TETRAHYDROFURAN

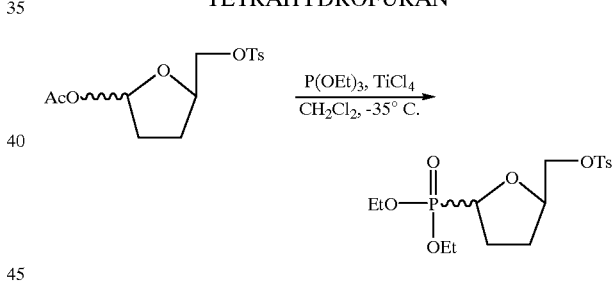

To a stirring solution of (±)-2-acetoxy-5-(p-toluenesulfonoxymethyl)-tetrahydrofuran (example 59) (1.63 g, 5.19 mmol) and triethyl phosphite (1.16 mL, 6.75 mmol) in methylene chloride (75 mL) at −35° C. was added titanium (IV) chloride (0.57 mL, 5.19 mmol) dropwise. The yellow solution was then stirred at −35° C. for 30 min and then at 0° C. for 30 min. Saturated NaHCO$_3$ (75 mL) was then added to the reaction mixture and the suspension was then filtered through a CELITE diatomaceous earth. The mixture was then partitioned followed by extraction of the aqueous phase with methylene chloride (2×50 mL). The combined extracts were then washed with brine (100 mL), dried (MgSO$_4$) and concentrated. The residue was then purified by chromatography eluting with 75% EtAc/hexanes-EtAc giving the title compound as 1:1 mixture of cis and trans isomers (1.42 g, 78%).

$^1$H NMR (300 MHz, CDCl$_3$) δ: 7.75 (2 d, 2 H, Ar—H), 7.32 (d, 2 H, Ar—H), 4.1 (m, 8 H), 2.43 (s, 3 H, CH$_3$), 1.8 (m, 4 H), 1.25 (m, 6 H).

Example 61

(±)-2-DIETHOXYPHOSPHINOYL-5-(CYTOSIN-1'-YLMETHYL)-TETRAHYDROFURAN

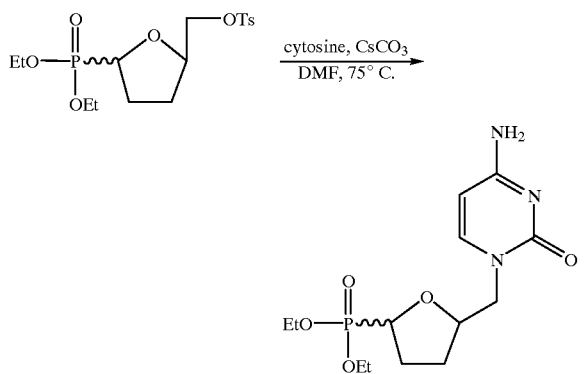

A mixture of (±)-2-diethoxyphosphinoyl-5-(p-toluenesulfonyloxymethyl)-tetrahydrofuran (example 60) (508 mg, 1.30 mmol), cytosine (288 mg, 2.60 mmol) and cesium carbonate (847 mg, 2.60 mmol) in dry DMF (10 mL) was stirred at 75° C. overnight. The mixture was then cooled and filtered followed by concentration of the filtrate. The residue was then purified by flash chromatography eluting with 10% MeOH in methylene chloride to give the title compound as a 1:1 mixture of cis and trans isomers. The product was also contaminated with $N^1$-ethylcytosine. The yield of desired product was estimated at 42%.

$^1$H NMR (300 MHz, CDCl$_3$) δ: 7.74, 7.38 (d, 1 H, H-6', J=7.0 Hz), 5.65, 5.61 (d, 1 H, H-5', J=7.0 Hz), 5.6 (br, 2 H, NH$_2$), 4.32, 4.45 (m, 1H), 4.15 (m, 5 H), 2.15 (m, 3 H), 1.60, 1.85 (m, 1 H), 1.3 (2 t, 6 H).

Example 62

(±)-CIS and TRANS-2-DIHYDROXYPHOSPHINOYL-5-(CYTOSIN-1'-YLMETHYL)-TETRAHYDROFURAN MONOAMMONIUM SALT

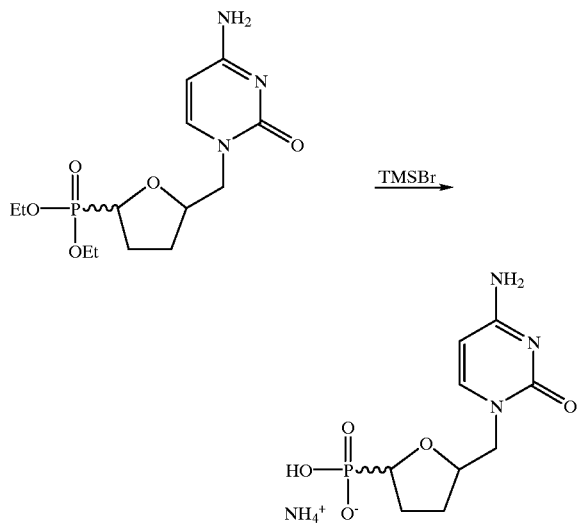

To a solution of (±)-2-diethoxyphosphinoyl-5-(cytosin-1'-ylmethyl)-tetrahydrofuran (example 61) (312 mg, 0.94 mmol) in dry dichloromethane (10 mL) was added TMSBr (1.2 mL, 9.40 mmol). The solution was stirred overnight at rt and the solution was concentrated to dryness. Methanol (3×5 mL) was then evaporated from the residue. The mixture of cis-trans isomers was then separated by HPLC (ion-exchange column).

Cis-isomer $^1$H NMR (300 MHz, D$_2$O) δ: 7.65 (d, 1 H, H-6', J=7.3 Hz), 5.82 (d, 1 H, H-5', J=7.3 Hz), 4.12 (m, 1 H, H-5), 3.92 (dd, 1 H, H-6$_a$, J=2.8 HZ and 14.0 Hz), 3.82 (t, 1 H, H-2, J=7.9 Hz), 3.51 (dd, 1 H, H-6$_b$, J=9.0 HZ and 14.0 Hz), 1.95 (m, 3 H), 1.67 (m, 1 H).

$^{13}$C NMR (75.5 MHz, D$_2$O) δ: 167.1, 159.0, 149.0, 95.9, 79.0 (d, J$_C$-p=8 Hz), 77.0 (d, J$_C$-p=162 Hz), 54.1, 29.2 (d, J$_C$-P=7 Hz), 27.5. UV $\lambda_{max}$ 273 nm.

Trans isomer $^1$H NMR (300 MHz, D$_2$O) δ: 7.50 (d, 1 H, H-6', J=7.3 Hz), 5.83 (d, 1 H, H-5', J=7.3 Hz), 4.17 (m, 1 H, H-5), 3.63–3.81 (m, 3 H), 1.84–1.98 (m, 3 H), 1.45 (m, 1 H) UV $\lambda_{max}$ (H$_2$O) 274 nm.

Example 63

(±)-CIS AND TRANS-5-(6'-CHLOROPURIN-9'-YLMETHYL)-2-DIETHOXYPHOSPHINOYL-TETRAHYDROFURAN

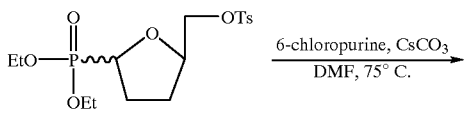

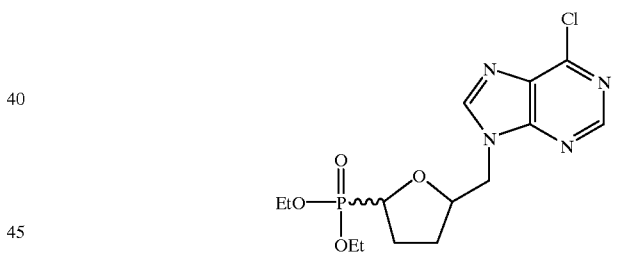

A mixture of (±)-2-diethoxyphosphinoyl-5-(p-toluenesulfonyloxymethyl)-tetrahydrofuran (example 60) (2.961 g, 7.55 mmol), 6-chloropurine (1.518 g, 9.82 mmol) and cesium carbonate (3.200 g, 9.82 mmol) in dry DMF (30 mL) was stirred at 75° C. overnight. The mixture was then cooled and filtered followed by concentration of the filtrate. The residue was then purified by flash chromatography eluting with 5% MeOH in ethyl acetate. The mixture of cis and trans isomers could thus be partially separated. Overall yield: 1.467 g, 52%.

Cis-isomer (110 mg).

$^1$H NMR (300 MHz, CDCl$_3$) δ: 8.69 (s, 1 H, H-8'), 8.50 (s, 1 H, H-2'), 4.45 (m, 2 H), 4.30 (m, 1 H), 4.15 (m, 5 H), 2.25 (m, 3 H), 1.90 (m, 1 H), 1.35 (2 t, 6 H).

Trans-isomer (306 mg).

$^1$H NMR (300 MHz, CDCl$_3$) δ: 8.68 (s, 1 H, H-8'), 8.22 (s, 1 H, H-2'), 4.45 (m, 2 H), 4.30 (m, 1 H), 4.05 (m, 5 H), 2.15 (m, 2 H), 2.0 (m, 1 H), 1.88 (m, 1 H), 1.20 (2 t, 6 H).

Example 64

(±)-CIS-5-(ADENIN-9'-YLMETHYL)-2-DIHYDROXYPHOSPHINOYL-TETRAHYDROFURAN

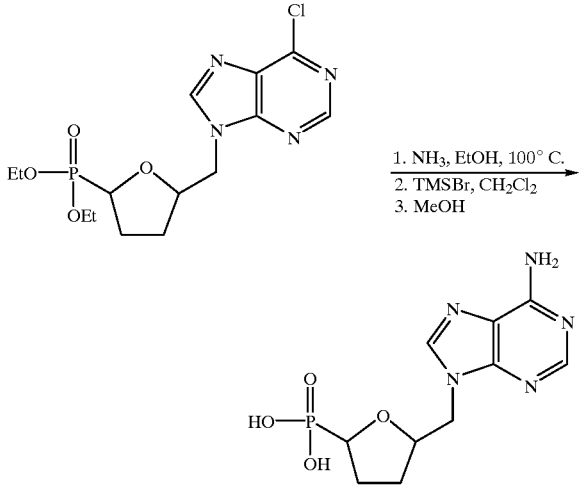

An ice-cold solution of (±)-cis-5-(6'-chloropurin-9'-ylmethyl)-2-diethoxyphosphinoyl-tetrahydrofuran (example 63) (110 mg, 0.29 mmol) in EtOH (20 mL) was saturated with ammonia. The solution was then heated at 100° C. in a steel bomb for 16 h. The bomb was then cooled in ice and vented. Concentration of the solution gave a residue which was dissolved in dry methylene chloride (5 mL) and treated with TMSBr (0.38 mL, 2.90 mmol). The reaction mixture was then allowed to stir at rt for 16 h. The mixture was concentrated to dryness and methanol (3×5 mL) was evaporated from the residue. Purification by reverse phase HPLC eluting with 0–15% acetonitrile in ammonium acetate (0.01N) gave the title compound (42 mg, 48%)

$^1$H NMR (300 MHz, D$_2$O+NaOD) δ: 8.17 (s, 1 H, H-8'), 7.99 (s, 1 H, H-2'), 4.10 (m, 2 H, H-6), 4.03 (m, 1 H, H-5), 3.62 (br t, 1 H, H-2)1.85 (m, 3 H), 1.56 (m, 1 H).

$^{13}$C NMR (75.5 MHz, D$_2$O+NaOD) δ: 156.1, 152.9, 149.5, 144.3, 118.8, 78.9 (d, J$_{p-c}$=157 Hz), 78.7 (d, J$_{p-c}$=9 Hz), 48.4, 29.4 (d, J$_{p-c}$=7 Hz), 28.0.

$^{31}$P NMR (101.2 MHz, D$_2$O+NaOD) δ: 15.93.

Example 65

(±)-TRANS-5-(ADENIN-9'-YLMETHYL)-2-DIHYDROXYPHOSPHINOYL-TETRAHYDROFURAN

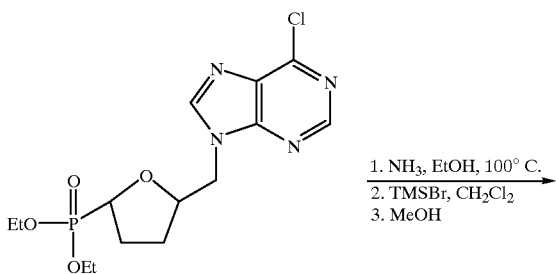

-continued

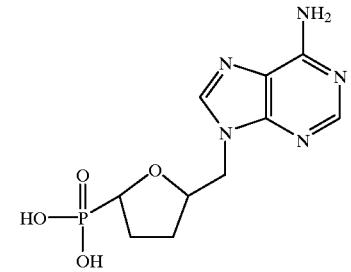

An ice-cold solution of (±)-trans-5-(6'-chloropurin-9'-ylmethyl)-2-diethoxyphosphinoyl-tetrahydrofuran (example 63) (174 mg, 0.46 mmol) in EtOH (20 mL) was saturated with ammonia. The solution was then heated at 100° C. in a steel bomb for 16 h. The bomb was then cooled in ice and vented. Concentration of the solution gave a residue which was dissolved in dry methylene chloride (5 mL) and treated with TMSBr (0.61 mL, 4.60 mmol). The reaction mixture was then allowed to stir at rt for 16 h. The mixture was concentrated to dryness and methanol (3×5 mL) was evaporated from the residue. Purification by reverse phase HPLC eluting with 0–15% acetonitrile in ammonium acetate (0.01N) gave the title compound (94 mg, 68%)

$^1$H NMR (300 MHz, D$_2$O+NaOD) δ: 7.99 (s., 1 H, H-8'), 7.94 (s, 1 H, H-2'), 4.20 (m, 1 H, H-5), 4.06 (m, 2 H, H-6), 3.60 (t, 1 H, H-2, J=8.2 Hz), 1.88 (m, 1 H), 1.75 (m, 2 H), 1.30 (m, 1 H).

$^{13}$C NMR (75.5 MHz, D$_2$O+NaOD) δ: 156.0, 152.9, 149.6, 143.9, 118.6, 78.4 (d, J$_{P-C}$=7 Hz), 77.9 (d, J$_{P-C}$=157 Hz), 47.3, 29.5 (d, J$_{P-C}$=7 Hz), 28.6.

$^{31}$P NMR (101.2 MHz, D$_2$O+NaOD) δ: 16.75.

Example 66

(±)-CIS AND TRANS-5-BROMOMETHYL-2-DIETHOXYPHOSPHINOYL-TETRAHYDROFURAN

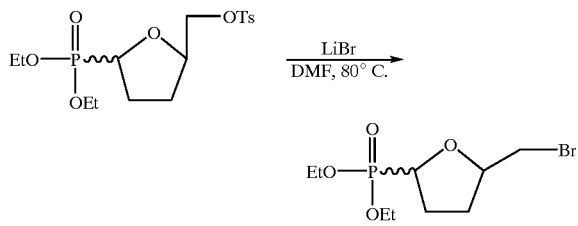

To a stirring solution of (±)-2-diethoxyphosphinoyl-5-(p-toluenesulfonyloxymethyl)-tetrahydrofuran (example 60) (12.0 g, 30.61 mmol) in dry DMF (60 mL) was added anhydrous lithium bromide (13.3 g, 153.05 mmol). The solution was then stirred at 80° C. for 4 h. The mixture was cooled and concentrated to dryness under reduced pressure. The residue was then dissolved in methylene chloride and the solution was washed with water (2×50 mL), brine (50 mL), dried (MgSO$_4$) and concentrated. The cis-trans mixture was separated by flash chromatography eluting with 10→20% acetone in hexanes.

Cis isomer (3.825 g, 42%).

$^1$H NMR (300 MHz, CDCl$_3$) δ: 4.15 (m, 6 H, 2 CH$_2$CH$_3$, H-2, H-5), 3.47 (dd, 1 H, H-6, J=5.4 HZ and 10.1 Hz), 3.34 (dd, 1 H, H-6$_a$, J=7.4 HZ and 10.1 Hz), 2.1 (m, 4 H, H-3 and H-4), 1.33, 1.32 (2 t, 6 H, 2 CH$_2$CH$_3$, J=7.1 Hz).

Trans isomer (4.124 g, 45%).

$^1$H NMR (300 MHz, CDCl$_3$) δ: 4.31 (M, 1 H), 4.25 (m, 1 H), 4.13 (m, 4 H, 2 CH$_2$CH$_3$), 3.44 (dd, 1 H, H-6, J=4.4 HZ and 10.4 Hz), 3.36 (dd, 1 H, H-6$_a$, J=6.5 HZ and 10.4 Hz), 2,22 (m, 3 H), 1.32, 1.31 (2 t, 6 H, 2 CH$_2$CH$_3$, J=7.1 Hz).

Example 67

(±)-CIS-5-(2'-AMINO-6'-CHLOROPURIN-9'-YLMETHYL)-2-DIETHOXYPHOSPHINOYL-TETRAHYDROFURAN

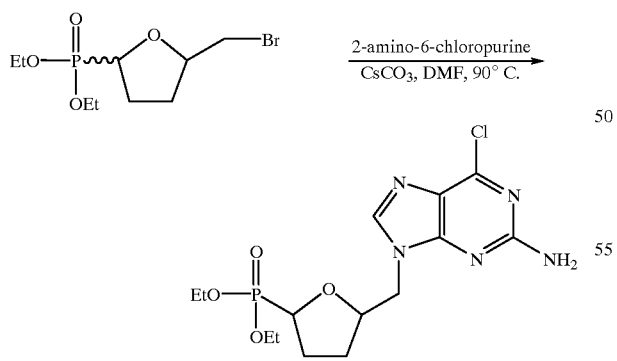

A mixture of (±)-cis-5-bromomethyl-2-diethoxyphosphinoyl-tetrahydrofuran (example 66) (544 mg, 1.81 mmol), 2-amino-6-chloropurine (368 mg, 2.17 mmol) and cesium carbonate (885 mg, 2.72 mmol) in dry DMF (2 mL) was stirred at 90° C. for 6 h. The mixture was then cooled and filtered. Concentration of the filtrate gave a residue which was purified by chromatography eluting with 2→5% MeOH in methylene chloride. The desired product was obtained as a foam (357 mg, 51%).

$^1$H NMR (300 MHz, CDCl$_3$) δ: 8.05 (s, 1 H, H-8'), 5.15 (br s, 2 H, NH$_2$), 4.36 (m, 1 H), 4.15 (m, 5 H), 2.23 (m, 2 H), 2.10 (m, 1 H), 1.90 (m, 1 H) 1.31, 1.28 (2 t, 6 H, 2 CH$_2$CH$_3$, J=7.1 Hz).

Example 68

(±)-TRANS-5-(2'-AMINO-6'-CHLOROPURIN-9'-YLMETHYL)-2-DIETHOXYPHOSPHINOYL-TETRAHYDROFURAN

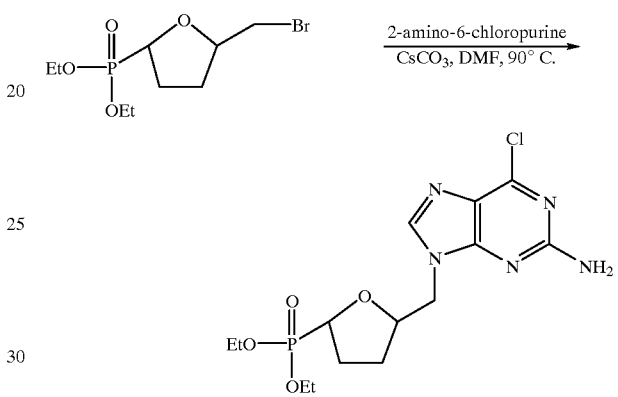

A mixture of (±)-trans-5-bromomethyl-2-diethoxyphosphinoyl-tetrahydrofuran (example 66) (529 mg, 1.76 mmol), 2-amino-6-chloropurine (358 mg, 2.11 mmol) and cesium carbonate (860 mg, 2.64 mmol) in dry DMF (2 mL) was stirred at 90° C. for 6 h. The mixture was then cooled and filtered. Concentration of the filtrate gave a residue which was purified by chromatography eluting with 2→5% MeOH in methylene chloride. The desired product was obtained as a foam (384 mg, 56%).

$^1$H NMR (300 MHz, CDCl$_3$) δ: 7.89 (s, 1 H, H-8'), 5.14 (br s, 2 H, NH$_2$), 4.42(m, 1 H), 4.15 (m, 5 H), 2.15 (m, 3 H), 1.50 (m, 1 H), 1.28 (t, 6 H, 2 CH$_2$CH$_3$, J=7.1 Hz).

Example 69

(±)-CIS-5-(2'-AMINO-6'-CHLOROPURIN-9'-YLMETHYL)-2-DIHYDROXYPHOSPHINOYL-TETRAHYDROFURAN, MONOAMMONIUM SALT

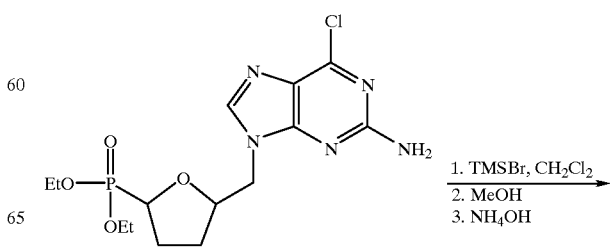

-continued

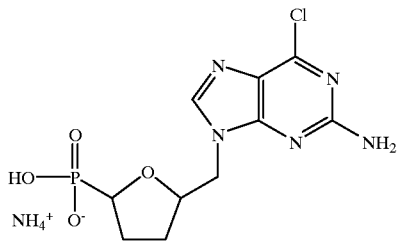

To a stirring solution of (±)-cis-5-(2'-amino-6'-chloropurin-9'-ylmethyl)-2-diethoxyphosphinoyl-tetrahydrofuran (example 67) (125 mg, 0.32 mmol) in dry methylene chloride (3 mL) was added TMSBr (0.42 mL, 3.2 mmol). After stirring overnight at rt, the reaction mixture was concentrated to dryness and methanol (3×2 mL) was evaporated from the residue. The residue was then dissolved in 0.5 N ammonium hydroxide and lyophilized. The resulting solid was then applied on a A-25 SEPHADEX (microscopic polysaccharide dextran derivative beads) column eluting with 0→0.3 N ammonium bicarbonate. After concentration of the appropriate fractions, the residue was purified by $C_{18}$ reverse phase HPLC eluting with water.

$^1$H NMR (300 MHz, $D_2O$) δ: 8.09 (s, 1 H, H-8'), 4.32 (m, 1 H, H-5), 4.12 (2 H, H-6), 3.98 (t, 1 H, H-2, J=8.0 Hz), 1.90 (m, 3 H), 1.48 (m, 1 H). UV λmax ($H_2O$) 246 nm, 305 nm.

Example 70

(±)-TRANS-5-(2'-AMINO-6'-CHLOROPURIN-9'-YL)METHYL-2-DIHYDROXYPHOSPHINOYL-TETRAHYDROFURAN MONOAMMONIUM SALT

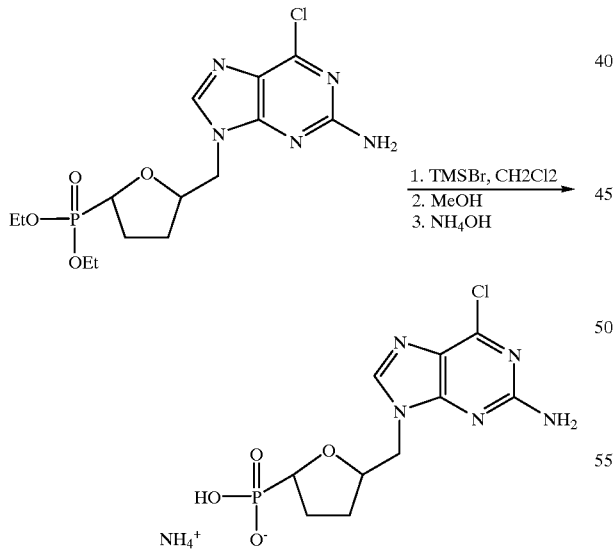

To a stirring solution of (±)-trans-5-(2'-amino-6'-chloropurin-9'-ylmethyl)-2-diethoxyphosphinoyl-tetrahydrofuran (example 68) (125 mg, 0.32 mmol) in dry methylene chloride (3 ml) was added TMSBr (0.42 ml, 3.2 mmol). After stirring overnight at rt, the reaction mixture was concentrated to dryness and methanol (3×2 ml) was evaporated from the residue. Re-crystallization from water gave a beige solid (77 mg, 72%). An aliquot (24 mg) was dissolved in water (5 ml) containing a few drops of concentrated ammonium hydroxide. The solution was then lyophilized giving the title compound $^1$H NMR (300 MHz, $D_2O$) δ: 8.09 (s, 1 H, H-8'), 4.32 (m, 1 H, H-5), 4.12 (2 H, H-6), 3.98 (t, 1 H, H-2, J=8.0 Hz), 1.90 (m, 3 H), 1.48 (m, 1 H). UV λmax ($H_2O$) 247 nm, 307 nm.

Example 71

(±)-TRANS-2-DIHYDROXYPHOSPHINOYL-5-(GUANIN-9'-YLMETHYL)-TETRAHYDROFURAN, MONOAMMONIUM SALT (BCH-1573)

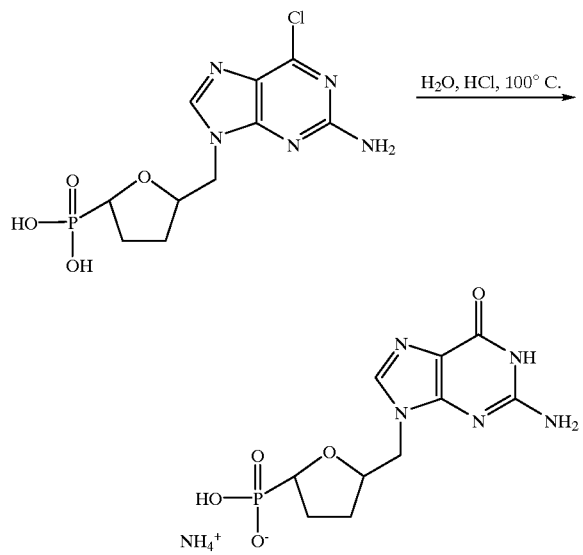

A solution of (±)-trans-5-(2'-amino-6'-chloropurin-9'-ylmethyl)-2-dihydroxyphosphinoyl-tetrahydrofuran (example 70) (67 mg, 0.20 mmol) in water (5 mL) and 0.1 N HCl (2 mL) was refluxed overnight. The solution was concentrated to dryness and the residue was applied on a A-25 SEPHADEX (microscopic polysaccharide dextran derivative beads) column eluting with 0→0.4 M ammonium bicarbonate. After concentration of the appropriate fractions, the residue was further purified by $C_{18}$ reverse phase HPLC eluting with 0–15% acetonitrile in ammonium acetate (0.01N).

$^1$H NMR (300 MHz, $D_2O$) δ: 7.69 (s, 1 H, H-8'), 4.27 (m, 1 H, H-5), 3.99 (m, 2 H, H-6), 3.83 (t, 1 H, H-2, J=8.0 Hz), 1.80–2.05 (m, 3 H), 1.48 (m, 1 H). UV λ$_{max}$ ($H_2O$) 252 nm.

Example 72

(±)-CIS-2-DIHYDROXYPHOSPHINOYL-5-(GUANIN-9'-YLMETHYL)-TETRAHYDROFURAN, MONOAMMONIUM SALT (BCH-1570)

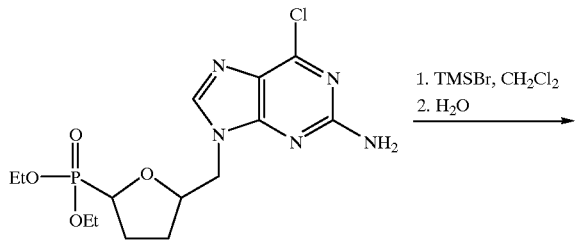

1. TMSBr, CH₂Cl₂
2. H₂O

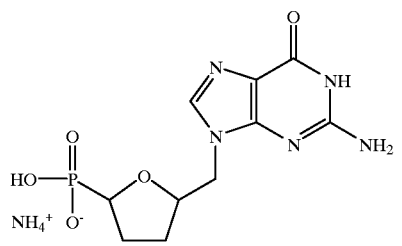

To a stirring solution of (±)-cis-5-(2'-amino-6'-chloropurin-9'-ylmethyl)-2-diethoxyphosphinoyl-tetrahydrofuran (example 67) (125 mg, 0.32 mmol) in dry methylene chloride (3 mL) was added TMSBr (0.42 mL, 3.2 mmol). After stirring overnight at rt, the reaction mixture was concentrated to dryness and methanol (3×2 mL) was evaporated from the residue. Attempts to re-crystallize from water resulted in the partial conversion to the guanine derivative. Therefore, a solution of the crude mixture in water (5 mL) was refluxed for 4 h. The solution was then applied on a A-25 SEPHADEX(microscopic polysaccharide dextran derivative beads) column eluting with 0→0.4 M ammonium bicarbonate. After concentration of the appropriate fractions, the residue was further purified by C₁₈ reverse phase HPLC eluting with 0→25% acetonitrile in ammonium acetate (0.01N).

¹H NMR (300 MHz, D₂O) δ: (7.77, 1 H, H-8'), 4.11 (m, 1 H, H-5), 3.92 (m, 2 H, H-6), 3.73 (t, 1 H, H-2, J=8.2 Hz), 1.91 (m, 3 H), 1.64 (m, 1 H). UV $\lambda_{max}$ (H₂O) 251 nm.

Example 73

(±)-TRANS-2-DIHYDROXYPHOSPHINOYL-5-(2',6'-DIAMINOPURIN-9'-YLMETHYL)-TETRAHYDROFURAN, MONOAMMONIUM SALT (BCH-1572)

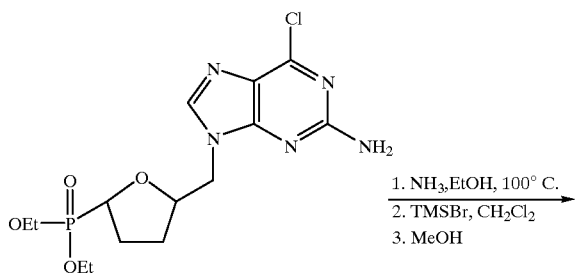

1. NH₃, EtOH, 100° C.
2. TMSBr, CH₂Cl₂
3. MeOH

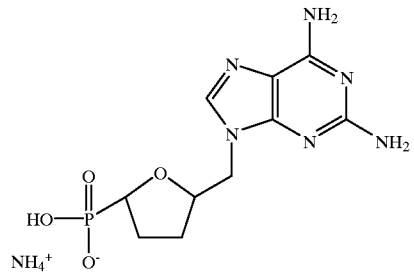

An ice-cold solution of (±)-trans-5-(2'-amino-6'-chloropurin-9'-ylmethyl)-2-diethoxyphosphinoyl-tetrahydrofuran (example 68) (124 mg, 0.32 mmol) in EtOH (20 mL) was saturated with ammonia. The solution was then heated at 100° C. in a steel bomb for 16 h. The bomb was then cooled in ice and vented. Concentration of the solution gave a residue which was dissolved in dry methylene chloride (2.5 mL) and treated with TMSBr (0.42 mL, 3.20 mmol). The reaction mixture was then allowed to stir at rt for 16 h. The mixture was concentrated to dryness and methanol (3×2 mL) was evaporated from the residue. An aqueous solution of the residue was then applied on a A-25 SEPHADEX(microscopic polysaccharide dextran derivative beads) column eluting with 0→0.3 M ammonium bicarbonate. After concentration of the appropriate fractions, the residue was further purified by C₁₈ reverse phase HPLC eluting with 0–25% acetonitrile in ammonium acetate (0.01N).

¹H NMR (300 MHz, D₂O) δ: 7.75 (s, 1 H, H-8'), 4.24 (m, 1 H, H-5), 4.99 (m, 2 H, H-6), 3.71 (t, 1 H, H-2 J=8.8 Hz), 1.75–1.95 (m, 3 H), 1.39 (m, 1 H).

UV $\lambda_{max}$ (H₂O) 254 nm, 279 nm.

Example 74

(±)-CIS-2-DIHYDROXYPHOSPHINOYL-5-(2',6'-DIAMINOPURIN-9'-YLMETHYL)-TETRAHYDROFURAN, MONOAMMONIUM SALT

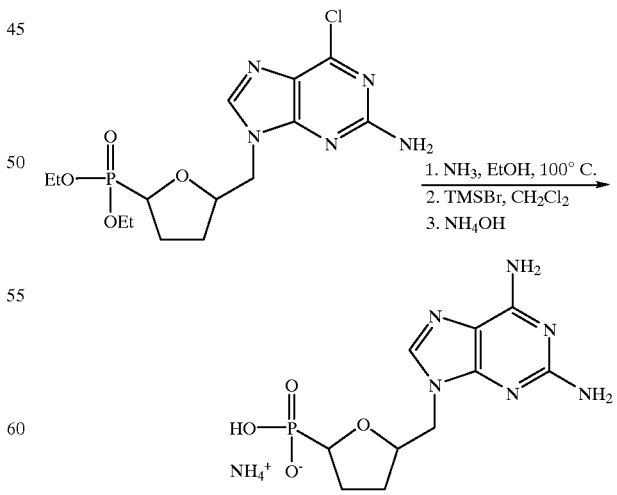

1. NH₃, EtOH, 100° C.
2. TMSBr, CH₂Cl₂
3. NH₄OH

An ice-cold solution of (±)-cis-5-(2'-amino-6'-chloropurin-9'-ylmethyl)-2-diethoxyphosphinoyl-tetrahydrofuran (example 67) (237 mg, 0.61 mmol) in EtOH (20 ml) was saturated with ammonia. The solution was then heated at 100° C. in a steel bomb for 16 h. The bomb was cooled in ice and vented. Concentration of the solution gave a residue which was dissolved in dry methylene chloride (5 ml) and treated with TMSBr (0.80 ml, 6.08 mmol). After stirring for 16 h at rt, the mixture was concentrated to dryness and the residue was dissolved in water (10 ml). The solution was made basic with ammonium hydroxide and it was then washed with dichloromethane (3×5 ml) and pentane (5 ml). Lyophilization followed by purification on $C_{18}$ reverse phase HPLC eluting with 0–25% acetonitrile in ammonium acetate (0.01N) gave the desired compound as a white solid (90 mg, 45%).

$^1$H NMR (300 MHz, $D_2O$) δ: 7.72 (s, 1 H, H-8'), 4.16 (m, 1 H, H-5), 3.92 (m, 2 H, $H6_{a, b}$), 3.82 (t, 1 H, H-2, J=8.4 Hz), 1.96 (m, 3 H), 1.72 (m, 1 H).

$^{13}$C NMR (75.5 MHz, $D_2O$) δ:159.4, 156.1, 150.5, 141.2, 113.0, 79.6 (d, J=8.0 Hz), 77.4 (d, J=160.5 Hz), 48.4, 29.3 (d, J=7.3 Hz), 27.6. UV $\lambda_{max}$ ($H_2O$) 254 and 279 nm.

Example 75

(±)-CTS-2-DIETHOXYPHOSPHINOYL-5-(THYMIN-1'-YLMETHYL)-TETRAHYDROFURAN

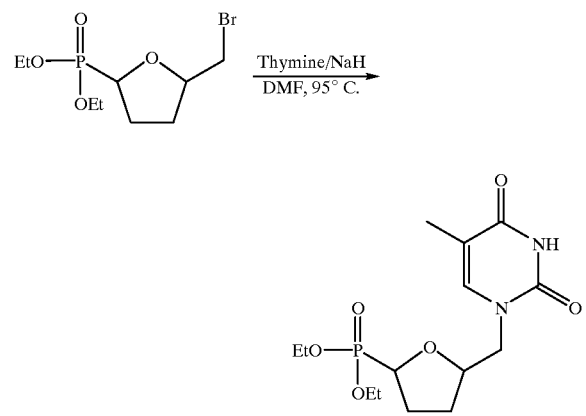

To a stirring suspension of thymine (551 mg, 3.32 mmol) in dry DMF (3 mL) was added sodium hydride (60% oil dispersion, 133 mg, 3.32 mmol). After stirring the mixture for 30 min at room temperature, a solution of cis-5-bromomethyl-2-diethoxyphosphinoyl-tetrahydrofuran (example 66) (500 mg, 1.66 mmol) in DMF (3 mL) was added via cannula. The mixture was then stirred at 90° C. for 15 h after which the mixture was cooled and quenched with saturated ammonium chloride (5 mL). The volatiles were removed under vacuo and the residue was dissolved in a mixture of dichloromethane (20 mL) and water (10 mL). The mixture was filtered and the aqueous layer was collected and extracted with dichloromethane (2×20 mL). The combined extracts were then washed with brine (20 mL), dried ($MgSO_4$) and concentrated to dryness. Purification by chromatography eluting with EtAc, 5% MeOH in EtAc then 10% MeOH in EtAc yielded first $N^1$-ethyl thymine (102 mg, 40%) and then the title compound as an oil (126 mg, 22%).

$^1$H NMR (300 MHz, $CDCl_3$) δ: 8.46 (br s, 1 H, NH), 7.55 (d, 1 H, H-6', J=1.2 Hz), 4.39 (m, 1 H, H-5), 4.15 (m, 6 H, 2 C$\underline{H}_2$CH$_3$, H-2 and H-6$_a$), 3.40 (dd, 1 H, H-6$_b$, J=9.5 HZ and 13.8 Hz), 2.20 (m, 4 H, H-3 and H-4), 1.87 (d, 1 H, thymine-CH$_3$, J=1.1 Hz), 1.33 (t, 6 H, 2 CH$_2$CH$_3$, J=7.1 Hz).

Example 76

(±)-TRANS-2-DIETHOXYPHOSPHINOYL-5-(THYMIN-1'-YLMETHYL)-TETRAHYDROFURAN

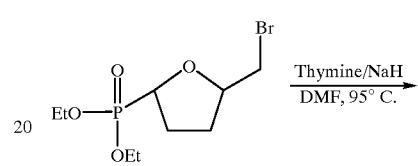

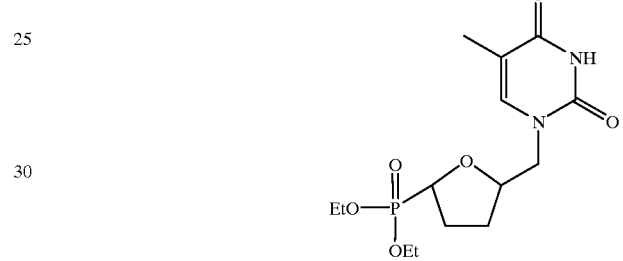

To a stirring suspension of thymine (536 mg, 4.18 mmol) in dry DMF (5 mL) was added sodium hydride (60% oil dispersion, 167 mg, 4.18 mmol). After stirring the mixture for 30 min at room temperature, a solution of trans-5-bromomethyl-2-ethoxyphosphinoyl-tetrahydrofuran (example 66) (630 mg, 2.09 mmol) in DMF (3 mL) was added via cannula. The mixture was then stirred at 90° C. for 18 h after which the mixture was cooled and quenched with saturated ammonium chloride (5 mL). The volatiles were removed under vacuo and the residue was dissolved in a mixture of dichloromethane (20 mL) and water (10 mL). The mixture was filtered and the aqueous layer was collected and extracted with dichloromethane (2×20 mL). The combined extracts were then washed with brine (20 mL), dried ($MgSO_4$) and concentrated to dryness. Purification by chromatography eluting with EtAc, 5% MeOH in EtAc then 10% MeOH in EtAc yielded first $N^1$-ethyl thymine (83 mg, 26%) and then the title compound as an oil (186 mg, 26%).

$^1$H NMR (300 MHz, $CDCl_3$) δ: 9.50 (br s, 1 H, NH), 7.11 (d, 1 H, H-6', J=1.2 Hz), 4.28 (m, 1 H, H-5), 4.1 (m, 5 H, 2 C$\underline{H}_2$CH$_3$, H-2), 3.96 (dd, 1 H, H-6$_a$, J=2.7 HZ and 14.4 Hz), 3.66 (dd, 1 H, H-6$_b$, J=6.6 HZ and 14.4 Hz), 2.19 (m, 4 H, H-3 and H-4), 1.85 (d, 1 H, thymine-CH$_3$, J=1.1 Hz), 1.28 (t, 6 H, 2 CH$_2$CH$_3$, J=7.1 Hz).

Example 77

(±)-CIS-2-DIHYDROXYPHOSPHINOYL-5-(THYMIN-1'-YLMETHYL)-TETRAHYDROFURAN, MONOAMMONIUM SALT

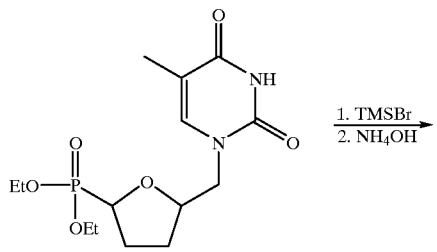

To a solution of (±)-cis-2-diethoxyphosphinoyl-5-(thymin-1'-ylmethyl)-tetrahydrofuran (example 75) (120 mg, 0.35 mmol) in dry dichloromethane (5 mL) was added TMSBr (0.46 mL, 3.50 mmol). The solution was stirred overnight at rt and the solution was concentrated to dryness. The residue was dissolved in water (10 mL) and the solution was made basic by addition of ammonium hydroxide (1 N). The solution was lyophilized and purified by $C_{18}$ reverse phase HPLC eluting with 0–15% acetonitrile in ammonium acetate (0.01 M). The appropriate fractions were combined and made basic with ammonium hydroxide. Lyophilization gave the required product as a white solid (60 mg, 56%).

$^1$H NMR (300 MHz, $D_2O$) δ: 7.55 (s, 1 H, H-6'), 4.01 (m, 1 H, H-5), 3.84 (dd, 1 H, H-$6_a$, J=3.4 HZ and 14.3 Hz), 3.72 (t, 1 H, H-2, J=7.6 Hz), 3.54 (dd, 1 H, H-$6_b$, J=8.5 HZ and 14.3 Hz), 1.93 (m, 3 H), 1.70 (s, 3 H, $CH_3$), 1.58 (m, 1H).

$^{13}$C NMR (75.5 MHz, $D_2O$) δ: 167.7, 153.0, 144.9, 110.9, 78.8, 77.7 (d, J=147.2 Hz), 52.8, 29.3, (d, J=6.6 Hz), 27.5, 11.9. UV λmax ($H_2O$) 266 nm.

Example 78

(±)-TRANS-2-DIHYDROXYPHOSPHINOYL-5-(THYMIN-1'-YLMETHYL)-TETRAHYDROFURAN MONOAMMONIUM SALT

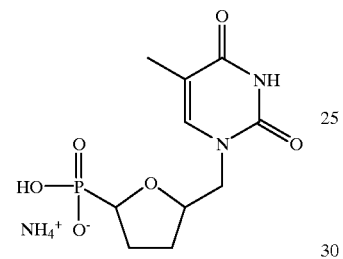

To a solution of (±)-trans-2-diethoxyphosphinoyl-5-(thymin-1'-ylmethyl)-tetrahydrofuran (example 76) (180 mg, 0.52 mmol) in dry dichloromethane (5 mL) was added TMSBr (0.69 mL, 5.20 mmol). The solution was stirred overnight at rt and the solution was concentrated to dryness. The residue was dissolved in water (10 mL) and the solution was made basic by addition of ammonium hydroxide (1 N). The solution was lyophilized and purified by $C_{18}$ reverse phase HPLC eluting with 0–15% acetonitrile in ammonium acetate (0.01 M). The appropriate fractions were combined and made basic with ammonium hydroxide. Lyophilization gave the required product as a white solid (32 mg, 20%).

$^1$H NMR (300 MHz, $D_2O$) δ: 7.36 (s, 1 H, H-6'), 4.12 (m, 1 H, H-5), 3.66 (m, 3 H), 1.93 (m , 2 H), 1.82 (m, 1 H), 1.70 (s, 3 H, $CH_3$), 1.44 (m, 1H). UV λmax ($H_2O$) 272 nm

Example 79

(±)-CIS-2-DIETHOXYPHOSPHINOYL-5-(URACIL-1'-YLMETHYL)-TETRAHYDROFURAN

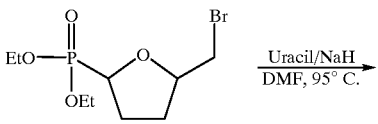

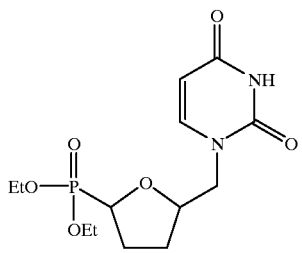

To a stirring suspension of uracil (372 mg, 3.32 mmol) in dry DMF (15 mL) was added sodium hydride (60% oil dispersion, 133 mg, 3.32 mmol). After stirring the mixture for 30 min at room temperature, a solution of cis-5-bromomethyl-2-diethoxyphosphinoyl-tetrahydrofuran (example 66) (500 mg, 1.66 mmol) in DMF (3 mL) was added via cannula. The mixture was then stirred at 90° C. for 15 h after which the mixture was cooled and quenched with saturated ammonium chloride (5 mL). The volatiles were removed under vacuo and the residue was dissolved in a mixture of dichloromethane (20 mL) and water (10 mL). The mixture was filtered and the aqueous layer was collected and extracted with dichloromethane (2×20 mL). The combined extracts were then washed with brine (20 mL), dried (MgSO$_4$) and concentrated to dryness. Purification by chromatography eluting with 10% MeOH in EtAc yielded the title compound as an oil (129 mg, 23%).

$^1$H NMR (300 MHz, CDCl$_3$) δ: 9.46 (br s, 1 H, NH), 7.73 (d, 1 H, H-6', J=7.9 Hz), 5.59 (d, 1 H, H-5', J=7.9), 4.40 y(m, 1 H, H-5), 4.13 (m, 6 H, 2 C$\underline{H}_2$CH$_3$, H-2, H-6$^a$), 3.41 (dd, 1 H, H-6$^b$, J=9.6 HZ and 13.8 Hz), 2.17 (m, 2 H), 2.15 (m, 1 H), 1.85 (m, 1 H), 1.30 (t, 6 H, 2 CH$_2$C$\underline{H}_3$, J=7.2 Hz).

Example 80

(±)-TRANS-2-DIETHOXYPHOSPHINOYL-5-(URACIL-1'-YLMETHYL)-TETRAHYDROFURAN

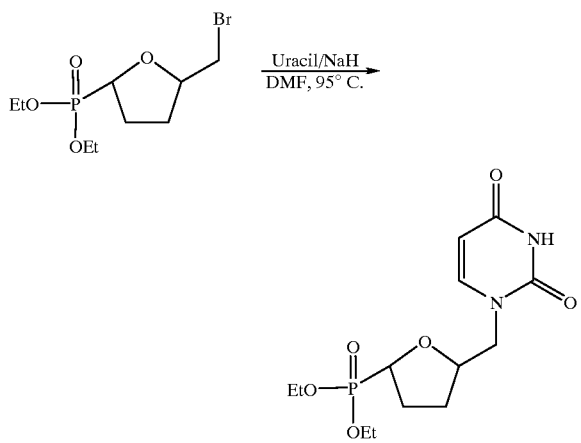

To a stirring suspension of uracil (468 mg, 4.18 mmol) in dry DMF (15 mL) was added sodium hydride (60% oil dispersion, 167 mg, 4.18 mmol). After stirring the mixture for 30 min at room temperature, a solution of trans-5-bromomethyl-2-diethoxyphosphinoyl-tetrahydrofuran (example 66) (630 mg, 2.09 mmol) in DMF (5 mL) was added via cannula. The mixture was then stirred at 90° C. for 18 h after which the mixture was cooled and quenched with saturated ammonium chloride (5 mL). The volatiles were removed under vacuo and the residue was dissolved in a mixture of dichloromethane (20 mL) and water (10 mL). The mixture was filtered and the aqueous layer was collected and extracted with dichloromethane (2×20 mL). The combined extracts were then washed with brine (20 mL), dried (MgSO$_4$) and concentrated to dryness. Purification by chromatography eluting with 10% MeOH in EtAc yielded the title compound as an oil (282 mg, 41%).

$^1$H NMR (300 MHz, CDCl$_3$) δ: 9.03 (br s, 1 H, NH), 7.31 (d, 1 H, H-6', J=7.9 Hz), 5.64 (dd, 1 H, H-5', J=1.4 HZ and 8.0 Hz), 4.42 (m, 1 H, H-5), 4.12 (m, 5 H, 2 C$\underline{H}_2$CH$_3$, H-2), 4.00 (dd, 1 H, H-6$^a$, J=2.7 HZ and 14.1 Hz), 3.72 (dd, 1 H, H-6$^b$, J=6.3 HZ and 14.1 Hz), 2.20 (m, 3 H), 1.48 (m, 1 H), 1.30 (t, 6 H, 2 CH$_2$C$\underline{H}_3$, J=7.1 Hz).

Example 81

(±)-CIS-2-DIHYDROXYPHOSPHINOYL-5-(URACIL-1'-YLMETHYL)-TETRAHYDROFURAN, MONOAMMONIUM SALT

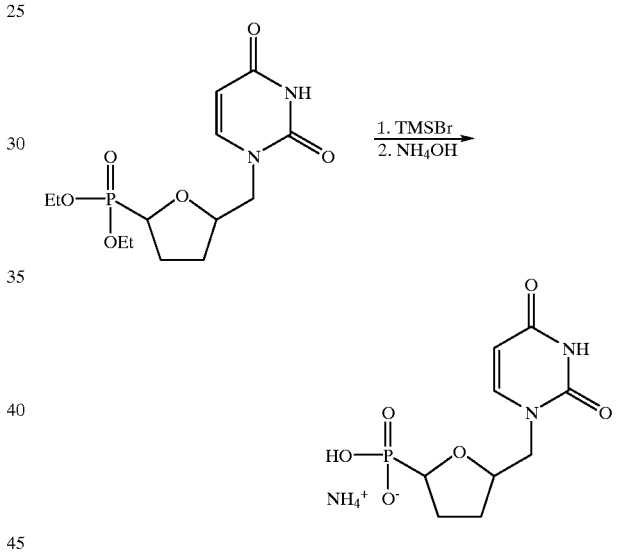

To a solution of (±)-cis-2-diethoxyphosphinoyl-5-(uracil-1'-ylmethyl)-tetrahydrofuran (example 79) (120 mg, 0.36 mmol) in dry dichloromethane (5 mL) was added TMSBr (0.48 mL, 3.60 mmol). The solution was stirred overnight at rt and the solution was concentrated to dryness. The residue was dissolved in water (10 mL) and the solution was made basic by addition of ammonium hydroxide (1 N). The solution was lyophilized and purified by C$_{18}$ reverse phase HPLC eluting with 0–15% acetonitrile in ammonium acetate (0.01 M). The appropriate fractions were combined and made basic with ammonium hydroxide. Lyophilization gave the required product as a white solid (92 mg, 87%).

$^1$H NMR (300 MHz, D$_2$O) δ: 7.70 (d, 1 H, H-6', J=7.9 Hz), 5.60 (d, 1 H, H-5', J=7.9 Hz), 4.03 (m, 1 H, H-5), 3.87 (dd, 1 H, H-6$^a$, J=3.0 HZ and 14.2 Hz), 3.72 (t, 1 H, H-2, J=8.0 Hz), 3.48 (dd, 1 H, H-6$^b$, J=8.9 HZ and 14.1 Hz), 1.88 (m, 3 H), 1.59 (m, 1H).

$^{13}$C NMR (75.5 MHz, D$_2$O) δ: 167.5, 152.9, 149.3, 101.6, 78.6 (d, J=5.5 Hz), 77.5 (d, J=148.2 Hz), 29.2, (d, J=7.0 Hz), 27.5. UV λmax (H$_2$O) 266 nm

Example 82

(±)-TRANS-2-DIHYDROXYPHOSPHINOYL-5-(URACIL-1'-YLMETHYL)-TETRAHYDROFURAN, MONOAMMONIUM SALT

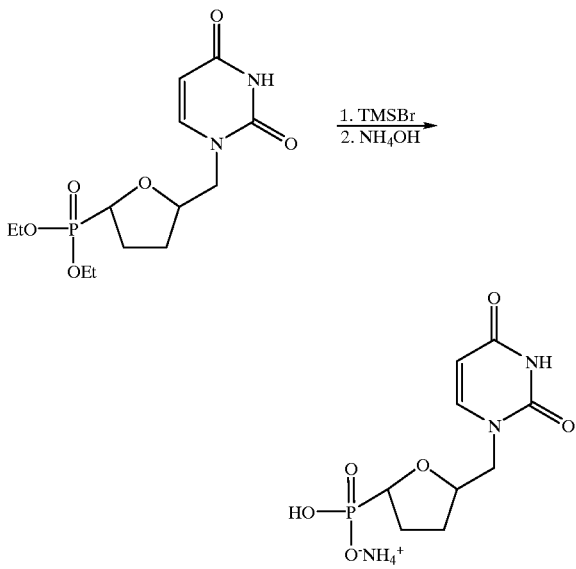

To a solution of (±)-trans-2-diethoxyphosphinoyl-5-(uracil-1'-ylmethyl)-tetrahydrofuran (example 80) (270 mg, 0.81 mmol) in dry dichloromethane (8 mL) was added TMSBr (1.10 mL, 8.10 mmol). The solution was stirred overnight at rt and the solution was concentrated to dryness. The residue was dissolved in water (10 mL) and the solution was made basic by addition of ammonium hydroxide (1 N). The solution was lyophilized and purified by $C_{18}$ reverse phase HPLC eluting with 0–15% acetonitrile in ammonium acetate (0.01 M). The appropriate fractions were combined and made basic with ammonium hydroxide. Lyophilization gave the required product as a white solid (180 mg, 76%).

$^1$H NMR (300 MHz, D$_2$O) δ: 7.51 (d, 1 H, H-6', J=8.0 Hz), 5.63 (d, 1 H, H-5', J=8.0 Hz), 4.13 (m, 1 H, H-5), 3.72 (m, 2 H), 3.64 (dd, 1 H, H-7, J=7.2 HZ and 14.4 Hz), 1.93 (m, 2 H), 1.83 (m, 1 H), 1.44 (m, 1H).

$^{13}$C NMR (75.5 MHz, D$_2$O) δ: 167.5, 153.2, 148.7, 101.8, 78.4 (d, J=7.8 Hz), 76.8 (d, J=159.0 Hz), 51.6, 29.4 (J=7.0 Hz), 28.3. UV λmax (H$_2$O) 267 nm.

Example 83

CIS AND TRANS 4-(BROMOMETHYL)-2-(DIETHYLOXYPHOSPHINOYLMETHYL)-1,3-DIOXOLANE

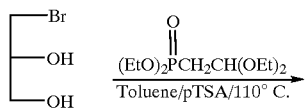

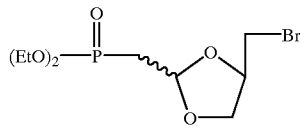

To a solution of diethylphosphonoacetaldehyde diethylacetal (15.00 g, 59.0 mmol) and 3-bromo-1,2-propanediol (11.00 g, 71.0 mmol, 1.2 eq.) in toluene (60 mL) was added pTSA (few cristals). The mixture was stirred at reflux for 72 hr and was cooled to room temperature. A saturated solution of sodium bicarbonate was added and the aqueous phase was extracted with dichloromethane. The organic phase was dried over anhydrous sodium sulphate and evaporated under reduced pressure. The crude material was pure by TLC and NMR and gave 17.93 g of the compound in a 96% yield.

$^1$H NMR (300 MHz, CDCl$_3$) δ: 1.33 (t, 6H, J=7.0 Hz, CH$_3$), 2.20 (dd, 0.66H, J=5.4 Hz, $^2$J$_{HP}$=17 Hz, CH$_2$P for trans), 2.25 (dd, 1.33H, J=5.2 Hz, $^2$J$_{HP}$=18.7 Hz, CH$_2$P for cis), 3.32 (dd, 1H, J=7.9 Hz, 10.2 Hz, CH$_A$H$_B$Br), 3.42 and 3.48 (2dd, 1H, J=4.8 Hz, 10.2 Hz, CH$_A$H$_B$Br), 3.74 (dd, 0.33H, J=6.4 Hz, 8.8 Hz, H-5a for trans), 3.98 (d, 1.33H, J=5.2 Hz, H-5 for cis), 4.13 (m, 4H, CH$_2$), 4.26 (dd, 0.33H, J=6.2 Hz, 8.7 Hz, H-5b for trans), 4.35 (m, 1H, H-4), 5.24 (dt, 0.66H, J=5.2 Hz, $^3$J$_{HP}$=4.7 Hz, H-2 for cis), 5.37 (dt, 0.33H, J=5.2 Hz, $^3$J$_{HP}$=5.2 Hz, H-2 for trans).

Example 84

CIS AND TRANS-4-(2'-AMINO-6'-CHLOROPURIN-9'-YLMETHYL)-2-(DIETHYLOXYPHOSPHINOYLMETHYL)-1,3-DIOXOLANE

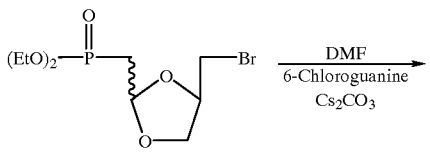

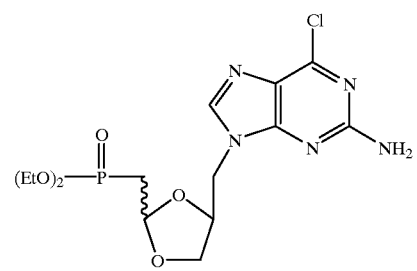

To a solution of cis and trans-4-(bromomethyl)-2-(diethyloxyphosphinoylmethyl)-1,3-dioxolane (example 83) (1.01 g, 3.19 mmol) and 6-chloroguanine (588 mg, 3.47 mmol, 1.1 eq.) in DMF (75 mL) was added Cs$_2$CO$_3$ (2.05 g, 6.31 mmol, 2 eq.). The mixture was stirred at 70° C. for 22 hr. After, the solution was cooled to room temperature, the solid was filtered and washed with DMF. The solvent was evaporated under reduced pressure. The crude material was purified by flash chromatography with a mixture of dichloromethane and methanol (95:5) to give the compound (722 mg) in 56% yield.

$^1$H NMR (300 MHz, CDCl$_3$) δ: 1.33 (m, 6H, CH$_3$), 2.20 (dm, 2H, $^2$J$_{HP}$=18.6 Hz, CH$_2$P), 3.65 (dd, 0.33H, J=7.5 Hz, 9.0 Hz, H-5a for trans), 3.91 (dd, 0.66H, J=4.5 Hz, 9.0 Hz, H-5a for cis), 3.98 (dd, 0.66H, J=7.0 Hz, 8.9 Hz, H-5b for cis), 4.12 (m, 4H, CH$_2$, and 0.33H, H-5b for trans), 4.27 (m, 2H, CH$_2$N), 4.50 (m, 1H, H-4), 5.09 and 5.13 (bs, 2H, NH$_2$), 5.18 (dt, 0.66H, J=6.1 Hz, $^3$J$_{HP}$=6.1 Hz, H-2 for cis), 5.34 (dt, 0.33H, J=5.2 Hz, $^3$J$_{HP}$=5.2 Hz, H-2 for trans), 7.90 and 7.95 (2s, 1H, H-8').

Example 85

CIS AND TRANS-2-(DIETHYLOXYPHOSPHINOYLMETHYL)-4-(GUANIN-9'-YLMETHYL)-1,3-DIOXOLANE

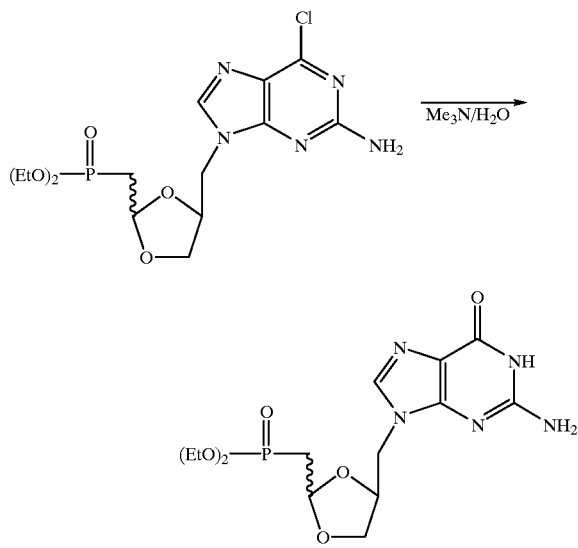

To a solution of cis and trans-4-(2$^1$-amino-6'-chloropurin-9'-ylmethyl)-2-(diethyloxyphosphinoylmethyl)-1,3-dioxolane (example 84) (300 mg, 0.739 mmol) in H$_2$O (25 mL) was added Me$_3$N (3.5 ml of a 25% solution, 14.8 mmol, 20 eq.). The mixture was stirred at room temperature for 64 hr then the solution was evaporated under reduced pressure. The crude material was purified by flash chromatography with a mixture of dichloromethane and methanol (80:20) to give the compound (258 mg) in 90% yield.

$^1$H NMR (300 MHz, DMSO) δ: 1.19 (t, 6H, J=7.1 Hz, CH$_3$), 2.18 (ddd, 2H, $^2$J$_{HP}$=18.5 Hz, J=5.3 Hz, 5.3 Hz, CH$_2$P), 3.65 (dd, 0.33H, J=5.9 Hz, 8.4 Hz, H-5a for trans), 3.95 (m, 4H, CH$_2$, and 1.66H, H-5b for trans and H-5 for cis), 4.08 (m, 2H, CH$_2$N), 4.40 and 4.46 (2m, 1H, H-4), 5.02 (dt, 0.66H, J=5.0 Hz, $^3$J$_{HP}$=5.0 Hz, H-2 for cis), 5.21 (dt, 0.33H, J=5.0 Hz, $^3$J$_{HP}$=50 Hz, H-2 for trans), 6.53 (bs, 2H, NH$_2$), 7.65 and 7.68 (2s, 1H, H-8'), 10.64 (bs, 1H, NH).

Example 86

CIS-2-(DIHYDROXYPHOSPHINOYLMETHYL)-4-(GUANIN-9'-YLMETHYL)-1,3-DIOXOLANE, MONOAMMONIUM SALT (BCH-1845)

TRANS-2-(DIHYDROXYPHOSPHINOYLMETHYL)-4-(GUANIN-9'-YLMETHYL)-1,3-DIOXOLANE, MONOAMMONIUM SALT (BCH-1846)

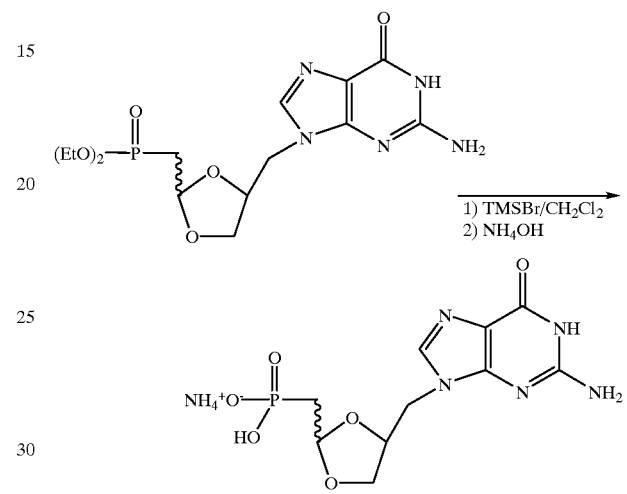

To a solution of cis and trans-2-(diethyloxyphosphinoylmethyl)-4-(guanin-9'-ylmethyl)-1,3-dioxolane (example 85) (266 mg, 0.687 mmol) in dichloromethane (10 mL) and DMF (0.3 mL), was added TMSBr (5 g, 33.1 mmol, 50 eq.). The mixture was stirred at room temperature for 48 hr then the solution was evaporated under reduced pressure. A solution of ammonium hydroxide was added and the solution was evaporated again. The crude material was purified by reverse phase HPLC to give 42.2 mg of the cis compound, 24 mg of trans and 20 mg of mixture for a total yield of 36%.

cis isomer

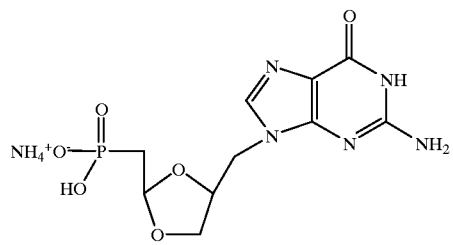

$^1$H NMR (300 MHz, D$_2$O) δ: 1.76 (ddd, 2H, $^2$J$_{HP}$=18.0 Hz, J=1.8 Hz, 5.3 Hz, CH$_2$P), 3.81 (d, 2H, J=5.5 Hz, H-5), 4.07 (dd, 1H, J=5.5 Hz, 14.8 Hz, CH$_A$H$_B$N), 4.14 (dd, 1H, J=3.4 Hz, 14.8 Hz, CH$_A$H$_B$N), 4.36 (m, 1H, H-4), 4.90 (dt, 1H, J=5.4 Hz, $^3$J$_{HP}$=9.6 Hz, H-2), 7.97 (s, 1H, H-8'). MP: 214° C. (dec); UV λ$_{max}$ (H$_2$O): 252.0, 270.9 nm.

trans isomer

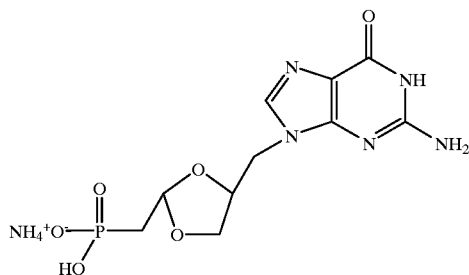

$^1$H NMR (300 MHz, D$_2$O) δ: 1.80 (dm, 2H, $^2J_{HP}$=18.0 Hz, CH$_2$P), 3.56 (dd, 1H, J=6.1 Hz, 9.0 Hz, H-5a), 4.07 (m, 3H, H-5b and CH$_2$N), 4.37 (m, 1H, H-4), 5.07 (dt, 1H, J=5.6 Hz, $^3J_{HP}$=9.7 Hz, H-2), 7.77 (s, 1H, H-8'). MP: 210° C. (dec); UV λ$_{max}$ (H$_2$O): 252.4, 270.2 nm.

Example 87

CIS-4-(2',6'-DIAMINOPURIN-9'-YLMETHYL)-2-(DIHYDROXYPHOSPHINOYLMETHYL)-1,3-DIOXOLANE, MONOAMMONIUM SALT

TRANS-4-(2',6'-DIAMINOPURIN-9'-YLMETHYL)-2-(DIHYDROXYPHOSPHINOYLMETHYL)-1,3-DIOXOLANE, MONOAMMONIUM SALT (BCH-2589)

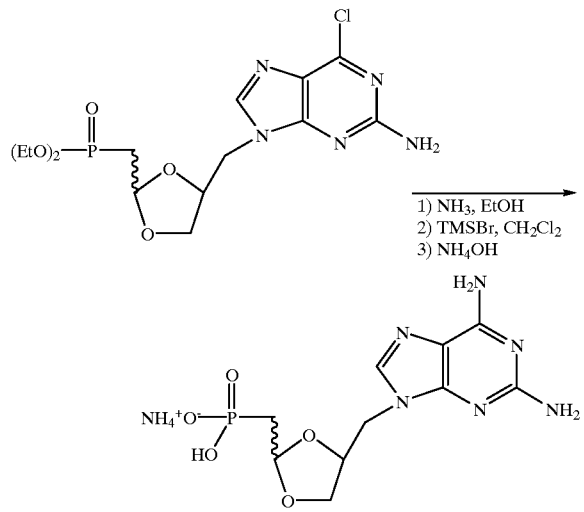

1) NH$_3$, EtOH
2) TMSBr, CH$_2$Cl$_2$
3) NH$_4$OH

To a solution of cis and trans-4-(2'-amino-6'-chloropurin-9'-ylmethyl)-2-(diethyloxyphosphinoylmethyl)-1,3-dioxolane (example 84) (289 mg, 0.712 mmol) in ethanol (15 mL), was saturated with ammonia at 0° C. The mixture was heated at 80° C., in a steel bomb for 18 hr, then the solution was evaporated under reduced pressure. To the crude material in dichloromethane (10 mL) and DMF (0.3 mL), was added TMSBr (2.8 mL, 21.4 mmol, 30 eq.). The mixture was stirred at room temperature for 18 hr then the solution was evaporated under reduced pressure. A solution of ammonium hydroxide was added and the solution was evaporated again. The crude material was purified by reverse phase HPLC to give 28.2 mg of the cis compound, 54.8 mg of trans and 44.3 mg of mixture for a total yield of 51%.

cis isomer

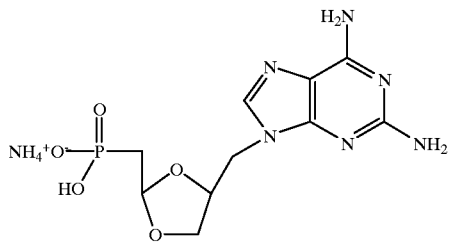

$^1$H NMR (300 MHz, D$_2$O) δ: 1.74 (ddd, 2H, $^2J_{HP}$=18.0 Hz, J=5.6 Hz, 6.3 Hz, CH$_2$P), 3.80 (m, 2H, H-5), 4.06 (dd, 1H, J=5.2 Hz, 15 Hz, CH$_A$H$_B$N), 4.13 (dd, 1H, J=3.6 Hz, 15 Hz, CH$_A$H$_B$N), 4.38 (m, 1H, H-4), 4.92 (dt, 1H, J=4.3 Hz, $^3J_{HP}$=5.3 Hz, H-2), 7.76 (s, 1H, H-8'). MP: 235° C. (dec); UV λ$_{max}$ (H$_2$O): 254.0, 279.1 nm.

trans isomer

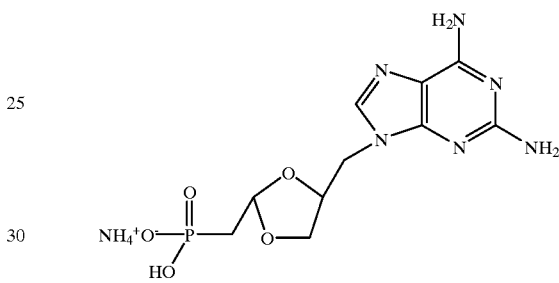

$^1$H NMR (300 MHz, D$_2$O) δ: 1.82 (ddd, 2H, $^2J_{HP}$=17.8 Hz, J=4.6 Hz, 6.0 Hz, CH$_2$P), 3.56 (dd, 1H, J=6.3 Hz, 9.1 Hz, H-5a), 4.10 (m, 3H, H-5b and CH$_2$N), 4.39 (m, 1H, H-4), 5.08 (dt, 1H, J=4.6 Hz, $^3J_{HP}$=5.2 Hz, H-2), 7.76 (s, 1H, H-8'). MP: 235° C. (dec); UV λ$_{max}$ (H$_2$O): 251.3, 285.3 nm.

Example 88

CIS AND TRANS-4-(ADENIN-9'-YLMETHYL)-2-(DIETHYLOXYPHOSPHINOYLMETHYL)-1,3-DIOXOLANE

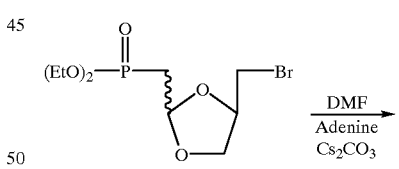

DMF
Adenine
Cs$_2$CO$_3$

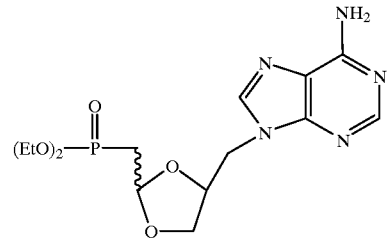

To a solution of cis and trans-4-(bromomethyl)-2-(diethyloxyphosphinoylmethyl)-1,3-dioxolane (example 83) (1.00 g, 3.15 mmol) and adenine (469 mg, 3.47 mmol, 1.1 eq.) in DMF (60 mL) was added Cs$_2$CO$_3$ (2.00 g, 6.30 mmol, 2 eq.). The mixture was stirred at 80° C. for 24 hr. After, the solution was cooled to room temperature, the solid was filtered and was washed with DMF. The solvent was evaporated under reduced pressure. The crude material was purified by flash chromatography with a mixture of dichloromethane and methanol (90:10) to give the compound (605 mg) in 52% yield.

$^1$H NMR (300 MHz, CDCl$_3$) δ: 1.32 (m, 6H, CH$_3$), 2.20 (dm, 2H, $^2J_{HP}$=18.5 Hz, CH$_2$P), 3.65 (dd, 0.33H, J=6.7 Hz, 8.9 Hz, H-5a for trans), 3.92 (dd, 0.66H, J=4.7 Hz, 8.8 Hz, H-5a for cis), 3.99 (dd, 0.66H, J=7.0 Hz, 8.8 Hz, H-5b for cis), 4.12 (m, 4H, CH$_2$), 4.22 to 4.5 (2m, 0.33H, H-5b for trans, and 2H, CH$_2$N), 4.53 (m, 1H, H-4), 5.18 (dt, 0.66H, J=5.1 Hz, $^3J_{HP}$=5.9 Hz, H-2 for cis), 5.30 (dt, 0.33H, J=5.1 Hz, $^3J_{HP}$=5.1 Hz, H-2 for trans), 5.70 (bs, 2H, NH$_2$), 7.97 (2s, 1H, H-2') and 8.36 (s, 1H, H-8').

Example 89

CIS-4-(ADENIN-9'-YLMETHYL)-2-(DIHYDROXYPHOSPHINOYLMETHYL)-1,3-DIOXOLANE, MONOAMMONIUM SALT

TRANS-4-(ADENIN-9'-YLMETHYL)-2-(DIHYDROXYPHOSPHINOYLMETHYL)-1,3-DIOXOLANE, MONOAMMONIUM SALT

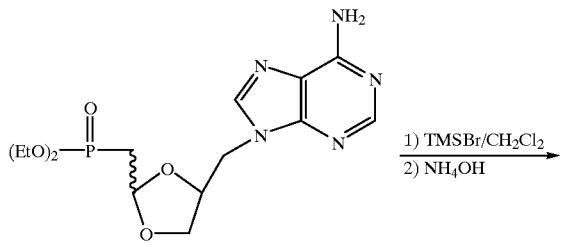

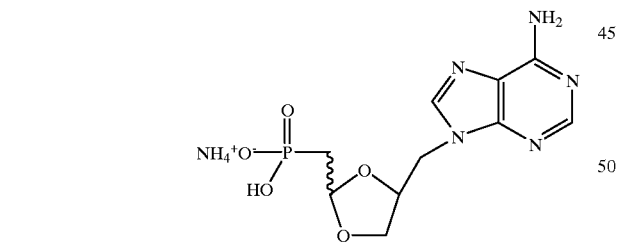

To a solution of cis and trans-4-(adenin-9'-ylmethyl)-2-(diethyloxyphosphinoylmethyl)-1,3-dioxolane (example 88) (315 mg, 0.848 mmol) in dichloromethane (10 mL) was added TMSBr (3 mL, 22.7 mmol, 27 eq.). The mixture was stirred at room temperature for 20 hr then the solution was evaporated under reduced pressure. A solution of ammonium hydroxide was added and the solution was evaporated again. The crude material was purified by reverse phase HPLC to give 45.2 mg of the cis compound, 21.1 mg of trans and 28.9 mg of mixture for a total yield of 34%.

cis isomer

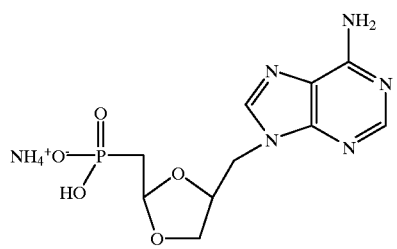

$^1$H NMR (300 MHz, D$_2$O) δ: 1.69 (ddd, 2H, $^2J_{HP}$=17.5 Hz, J=5.5 Hz, 7.4 Hz, CH$_2$P), 3.77 (dd, 1H, J=4.0 Hz, 9.1 Hz, H-5a), 3.83 (dd, 1H, J=6.9 Hz, 9.3 Hz, H-5b), 4.23 (dd, 1H, J=5.2 Hz, 14.8 Hz, CH$_A$H$_B$N), 4.29 (dd, 1H, J=3.3 Hz, 15.1 Hz, CH$_A$H$_B$N), 4.43 (m, 1H, H-4), 4.90 (dt, 1H, J=5.2 Hz, $^3J_{HP}$=9.4 Hz, H-2), 8.07 (s, 2H, H-2' and H-8'). MP: 206° C. (dec); UV λ$_{max}$ (H$_2$O): 259.3 nm.

trans isomer

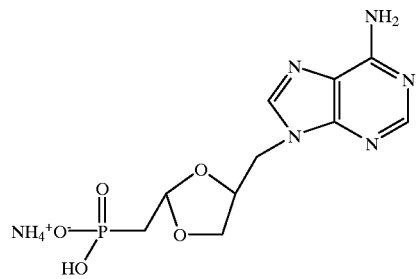

$^1$H NMR (300 MHz, D$_2$O) δ: 1.81 (dm, 2H, $^2J_{HP}$=18.0 Hz, CH$_2$P), 3.57 (dd, 1H, J=6.5 Hz, 9.0 Hz, H-5a), 4.11 (dd, 1H, J=6.8 Hz, 9.0 Hz, H-5b), 4.27 (s, 2H, CH$_2$N), 4.43 (m, 1H, H-4), 5.07 (dt, 1H, J=4.2 Hz, $^3J_{HP}$=4.9 Hz, H-2), 8.07 (s, 2H, H-2' and H-8'). MP: 200° C. (dec). UV λ$_{max}$ (H$_2$O): 259.8 nm.

Example 90

(2R)-3-BROMO-1,2-PROPANEDIOL

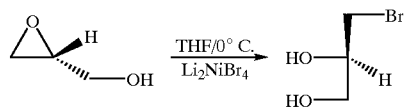

Anhydrous lithium bromide (39.74 g, 0.458 mol, 2 eq) and nickel bromide (50.0 g, 0.229 mol), were stirred in dry THF (575 mL) at room temperature. After 48 hrs, the stirring was stopped and any undissolved material allowed to settle, to reveal a clear dark blue-green solution of Li$_2$NiBr$_4$ (~0.4M).

To a solution of (R)(+) glycidol (5.0 g, 67.5 mmol) in THF (100 mL) was added Li$_2$NiBr$_4$ (260 mL, 104 mmol, 1.5 eq) at 0° C. The mixture was stirred at 0° C. for 45 min then the solvent was evaporated. The residue was filtrated over silica gel with ethyl acetate to remove most of the inorganic salts. After evaporation of the solvent, the residue was purified by flash chromatography with a mixture of dichloromethane and ethyl acetate (50:50 to 0:100) to give the product (6.75 g) in 65% yield.

$^1$H NMR (300 MHz, DMSO) δ: 3.38 and 3.57 (2m, 5H, H-3, H-1, H-2), 4.72 (t, 1H, J=5.6 Hz, CH$_2$OH), 5.14 (d, 1H, J=5.1 Hz, CH—OH).

$[α]_D$ −5.1° (c=1.07, MeOH)

Example 91

(2S)-3-BROMO-1,2-PROPANEDIOL

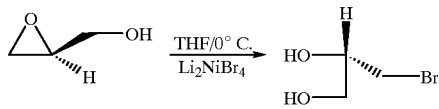

Prepared from (S)(−) glycidol as in example 90.

$[α]_D$+4.9° (c=1.05, MeOH)

Example 92

(2R,4R) AND (2S,4R)-4-(BROMOMETHYL)-2-(DIETHYLOXYPHOSPHINOYLMETHYL)-1,3-DIOXOLANE

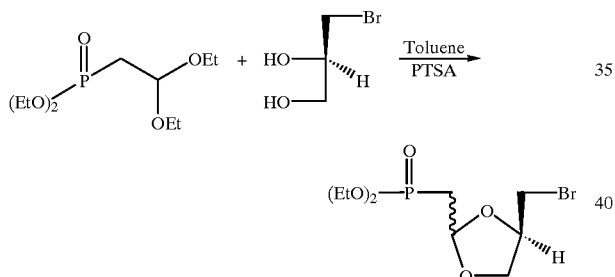

To a solution of diethylphosphonoacetaldehyde diethylacetal (4.20 g, 16.5 mmol) and (2R)-3-bromo-1,2-propanediol (example 90) (3.00 g, 19.4 mmol, 1.2 eq.) in toluene (30 mL) was added pTSA (few crystals). The mixture was stirred at reflux for 50 hr. After, the solution was cooled to room temperature, and a saturated solution of sodium bicarbonate was added, and the aqueous phase was extracted with dichloromethane. The organic layer was dried over anhydrous sodium sulphate and evaporated under reduced pressure. The crude material was pure by TLC and NMR, and gave 5.06 g of the compound in a 97% yield. $^1$H NMR (300 MHz, CDCl$_3$) δ: 1.33 (t, 6H, J=7.0 Hz, CH$_3$), 2.20 (dd, 0.66H, J=5.4 Hz, $^2J_{HP}$=18 Hz, CH$_2$P for trans), 2.25 (dd, 1.33H, J=5.2 Hz, $^2J_{HP}$=18.7 Hz, CH$_2$P for cis), 3.32 (2dd, 1H, J=7.9 Hz, 10.2 Hz, C$\underline{H}_A$H$_B$Br), 3.42 and 3.48 (2dd, 1H, J=4.8 Hz, 10.2 Hz, CH$_A\underline{H}_B$Br), 3.74 (dd, 0.33H, J=6.4 Hz, 8.8 Hz, H-5a for trans), 3.99 (d, 1.33H, J=5.2 Hz, H-5 for cis), 4.13 (m, 4H, CH$_2$), 4.26 (dd, 0.33H, J=6.4 Hz, 8.8 Hz, H-5b for trans), 4.35 (m, 1H, H-4), 5.24 (dt, 0.66H, J=5.2 Hz, $^3J_{HP}$=4.7 Hz, H-2 for cis), 5.37 (dt, 0.33H, J=5.2 Hz, $^3J_{HP}$=5.2 Hz, H-2 for trans).

Example 93

(2R,4S) AND (2S,4S)-4-(BROMOMETHYL)-2-(DIETHYLOXYPHOSPHINOYLMETHYL)-1,3-DIOXOLANE

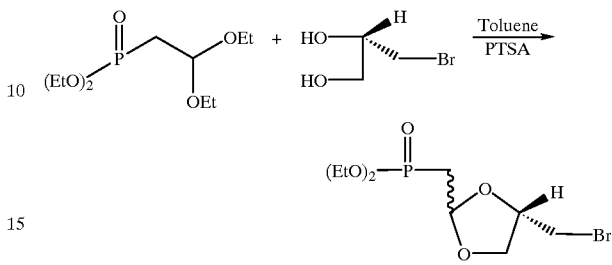

Prepared from (2S)-3-bromo-1,2-propanediol (example 91) as in example 92.

Example 94

(2R,4S) AND (2S,4S)-4-(2'-AMINO-6'-CHLOROPURIN-9'-YLMETHYL)-2-(DIETHYLOXYPHOSPHINOYLMETHYL)-1,3-DIOXOLANE

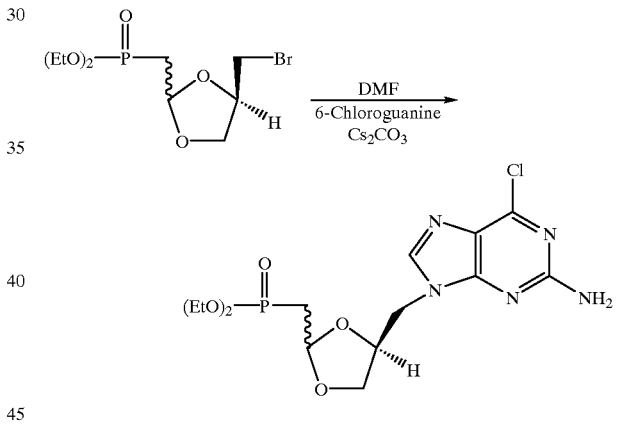

To a solution of (2R,4R) and (2S,4R)-4-(bromomethyl)-2-(diethyloxyphosphinoylmethyl)-1,3-dioxolane (example 92) (4.90 g, 15.45 mmol) and 6-chloroguanine (2.90 g, 17.0 mmol, 1.1 eq.) in DMF (300 mL) was added Cs$_2$CO$_3$ (10.0 g, 30.9 mmol, 2 eq.). The mixture was stirred at 80° C. for 22 hr. After, the solution was cooled to room temperature and the solid was filtered and was washed with DMF. The solvent was evaporated under reduced pressure. The crude material was purified by flash chromatography with a mixture of ethyl acetate and methanol (95:5 to 90:10) to give the pure compound (3.14 g) in 50% yield.

$^1$H NMR (300 MHz, CDCl$_3$) δ: 1.32 (m, 6H, CH$_3$), 2.20 (dm, 2H, $^2J_{HP}$=18.6 Hz, CH$_2$P), 3.65 (dd, 0.33H, J=6.6 Hz, 8.8 Hz, H-5a for trans), 3.91 (dd, 0.66H, J=4.5 Hz, 8.7 Hz, H-5a for cis), 3.98 (dd, 0.66H, J=7.0 Hz, 8.9 Hz, H-5b for cis), 4.12 (m, 4H, CH$_2$, and 0.33H, H-5b for trans), 4.27 (m, 2H, CH$_2$N), 4.50 (m, 1H, H-4), 5.12 and 5.16 (2bs, 2H, NH$_2$), 5.17 (dt, 0.66H, J=5.1 Hz, $^3J_{HP}$=6.1 Hz, H-2 for cis), 5.34 (dt, 0.33H, J=5.2 Hz, $^3J_{HP}$=5.1 Hz, H-2 for trans), 7.90 and 7.95 (2s, 1H, H-8').

Example 95

(2R,4R) AND (2S,4R)-4-(2'-AMINO-6'-CHLOROPURIN-9'-YLMETHYL)-2-(DIETHYLOXYPHOSPHINOYLMETHYL)-1,3-DIOXOLANE

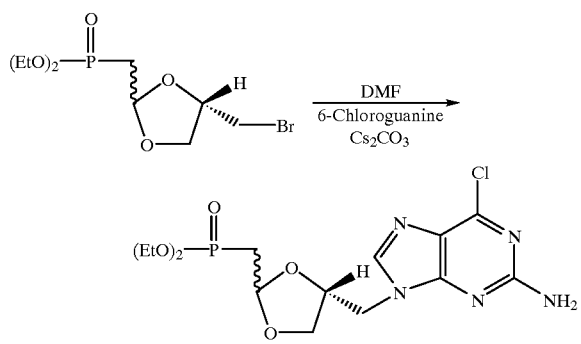

Prepared from (2R,4S) and (2S,4S)-4-(bromomethyl)-2-(diethyloxyphosphinoylmethyl)-1,3-dioxolane (example 93) as in example 94.

Example 96

(2R,4S) AND (2S,4S)-2-(DIETHYLOXYPHOSPHINOYLMETHYL)-4-(GUANIN-9'-YLMETHYL)-1,3-DIOXOLANE

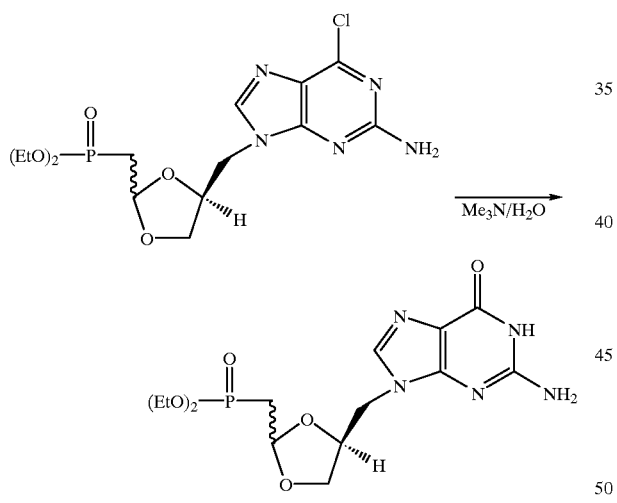

To a solution of (2R,4S) and (2S,4S)-4-(2'-amino-6'-chloropurin-9'-ylmethyl)-2-(diethyloxyphosphinoylmethyl)-1,3-dioxolane (example 94) (3.06 g, 7.54 mmol) in H$_2$O (250 mL) was added Me$_3$N (35.5 ml of a 25% solution, 15.0 mmol, 20 eq.). The mixture was stirred at room temperature for 68 hr then the solution was evaporated under reduced pressure. The crude material was purified by flash chromatography with a mixture of dichloromethane and methanol (85:15 to 75:25) to give the pure compound (2.61 g) in 89% yield.

$^1$H NMR (300 MHz, DMSO) δ: 1.19 (t, 6H, J=7.1 Hz, CH$_3$) 2.18 (ddd, 2H, $^2$J$_{HP}$=18.5 Hz, J=5.3 Hz, 5.3 Hz, CH$_2$P), 3.65 (dd, 0.33H, J=5.8 Hz, 8.6 Hz, H-5a for trans), 3.95 (m, 4H, CH$_2$, and 1.66H, H-5b for trans and H-5 for cis), 4.08 (m, 2H, CH$_2$N), 4.39 and 4.46 (2m, 1H, H-4), 5.02 (dt, 0.66H, J=5.0 Hz, $^3$J$_{HP}$=5.0 Hz, H-2 for cis), 5.21 (dt, 0.33H, J=5.0 Hz, $^3$J$_{HP}$=5.0 Hz, H-2 for trans), 6.57 (bs, 2H, NH$_2$), 7.65 and 7.68 (2s, 1H, H-8'), 10.67 (bs, 1H, NH). UV λ$_{max}$ (H$_2$O): 251.3, 270.9 nm.

Example 97

(2S,4R) AND (2R,4R)-2-(DIETHYLOXYPHOSPHINOYLMETHYL)-4-(GUANIN-9'-YLMETHYL)-1,3-DIOXOLANE

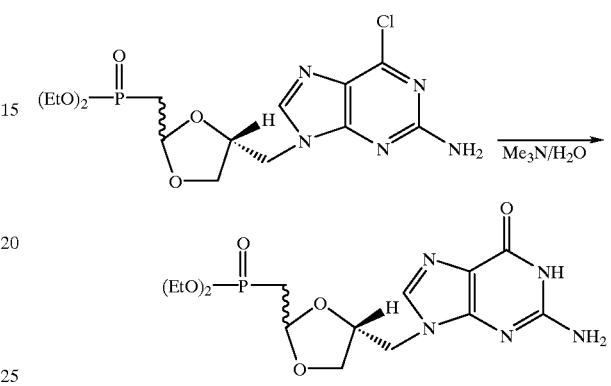

Prepared from (2S,4R) and (2R,4R)-4-(2'-amino-6'-chloropurin-9'-ylmethyl)-2-(diethyloxyphosphinoylmethyl)-1,3-dioxolane (example 95) as in example 96.

Example 98

(2R,4S)-2-(DIHYDROXYPHOSPHINOYLMETHYL)-4-(GUANIN-9'-YLMETHYL)-1,3-DIOXOLANE, MONOAMMONIUM SALT

(2S,4S)-2-(DIHYDROXYPHOSPHINOYLMETHYL)-4-(GUANIN-9'-YLMETHYL)-1,3-DIOXOLANE, MONOAMMONIUM SALT

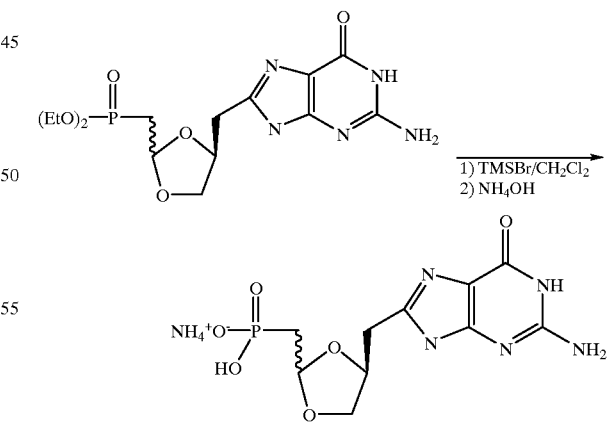

To a solution of (2R,4S) and (2S,4S)-2-(diethyloxyphosphinoylmethyl)-4-(guanin-9'-ylmethyl)-1,3-dioxolane (example 96) (503 mg, 1.30 mmol) in dichloromethane (15 mL) and DMF (1.5 mL), was added TMSBr (3.4 mL, 26.0 mmol, 20 eq.). The mixture was stirred at room temperature for 48 hr then the solution was evaporated cis isomer under reduced pressure. A solution of ammonium hydroxide was added and the solution was evaporated again to give 670 mg of product. The crude material (400 mg) was purified by HPLC to give 71.6 mg of the cis compound, 60.0 mg of trans and 12.2 mg of mixture for a total yield of 53%.

cis isomer

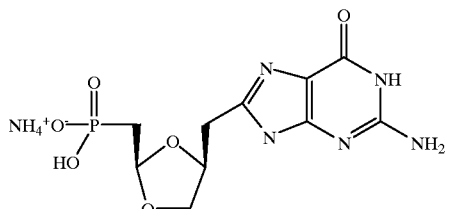

$^1$H NMR (300 MHz, D$_2$O) δ 1.73 (ddd, 2H, $^2J_{HP}$=17.3 Hz, J=5.3 Hz, 5.3 Hz, CH$_2$P), 3.81 (m, 2H, H-5), 4.07 (dd, 1H, J=5.5 Hz, 14.9 Hz, CH$_A$H$_B$N), 4.10 (dd, 1H, J=3.5 Hz, 14.8 Hz, CH$_A$H$_B$N), 4.36 (m, 1H, H-4), 4.92 (dt, 1H, J=5.4 Hz, $^3J_{HP}$=4.1 Hz, H-2), 7.73 (s, 1H, H-8').

$^{13}$C NMR (D$_2$O) δ: 34.9 (CH$_2$P, $^1J_{CP}$=128 Hz), 46.9 (CH$_2$N), 68.1 (CH$_2$O), 74.8 (CHO), 103.7 (OCHO), 110.1 (C5), 116.9 (C4), 142.1 (C8), 154.9 (C2), 160.2 (C6). UV λ$_{max}$ (H$_2$O): 251.6, 270.9 nm. MP: 210° C. (dec);

[α]$_D$ +15.7° (c=0.26, H$_2$O)

trans isomer

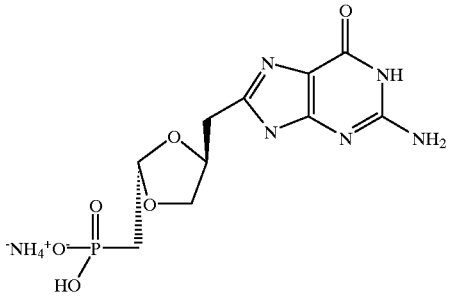

$^1$H NMR (300 MHz, D$_2$O) δ: 1.82 (ddd, 2H, $^2J_{HP}$=17.6 Hz, J=5.0 Hz, 6.2 Hz, CH$_2$P), 3.58 (dd, 1H, J=6.1 Hz, 9.0 Hz, H-5a), 4.09 (m, 3H, H-5b and CH$_2$N), 4.39 (m, 1H, H-4), 5.11 (dt, 1H, J=4.7 Hz, $^3J_{HP}$=5.6 Hz, H-2), 7.73 (s, 1H, H-8'). UV λ$_{max}$ (H$_2$O): 251.3, 270.9. MP: 210° C. (dec)

[α]$_D$ -29.2° (c=0.24, H$_2$O)

Example 99

(2S,4R)-2-(DIHYDROXYPHOSPHINOYLMETHYL)-4-(GUANIN-9'-YLMETHYL)-1,3-DIOXOLANE, MONOAMMONIUM SALT (2R,4R)-2-(DIHYDROXYPHOSPHINOYLMETHYL)-4-(GUANIN-9'-YLMETHY-1,3-DIOXOLANE, MONOAMMONIUM SALT

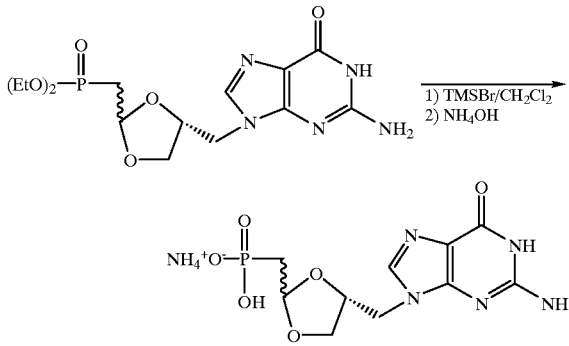

To a solution of (2S,4R) and (2R,4R)-2-(diethyloxyphosphinoylmethyl)-4-(guanin-9'-ylmethyl)-1,3-dioxolane (example 97) (502 mg, 1.30 mmol) in dichloromethane (15 mL) and DMF (1.5 mL), was added TMSBr (3.4 mL, 26.0 mmol, 20 eq.). The mixture was stirred at room temperature for 3.5 days then the solution was evaporated under reduced pressure. A solution of ammonium hydroxide was added and the solution was evaporated again to give 760 mg of the product. The crude material (300 mg) was purified by HPLC to give 41.0 mg of the cis compound, 33.0 mg of trans and 10.4 mg of mixture for a total yield of 47%.

cis isomer

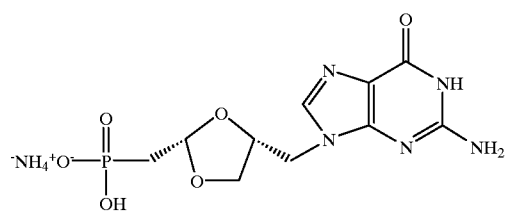

$^1$H NMR (300 MHz, D$_2$O) δ: 1.76 (ddd, 2H, $^2J_H$P17.6 Hz, J=5.2 Hz, 5.2 Hz, CH$_2$P), 3.83 (d, 2H, J=5.5 Hz, H-5), 4.07 (dd, 1H, J=5.4 Hz, 14.8 Hz, CH$_A$H$_B$N), 4.12 (dd, 1H, J=3.6 Hz, 14.8 Hz, CH$_A$H$_B$N), 4.38 (m, 1H, H-4), 4.94 (dt, 1H, J=5.4 Hz, $^3J_{HP}$=4.1 Hz, H-2), 7.74 (s, 1H, H-8'). UV λ$_{max}$ (H2O): 251.1, 271.1 nm. MP: 210° C. (dec);

[α]$_D$ -14.6° (c=0.24, H$_2$O)

trans isomer

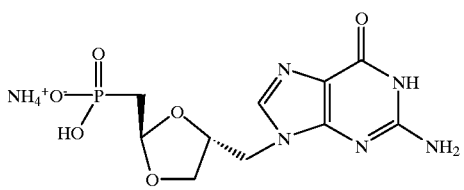

$^1$H NMR (300 MHz, D$_2$O) δ: 1.86 (ddd, 2H, $^2$J$_{HP}$=17.7 Hz, J=5.0 Hz, 5.0 Hz, CH$_2$P), 3.60 (dd, 1H, J=6.1 Hz, 9.0 Hz, H-5a), 4.11 (m, 3H, H-5b and CH$_2$N), 4.41 (m, 1H, H-4), 5.12 (dt, 1H, J=4.6 Hz, $^3$J$_{HP}$=5.8 Hz, H-2), 7.74 (s, 1H, H-8'). UV λ$_{max}$ (H$_2$O): 251.6, 271.3 nm. MP: 210° C. (dec); [α]$_D$ +31.7° (c=0.255, H$_2$O)

Example 100

(5S)-5-(BROMOMETHYL)-2-HYDROXY-TETRAHYDROFURAN

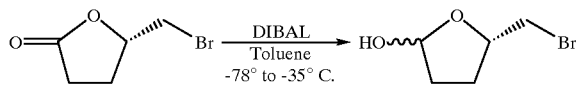

To a stirring solution of (–)-(5S)-5-(bromomethyl) tetrahydrofuran-2-one (Mattes, H.; Benezra, C. *J. Org. Chem.* 1988, 53, 2732.) (1.642 g, 9.17 mmol) in dry toluene (55 mL) was added dropwise at –78° C. a 1.5 M solution of DIBAL in toluene (7.34 mL, 11.01 mmol). The mixture was stirred at –78° C. for 3 hours and then allowed to warm up until –35° C. (2 hours). Water (20 mL) was added at –35° C., the mixture was allowed to warm up at room temperature and filtered through CELITE diatomaceous earth. The filtrate was washed with water (30 mL), saturated aqueous solution of NaHCO$_3$ (20 mL) and brine (15 mL). It was dried over anhydrous MgSO$_4$, filtered and concentrated under reduced pressure. The residue was purified by flash chromatography using 40% ethyl acetate in hexane to give the title compound as an oil (1.273 g, 77%). R$_f$ 0.33 (40% EtOAc/Hex).

$^1$H NMR (300 MHz, CDCl$_3$) δ: 5.63 (m, 0.5 H, H-2), 5.55 (m, 0.5 H, H-2), 4.48 (qt, 0.5 H, J=6 Hz, H-5), 4.30 (qt, 0.5 H, J=6 Hz, H-5), 3.54 (dd, 0.5 H, J=6 HZ and 10 Hz, H-6), 3.45 (dd, 0.5 H, J=6 HZ and 10 Hz, H-6), 3.39 (d, 1 H, J=5 Hz, H-6), 3.00 (s, 1 H, OH), 2.30–1.70 (m, 4 H, H-3, H-4) ppm.

Example 101

(5R)-5-(BROMOMETHYL)-2-HYDROXY-TETRAHYDROFURAN

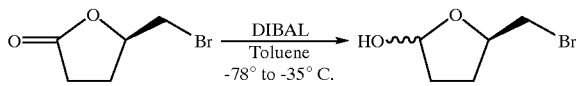

Prepared from (+)-(5R)-5-(bromomethyl) tetrahydrofuran-2-one as in example 100.

Example 102

(5S)-2-O-ACETYL-5-(BROMOMETHYL)-TETRAHYDROFURAN

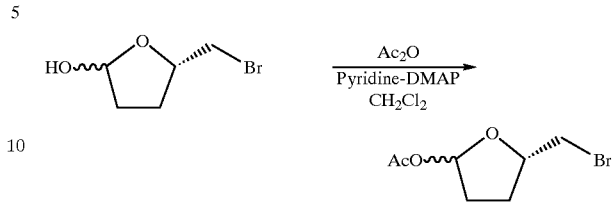

To a stirring solution of (–)-(5S)-5-(bromomethyl)-2-hydroxy-tetrahydrofuran (example 100) (1.273 g, 7.03 mmol), pyridine (1.25 mL, 15.47 mmol) and DMAP (catalytic) in dry methylene chloride (35 mL) was added at room temperature acetic anhydride (1.33 mL, 14.06 mmol). The mixture was stirred at room temperature for 4 hours and then washed with water (30 mL), aqueous HCl (10%, 20 mL) and saturated aqueous solution of NaHCO$_3$ (20 mL). It was dried over anhydrous MgSO4, filtered and concentrated under reduced pressure. The residue was purified by flash chromatography using 15% ethyl acetate in hexane to give the title compound as an oil (1.330 g, 85%). R$_f$ 0.40 (20% EtOAc/Hex).

$^1$H NMR (300 MHz, CDCl$_3$) δ: 6.36 (m, 0.5 H. H-2), 6.31 (m, 0.5 H, H-2), 4.50 (m, 0.5 H, H-5), 4.37 (m, 0.5 H, H-5), 3.55 (dd, 0.5 H, J=5 HZ and 10 Hz, H-6), 3.45 (dd, 0.5 H, J=6 HZ and 10 Hz, H-6), 3.37 (dd, 0.5 H, J=5 HZ and 10 Hz, H-6), 3.35 (dd, 0.5 H, J=6 HZ and 10 Hz, H-6), 2.30–1.70 (m, 4 H, H-3, H-4), 2.05 (s, 3 H, CH$_3$) ppm.

Example 103

(5R)-2-O-ACETYL-5-(BROMOMETHYL)-TETRAHYDROFURAN

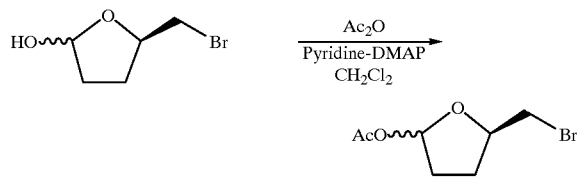

Prepared from (5R)-5-(bromomethyl)-2-hydroxy-tetrahydrofuran (example 101) as in example 102.

Example 104

(–)-(2S,5S)-5-(BROMOMETHYL)-2-DIETHOXYPHOSPHINOYL-TETRAHYDROFURAN (–)-(2R,5S)-5-(BROMOMETHYL)-2-DIETHOXYPHOSPHINOYL-TETRAHYDROFURAN

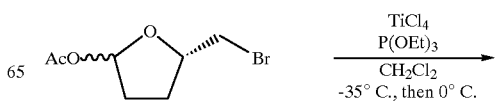

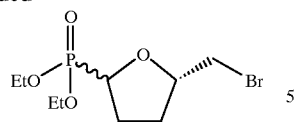

To a stirring solution of (5S)-2-O-acetyl-5-(bromomethyl)-tetrahydrofuran (example 102) (1.330 g, 5.96 mmol) and triethylphosphite (1.33 mL, 7.75 mmol) in dry methylene chloride (50 mL) was added dropwise at −35° C. titanium tetrachloride (0.655 mL, 5.96 mmol) over a period of 10 minutes. The yellow solution was stirred at −35° C. for 30 minutes and then 0° C. for another 30 minutes. Saturated aqueous solution of NaHCO$_3$ (40 mL) was added to the reaction mixture and the suspension was filtered through a CELITE diatomaceous earth. The mixture was partitioned followed by extraction of the aqueous phase with methylene chloride (2×30 mL). The combined extracts were washed with brine (60 mL), dried over anhydrous MgSO$_4$, filtered and concentrated under reduced pressure. The residue was purified by flash chromatography eluting with 10 to 20% acetone in hexane to give the cis isomer (821 mg) and the trans isomer (724 mg), both as an oil (total yield: 86%).

(−)-(2S,5S)-5-(bromomethyl)-2-diethoxyphosphinoyl-tetrahydrofuran

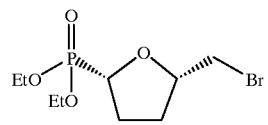

R$_f$ 0.57 (50% EtOAc/Hex).

[α]$_D$ −21° (c 3.32, CHCl$_3$).

$^1$H NMR (300 MHz, CDCl$_3$) δ: 4.35–4.10 (m, 6 H, H-5, H-2, CH$_2$CH$_3$), 3.49 (dd, 1 H, J=5 HZ and 10 Hz, H-6), 3.36 (dd, 1 H, J=7 HZ and 10 Hz, H-6), 2.30–1.95 (m, 4 H, H-3, H-4), 1.35 (t, 3 H. J=7 Hz, CH$_3$), 1.33 (t, 3 H, J=7 Hz, CH$_3$) ppm.

(−)-(2R,5S)-5-(bromomethyl)-2-diethoxyphosphinoyl-tetrahydrofuran

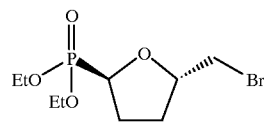

R$_f$ 0.51 (50% EtOAc/Hex).

[α]$_D$ −13° (c 4.66, CHCl$_3$).

$^1$H NMR (300 MHz, CDCl$_3$) δ: 4.40–4.10 (m, 6 H, H-5, H-2, CH$_2$CH$_3$), 3.47 (dd, 1 H, J=4 HZ and 10 Hz, H-6), 3.39 (dd, 1 H, J=6 HZ and 10 Hz, H-6), 2.25 (m, 3 H, CH$_2$CH$_2$), 1.85 (m, 1 H, CH$_2$CH$_2$), 1.35 (t, 3 H, J=7 Hz, CH$_3$), 1.34 (t, 3 H, J=7 Hz, CH$_3$) ppm.

Example 105

(+)-(2S,5R)-5-(BROMOMETHYL)-2-DIETHOXYPHOSPHINOYL-TETRAHYDROFURAN (+)-(2R,5R)-5-(BROMOMETHYL)-2-DIETHOXYPHOSPHINOYL-TETRAHYDROFURAN

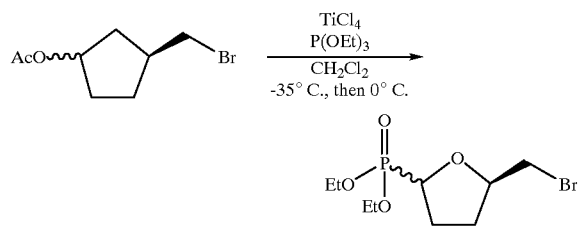

Prepared from (5R)-2-O-acetyl-5-(bromomethyl)-tetrahydrofuran (example 103) as in example 104.

(+)-(2R,5R)-5-(bromomethyl)-2-diethoxyphosphinoyl-tetrahydrofuran

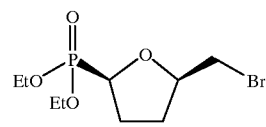

[α]$_D$ +24° (c 4.71, CHCl$_3$)

(+)-(2S,5R)-5-(bromomethyl)-2-diethoxyphosphinoyl-tetrahydrofuran

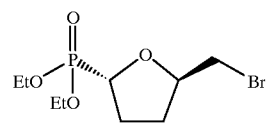

[α]$_D$ +13° (c 4.71, CHCl$_3$)

Example 106

(+)-(2S,5S)-5-(2'-AMINO-6'-CHLOROPURIN-9'-YlMETHYL)-2-DIETHOXYPHOSPHINOYL-TETRAHYDROFURAN

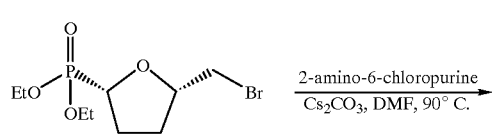

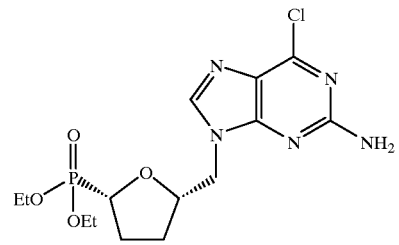

A solution of (−)-(2S,5S)-5-bromomethyl-2-diethoxyphosphinoyl-tetrahydrofuran (example 104) (704 mg, 2.34 mmol), 2-amino-6-chloropurine (476 mg, 2.81 mmol) and cesium carbonate (1.143 g, 2.50 mmol) in dry DMF (6 mL) was stirred at 90° C. for 6 hours. The mixture was then cooled and filtered. Concentration of the filtrate gave a residue which was purified by chromatography eluting with 2 to 5% methanol in methylene chloride. The desired product was obtained as a foam (406 mg, 45%).

$R_f$ 0.21 (5% MeOH/CH$_2$Cl$_2$). [α]$_D$ +78° (c 1.78, CHCl$_3$).

$^1$H NMR (300 MHz, CDCl$_3$) δ: 8.04 (s, 1 H, H-8'), 5.26 (s, 2 H, NH$_2$), 4.38 (m, 1 H, H-5), 4.20 (dd, 1 H, J=3 HZ and 14 Hz, H-2), 4.15–4.09 (m, 6 H, H-6, CH$_2$CH$_3$), 2.30–2.00 (m, 3 H, CH$_2$CH$_2$), 1.85 (m, 1 H, CH$_2$CH$_2$), 1.30 (t, 3 H, J=7 Hz, CH$_3$), 1.27 (t, 3 H, J=7 Hz, CH$_3$) ppm.

Example 107

(−)-(2R,5R)-5-(2'-AMINO-6'-CHLOROPURIN-9'-YlMETHYL)-2-DIETHOXYPHOSPHINOYL-TETRAHYDROFURAN

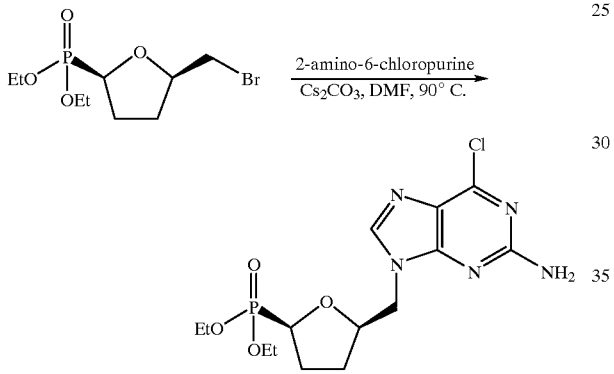

Prepared from (+)-(2R,5R)-5-bromomethyl-2-diethoxyphosphinoyl-tetrahydrofuran (example 105) as in example 106.

[α]$_D$ −75° (c 1.83, CHCl$_3$).

Example 108

(+)-(2S,5S)-2-DIHYDROXYPHOSPHINOYL-5-(GUANIN-9'-YlMETHYL)-TETRAHYDROFURAN, MONOAMMONIUM SALT (BCH-1850)

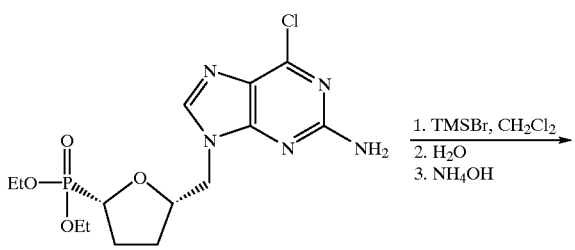

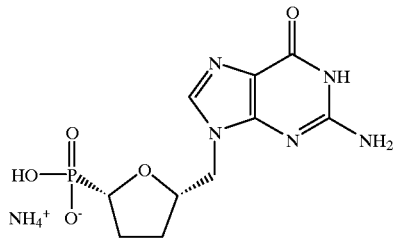

To a stirring solution of (+)-(2S,5S)-5-(2'-amino-6'-chloropurin-9'-ylmethyl)-2-diethoxyphosphinoyl-tetrahydrofuran (example 106) (150 mg, 0.39 mmol) in dry methylene chloride (4 mL) was added TMSBr (0.51 mL, 3.9 mmol). After stirring overnight at rt, the reaction mixture was concentrated to dryness and methanol (3×2 mL) was evaporated from the residue. The crude mixture was diluted in water (6 mL) and refluxed for 6 hours. The solution was made basic with ammonium hydroxide. Lyophilization followed by purification on C$_{18}$ reverse phase HPLC eluting with 0 to 15% acetonitrile in 0.01 M ammonium acetate gave the desired compound as a white solid (64 mg, 50%).

Mp >225° C. $R_f$ 0.17 (7:2:1 i-PrOH/H$_2$O/NH$_4$OH [α]$_D$ +56° (c 0.45, H$_2$O).

$^1$H NMR (300 MHz, D$_2$O) δ: 7.77 (s, 1 H, H-8'), 4.18 (m, 1 H, H-5), 3.95 (m, 2 H, H-6), 3.84 (t, 1 H, H-2, J=8.2 Hz), 1.94 (m, 3 H), 1.71 (m, 1 H) ppm.

$^{13}$C NMR (75.5 MHz, D$_2$O) d: 159.4, 154.2, 151.8, 141.4, 116.2, 79.6 (d, J=8 Hz), 76.9 (d, 162 Hz), 48.2, 29.2 (d, 7 Hz), 27.5 ppm. UV λ$_{max}$ 251 nm, 269 nm (H$_2$O).

Example 109

(−)-(2R,5R)-2-DIHYDROXYPHOSPHINOYL-5-(GUANIN-9'-YlMETHYL)-TETRAHYDROFURAN, MONOAMMONIUM SALT

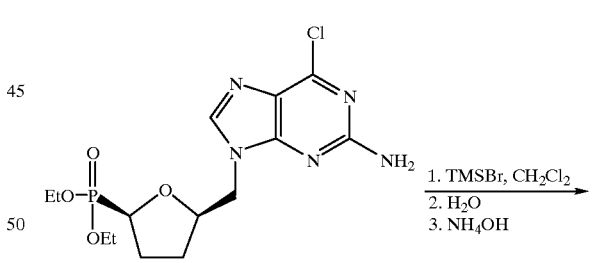

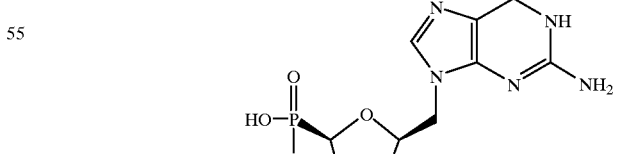

Prepared from (−)-(2R,5R)-5-(2'-amino-6'-chloropurin-9'-ylmethyl)-2-diethoxyphosphinoyl-tetrahydrofuran (example 107) as in example 108.

[α]$_D$ −56° (c 0.40, H$_2$O).

Example 110

(+)-(2S,5S)-5-(2',6'-DIAMINOPURIN-9'-YlMETRYL)-2-DIHYDROXYPHOSPHINOYL-TETRAHYDROFURAN, MONOAMMONIUM SALT

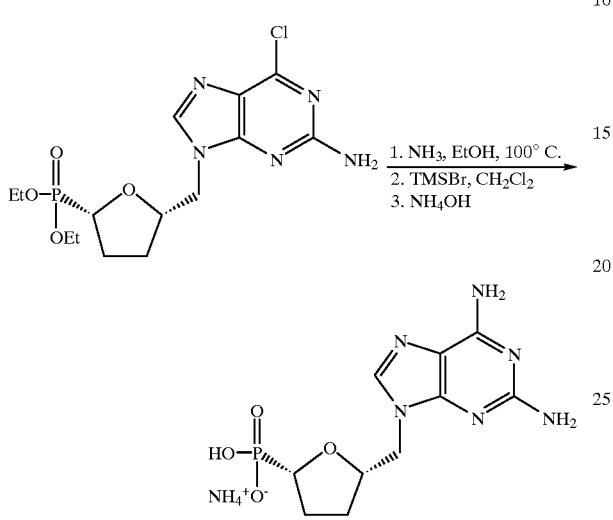

An ice-cold solution of (+)-(2S,5S)-5-(2'-amino-6'-chloropurin-9'-ylmethyl)-2-diethoxyphosphinoyl-tetrahydrofuran (example 106) (68 mg, 0.17 mmol) in ethanol (10 mL) was saturated with ammonia. The solution was then heated at 100° C. in a steel bomb for 16 hours. The bomb was cooled in ice and vented. Concentration of the solution gave a residue which was dissolved in dry methylene chloride (1 mL) and treated with TMSBr (0.23 mL, 1.74 mmol). After stirring for 16 h at room temperature, the mixture was concentrated to dryness and the residue was dissolved in water (3 mL). The solution was made basic with ammonium hydroxide and it was then washed with dichloromethane (2×5 mL) and hexane (5 mL). Lyophilization followed by purification on C$_{18}$ reverse phase HPLC eluting with 0 to 35% acetonitrile in 0.01 M ammonium acetate gave the desired compound as a white solid (47 mg, 82%).

Mp >225° C. R$_f$ 0.22 (7:2:1 i-PrOH/H$_2$O/NH$_4$OH).

[α]$_D$ +42° (c 0.48, H$_2$O).

$^1$H NMR (300 MHz, D$_2$O) δ: 7.73 (s, 1 H, H-8'), 4.20 (m, 1 H, H-5), 3.96 (dd, 1 H, J=3 HZ and 14 Hz, H-2), 3.90–3.80 (m, 3 H, H-6 and H-2), 2.10–1.80 (m, 3 H), 1.73 (m, 1 H) ppm. UV λ$_{max}$ 249 and 280 nm (H$_2$O).

Example 111

(−)-(2R,5R)-5-(2',6'-DIAMINOPURIN-9'-YlMETHYL)-2-DIHYDROXYPHOSPHINOYL-TETRAHYDROFURAN, MONOAMMONIUM SALT

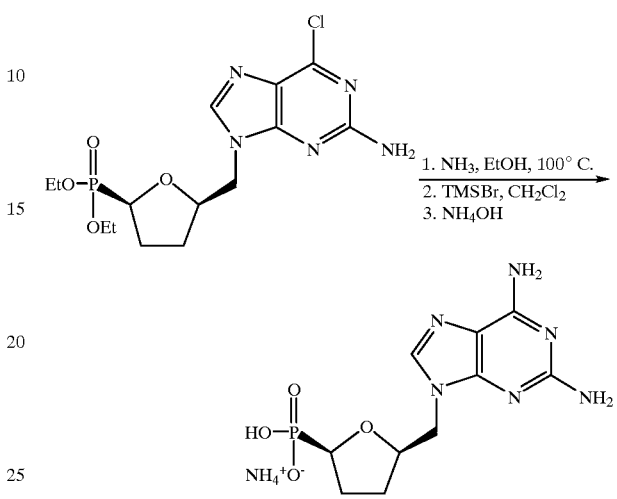

Prepared from (−)-(2R,5R)-5-(2'-amino-6'-chloropurin-9'-ylmethyl)-2-diethoxyphosphinoyl-tetrahydrofuran (example 107) as in example 110.

[α]$_D$ −39° (c 0.48, H$_2$O).

$^{13}$C NMR (75.5 MHz, D$_2$O) δ158.0, 155.4, 149.9, 141.5, 112.7, 79.9 (d, J=8.0 Hz), 77.2 (d, J=160.9 Hz), 48.7, 29.3 (d, J=7.7 Hz), 27.5 ppm.

Example 112

(+)-(2S,5S)-5-(2'-AMINOPURIN-9'-YlMETHYL)-2-DIETHOXYPHOSPHINOYL-TETRAHYDROFURAN

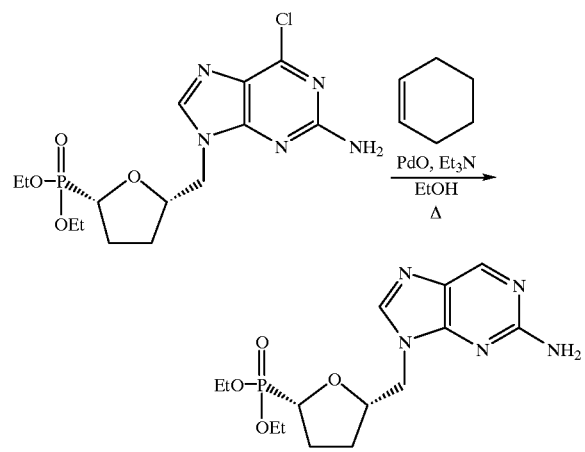

To a stirring solution of (+)-(2S,5S)-5-(2'-amino-6'-chloropurin-9'-ylmethyl)-2-diethoxyphosphinoyl-tetrahydrofuran (example 106) (193 mg, 0.50 mmol), palladium oxide (200 mg) and triethylamine (0.14 mL, 0.99 mmol) in dry ethyl alcohol (15 mL) was added at room temperature cyclohexene (2 mL). The mixture was refluxed for 2 hours and then allowed to cool down at room temperature. The mixture was filtered through CELITE deatomaceous earth and concentrated to dryness. The residue was purified by flash chromatography using 5 to 10% methanol in methylene chloride to give the title compound as an oil (138 mg, 78%).

$R_f$ 0.28 (10% MeOH/CH$_2$Cl$_2$). $[\alpha]_D$ +81° (c 1.27, CHCl$_3$).

$^1$H NMR (300 MHz, CDCl$_3$) δ: 8.56 (s, 1 H, H-6'), 7.94 (s, 1 H, H-8'), 5.31 (s, 2 H, NH$_2$), 4.35 (m, 1 H, H-5), 4.16 (dd, 1 H, J=3 HZ and 14 Hz, H-2), 4.10–4.00 (m, 6 H, H-6 and CH$_2$CH$_3$), 2.15 (m, 2 H, CH$_2$CH$_2$), 2.00 (m, 1 H, CH$_2$CH$_2$), 1.80 (m, 1 H, CH$_2$CH$_2$), 1.24 (t, 3 H, J=7 Hz, CH$_3$), 1.21 (t, 3 H, J=7 Hz, CH$_3$) ppm. UV $\lambda_{max}$ 307 nm, 244 nm (MeOH).

Example 113

(+)-(2S,5S)-5-(2'-AMINOPURIN-9'-YlMETHYL)-2-DIHYDROXYPHOSPHINOYL-TETRAHYDROFURAN, MONOAMMONIUM SALT

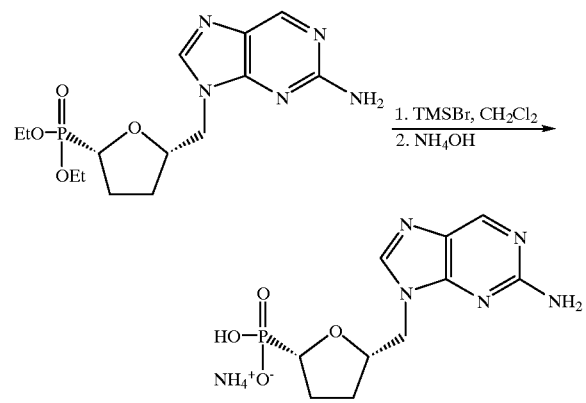

To a stirring solution of (+)-(2S,5S)-5-(2'-aminopurin-9'-ylmethyl)-2-diethoxyphosphinoyl-tetrahydrofuran (example 112) (95 mg, 0.27 mmol) in dry methylene chloride (5 mL) was added TMSBr (0.35 mL, 2.7 mmol). After stirring overnight at rt, the reaction mixture was concentrated to dryness and methanol (3×5 mL) was evaporated from the residue. The crude mixture was diluted in water (4 mL) and made basic with ammonium hydroxide. Lyophilization followed by purification on C$_{18}$ reverse phase HPLC eluting with 0 to 35% acetonitrile in 0.01 M ammonium acetate gave the title compound as a white solid (78 mg, 93%).

Mp 150° C. (dec.). $R_f$ 0.33 (7:2:1 i-PrOH/H$_2$O/NH$_4$OH).

$[\alpha]_D$ +65° (c 0.25, H$_2$O).

$^1$H NMR (300 MHz, D$_2$O) δ: 8.41 (s, 1 H, H-6'), 8.12 (s, 1 H, H-8'), 4.20–4.00 (m, 3 H, H-6, H-5), 3.76 (t, 1 H, J=8 Hz, H-2), 1.98 (m, 3 H, CH$_2$CH$_2$), 1.68 (m, 1 H, CH$_2$CH$_2$) ppm.

$^{13}$C NMR (75.5 MHz, D$_2$O) d: 160.1, 153.3, 149.4, 146.4, 127.4, 79.0 (d, J=8 Hz), 77.7 (d, 160 Hz), 47.7, 29.2 (d, 7 Hz), 27.6 ppm. UV $\lambda_{max}$ 303 nm, 242 nm (H$_2$O).

Example 114

(−)-(2R,5S)-5-(2'-AMINO-6'-CHLOROPURIN-9'-YlMETHYL)-2-DIETHOXYPHOSPHINOYL-TETRAHYDROFURAN

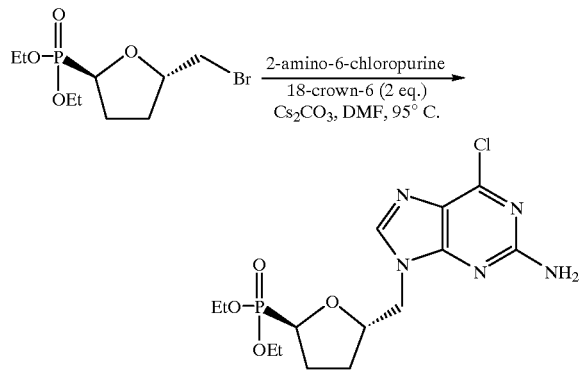

A mixture of (−)-(2R,5S)-5-bromomethyl-2-diethoxyphosphinoyl-tetrahydrofuran (example 104) (504 mg, 1.67 mmol), cesium carbonate (818 mg, 2.51 mmol), 18-crown-6 (885 mg, 3.35 mmol) and 2-amino-6-chloropurine (341 mg, 2.01 mmol) in dry DMF (6 mL) was stirred at 95° C. for 6 hours. The mixture was then cooled and filtered. Concentration of the filtrate gave a residue which was purified by chromatography eluting with 2 to 5% methanol in methylene chloride. The desired product was obtained as a foam (271 mg, 42%).

$R_f$ 0.31 (5% MeOH/CH$_2$Cl$_2$). $[\alpha]_D$ −30° (c 1.075, CHCl$_3$).

$^1$H NMR (300 MHz, CDCl$_3$) δ: 7.86 (s, 1 H, H-8'), 5.23 (s, 2 H, NH$_2$), 4.42 (m, 1 H, H-5), 4.25 (dd, 1 H, J=3 HZ and 14 Hz, H-2), 4.19–4.05 (m, 6 H, H=6, CH$_2$CH$_3$), 2.25–2.00 (m, 3 H, CH$_2$CH$_2$), 1.50 (m, 1 H, CH$_2$CH$_2$), 1.27 (t, 6 H, J=7 Hz, CH$_2$CH$_3$) ppm.

Example 115

(+)-(2S,5R)-5-(2'-AMINO-6'-CHLOROPURIN-9'-YlMETHYL)-2-DIETHOXYPHOSPHINOYL-TETRAHYDROFURAN

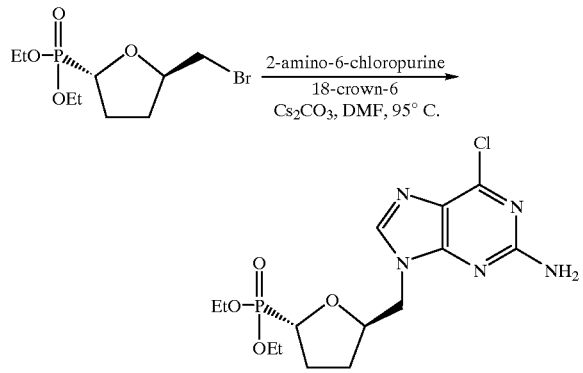

Prepared from (+)-(2S,5R)-5-bromomethyl-2-diethoxyphosphinoyl-tetrahydrofuran (example 105) as in example 114.

$[\alpha]_D$ +29° (c 1.025, CHCl$_3$).

Example 116

(−)-(2R,5S)-2-DIHYDROXYPHOSPHINOYL-5-(GUANIN-9'-YlMETHYL)-TETRAHYDROFURAN, MONOAMMONIUM SALT (BCH-1868)

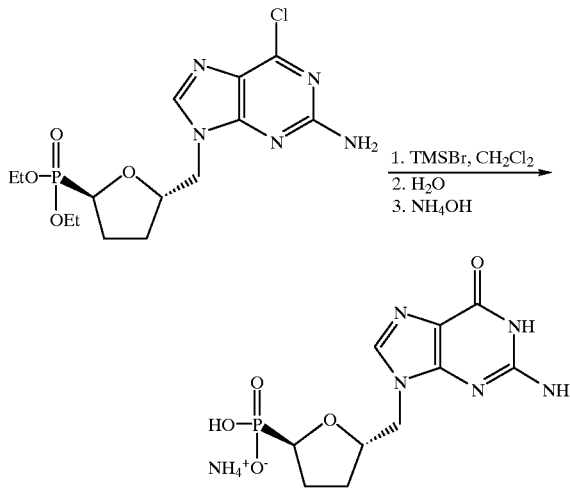

To a stirring solution of (−)-(2R,5S)-5-(2'-amino-6'-chloropurin-9'-ylmethyl)-2-diethoxyphosphinoyl-tetrahydrofuran (example 114) (168 mg, 0.43 mmol) in dry methylene chloride (3 mL) was added TMSBr (0.57 mL, 4.3 mmol). After stirring overnight at room temperature, the reaction mixture was concentrated to dryness and methanol (3×2 mL) was evaporated from the residue. The crude mixture was diluted in water (6 mL) and refluxed for 6 hours. The solution was made basic with ammonium hydroxide. Lyophilization followed by purification on $C_{18}$ reverse phase HPLC eluting with 0 to 15% acetonitrile in 0.01 M ammonium acetate gave the desired compound as a white solid (90.0 mg, 60%).

Mp >225° C. $R_f$ 0.24 (7:2:1 i-PrOH/$H_2O$/$NH_4OH$
$[\alpha]_D$ −9° (c 0.26, $H_2O$).
$^1$H NMR (300 MHz, $D_2O$) δ: 8.02 (s, 1 H, H-8'), 4.27 (m, 1 H, H-5), 4.80 (dd, 1 H, J=7.1 HZ and 14.6 Hz, H-6), 3.98 (dd, 1 H, J=3.3 HZ and 14.6 Hz, H-6), 3.88 (t, 1 H, J=7.6 Hz, H-2), 2.10–1.80 (m, 3 H), 1.50 (m, 1 H) ppm. UV $\lambda_{max}$ 252 nm, 270 nm ($H_2O$).

Example 117

(+)-(2S,5R)-2-DIHYDROXYPHOSPHINOYL-5-(GUANIN-9'-YlMETHYL)-TETRAHYDROFURAN, MONOAMMONIUM SALT (BCH-1867)

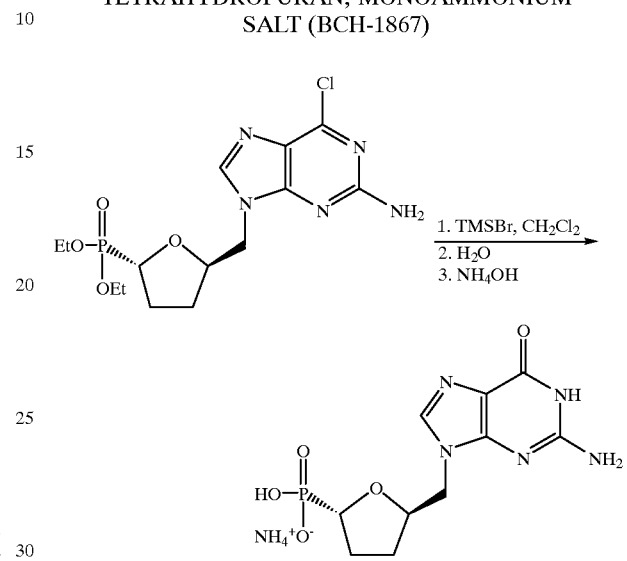

Prepared from (+)-(2S,5R)-5-(2'-amino-6'-chloropurin-9'-ylmethyl)-2-diethoxyphosphinoyl-tetrahydrofuran (example 115) as in example 116.

$[\alpha]_D$ +9° (c 0.25, $H_2O$).

Example 118

(−)-(2R,5S)-5-(2',6'-DIAMINOPURIN-9'-YlMETHYL)-2-DIHYDROXYPHOSPHINOYL-TETRAHYDROFURAN, MONOAMMONIUM SALT

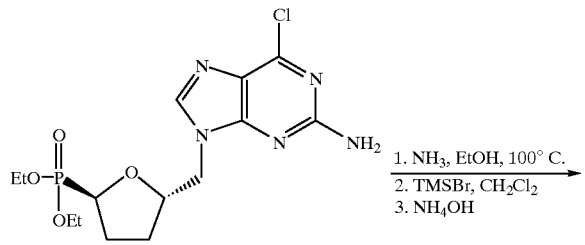

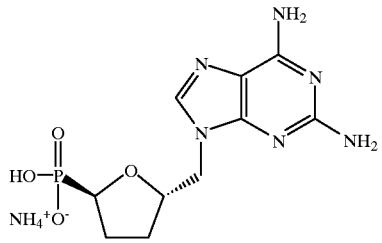

An ice-cold solution of (−)-(2R,5S)-5-(2'-amino-6'-chloropurin-9'-ylmethyl)-2-diethoxyphosphinoyl-tetrahydrofuran (example 114) (87 mg, 0.22 mmol) in ethanol (12 mL) was saturated with ammonia. The solution was then heated at 100° C. in a steel bomb for 16 hours. The bomb was cooled in ice and vented. Concentration of the solution gave a residue which was dissolved in dry methylene chloride (3 mL) and treated with TMSBr (0.30 mL, 2.23 mmol). After stirring for 16 h at rt, the mixture was concentrated to dryness and the residue was dissolved in water (5 mL). The solution was made basic with ammonium hydroxide and it was then washed with dichloromethane (2×5 mL) and hexane (5 mL). Lyophilization followed by purification on $C_{18}$ reverse phase HPLC eluting with 0 to 15% acetonitrile in 0.01 M ammonium acetate gave the desired compound as a white solid (35.5 mg, 48%).

Mp >225° C. $R_f$ 0.18 (7:2:1 i-PrOH/$H_2O$/$NH_4OH$
$[\alpha]_D$ −17° (c 0.26, $H_2O$).
$^1$H NMR (300 MHz, $D_2O$) δ: 7.73 (s, 1 H, H-8'), 4.26 (m, 1 H, H-5), 4.02 (dd, 1 H, J=3 HZ and 15 Hz, H-2), 3.93–3.88 (m, 2 H, H-6), 2.10–1.80 (m, 3 H), 1.54 (m, 1 H) ppm.
$^{13}$C NMR (75.5 MHz, $D_2O$) d: 156.4, 153.2, 151.3, 142.3, 111.9, 79.0 (d, J=6.6 Hz), 76.0 (d, J=162.3 Hz), 47.3, 29.4 (d, J=5.8 Hz), 27.8 ppm. UV $\lambda_{max}$ 254 and 282 nm ($H_2O$).

Example 119

(+)-(2S,5R)-5-(2',6'-DIAMINOPURIN-9'-YlMETHYL)-2-DIHYDROXYPHOSPHINOYL-TETRAHYDROFURAN, MONOAMMONIUM SALT

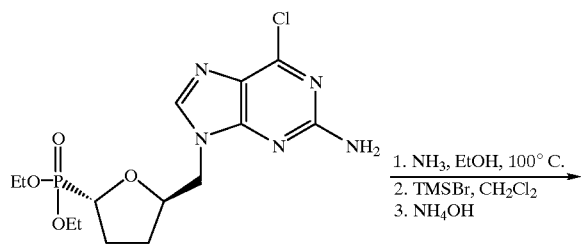

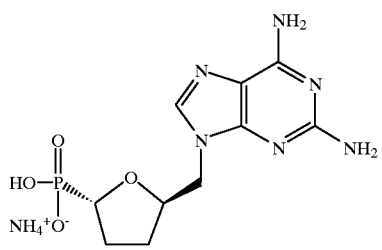

Prepared from (+)-(2S,5R)-5-(2'-amino-6'-chloropurin-9'-ylmethyl)-2-diethoxyphosphinoyl-tetrahydrofuran (example 115) as in example 118.
$[\alpha]_D$ +16° (c 0.25, $H_2O$).

Example 120

5-O-BENZOYL 3-O-(4-FLUOROPHENYL THIONOCARBONATE)-1,2-O-ISOPROPYLIDENE-D-XYLOFURANOSE

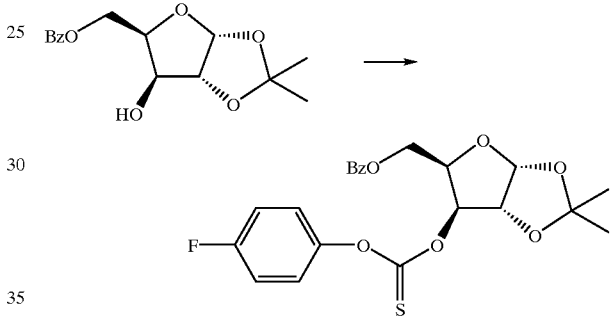

To a solution of 5-O-benzoyl 1,2-O-isopropylidene-D-xylofuranose (10.60 g, 36.05 mmol) and pyridine (11.7 mL, 144.2 mmol) in dichloromethane (180 mL) at 0° C. was added dropwise 4-fluorophenylchlorothionocarbonate (5.5 mL, 39.66 mmol). The solution was then allowed to proceed overnight at room temperature. The solution was then washed with saturated $NaHCO_3$, brine, dried ($MgSO_4$) and concentrated. Purification by chromatography eluting with 5–15% EtOAc in hexanes to give the desired compound (15.581 g, 96%).

$^1$H NMR (300 MHz, CDCl$_3$) δ: 8.06 (d, 2 H, ArH), 7.53 (t, 1 H, ArH), 7.43 (t, 2 H, ArH), 7.0 (m, 4 H, ArH), 6.05 (d, 1 H, H-1, J=3.8 Hz), 5.79 (d, 1 H, H-3, J=3.0 Hz), 4.78 (dd, 1 H, H-2, J=3.8 Hz), 4.74 (m, 1 H, H-4), 4.64 (m, 1 H, H-5$^{a,b}$), 1.55 (s, 3 H, CH$_3$), 1.35 (s, 3 H, CH$_3$).

Example 121

5-O-BENZOYL 3-DEOXY-1,2-O-ISOPROPYLIDENE-D-XYLOFURANOSE

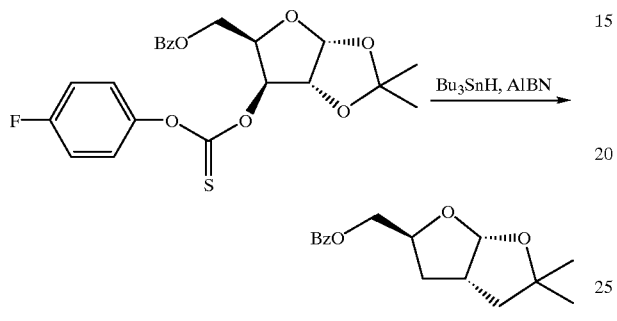

To a solution of 5-O-benzoyl 3-O-(4-fluorophenyl thionocarbonate)-1,2-O-isopropylidene-D-xylofuranose (example 120) (15.52 g, 34.60 mmol) and AIBN (1.135 g, 6.92 mmol) in toluene (346 mL) was added dropwise tributyltin hydride (14.0 mL, 52.0 mmol). The solution was then stirred at 80° C. for 3 h. The solvent was removed and the reaction mixture was purified by chromatography eluting with hexanes then with 10% EtOAc in hexanes to give the desired compound (8.5 g, 80%).

$[\alpha]_D$ -9.74 c 1.9 CHCl$_3$ $^1$H NMR (300 MHz, CDCl$_3$) δ: 8.05 (d, 2 H, ArH), 7.53 (t, 1 H, ArH), 7.44 (t, 2 H, ArH), 5.86 (d, 1 H, H-1, J=3.8 Hz), 4.76 (t, 1 H, H-2, J=4.4 Hz), 4.50 (m, 1 H, H-4, H-5$^a$), 4.36 (m, 1 H, H-5$^b$), 2.17 (dd, 1 H, H-3$^a$, J=4.2 and 13.2 Hz), 1.73 (m, 1 H, H-3$^b$), 1.52 (s, 3 H, CH$_3$), 1.31 (s, 3 H, CH$_3$).

Example 122

(2-METHOXYETHYL)-5-O-BENZOYL-3-DEOXY-D-XYLOFURANOSE

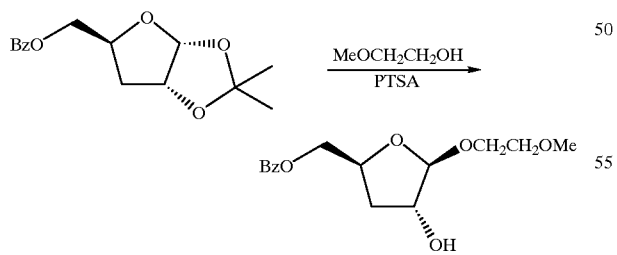

A solution of 5-O-benzoyl 3-deoxy-1,2-O-isopropylidene-D-xylofuranose (example 121) (8.5 g, 30.58 mmol) in 2-methoxy ethanol (100 mL) was stirred at 75° C. in the presence of PTSA (290 mg, 1.53 mmol) for 3 h. The solution was cooled to room temperature and Amberlite IRA-900 (OH$^-$) resin was added to neutralyze. The solution was filtered and the filtrate was concentrated to dryness.

Chromatography eluting with 50–75% ETOAc in hexanes gave the title compound (9.0 g, 97%)

$[\alpha]_D$ -28.4 c 1.24 CHCl$_3$ $^1$H NMR (300 MHz, CDCl$_3$) δ: 8.07 (d, 2 H, ArH), 7.55 (t, 1 H, ArH), 7.45 (t, 2 H, ArH), 4.99 (s, 1 H, H-1), 4.68 (m, 1 H, H-4), 4.3 (m, 3 H, H-2, H-5$^{a,b}$), 3.81 (dt, 1 H, OCHCH$_2$OMe), 3.57 (m, 1 H, OCHCH$_2$OMe), 3.45 (t, 2 H, OCHCCH$_2$OMe, J=4.7 Hz), 3.32 (s, 3 H, OCH$_3$), 2.05 (m, 2 H, H$^{3a,b}$), 1.94 (d, 1 H, OH, J=4.8 Hz).

Example 123

(2-METHOXYETHYL)-5-O-BENZOYL-2-O-t-BUTYLDIMETHYLSILYL-3-DEOXY-D-XYLOFURANOSE

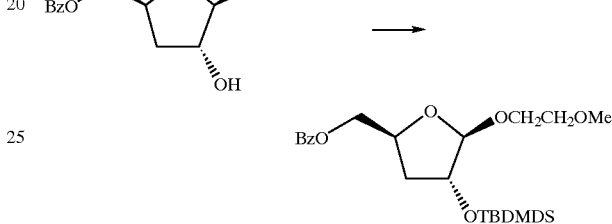

To a solution of (2-methoxyethyl)-5-O-benzoyl-3-deoxy-D-xylofuranose (example 122) (9.59 g, 32.40 mmol) and imidazole (3.980 g, 58.47 mmol) in DMF (40 mL) at room temperature was added t-butyldimethylsilyl chloride (6.35 g, 42.12 mmol). The solution was stirred for 3 h and saturated NaHCO$_3$ was added. The mixture was concentrated under vacuo. The residue was then partitioned between ether (100 mL) and water (50 mL). The aqueous phase was further extracted with ether (2×50 mL). The combined extracts were washed with brine (2×50 mL) dried (MgSO$_4$) and concentrated to give the title compound (13.3 g, 100%)

$[\alpha]_D$ -25.7 c 1.89 CHCl$_3$ $^1$H NMR (300 MHz, CDCl$_3$) δ: 8.07 (d, 2 H, ArH), 7.54 (t, 1 H, ArH), 7.44 (t, 2 H, ArH), 4.88 (s, 1 H, H-1), 4.67 (m, 1 H, H-4), 4.34 (m, 1 H, H-5$^a$, J=3.6 and 11.5 Hz), 4.30 (m, 2 H. H-5$^b$ and H-2), 3.79 (dt, 1 H, OCHCH$_2$OMe), 3.54 (m, 1 H, OCHCH$_2$OMe), 3.45 (m, 2 H, OCHCCH$_2$OMe), 3.32 (s, 3 H, OCH$_3$), 2.03 (m, 1 H, H$^{3a}$), 1.89 (m, 1 H, H-3$^b$), 0.87 (s, 9 H), 0.06 (s, 6 H).

Example 124

(2S,3R,5S)-5-BENZOYLOXYMETHYL-3-t-BUTYLDIMETHYLSILYLOXY-2-DIISOPROPYLOXYPHOSPHINOYL-TETRAHYDROFURAN

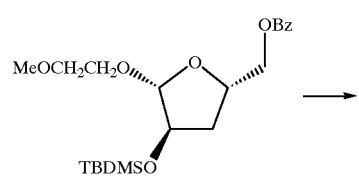

-continued

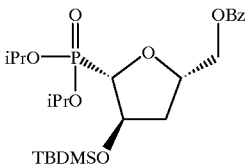

A 500 mL 3-neck flask fitted with a thermometer magnetic, stirrer and septa was charged with (2-methoxyethyl)-5-O-benzoyl-2-O-t-butyldimethylsilyl-3-deoxy-D-xylofuranose (example 123) (12.59 g, 30.71 mmol), triisopropylphosphite (9.85 mL, 39.92 mmol) and dichloromethane (300 mL). The solution was cooled in an ice-salt bath (internal temperature −10° C.). Titanium tetrachloride (3.,37 mL, 30.71 mmol) was then added dropwise. The temperature was maintained at −10° C. for 1 h and the reaction mixture was allowed to warm to room temperature and stirred overnight. The red solution was then poured into cold saturated NaHCO$_3$ (200 mL). The suspension was filtered through Celite washing with dichloromethane. The organic layer was collected and washed with brine dried (MgSO$_4$) and concentrated. Chromatography eluting with 25–40% EtOAc in hexanes gave the title compound (12.85 g, 84%)

[α]$_D$ −2.9 c 1.78 CHCl$_3$ $^1$H NMR (300 MHz, CDCl$_3$) δ: 8.01 (d, 2 H, ArH), 7.55 (t, 1 H, ArH), 7.42 (t, 2 H, ArH), 4.7 (m, 4 H), 4.44 (dd, 1 H, H-6$^a$, J 3.5 and 11.8 Hz), 4.34 (dd, 1 H, H-6$^b$, J=5.06 and 11.8 Hz), 4.15 (t, 1 H, H-2, J=4.4 Hz), 2.09 (m, 1 H, H$^{3a}$), 1.92 (m, 1 H, H-3$^b$), 1.34 (m, 12 H, 2 CH(CH$_3$)$_2$), 0.91 (s, 9 H), 0.10 (s, 6 H).

Example 125

(2S,3R,5S)-5-HYDROXYMETHYL-3-t-BUTYLDIMETHYLSILYLOXY-2-DIISOPROPYLOXYPHOSPHINOYL-TETRAHYDROFURAN

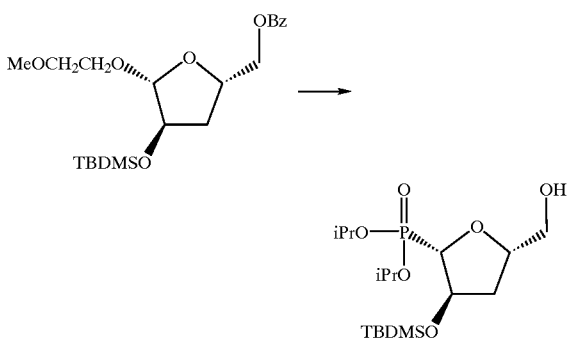

A solution of (2S,3R,5S)-5-benzoyloxymethyl-3-t-butyldimethylsilyloxy-2-diisopropyloxyphosphinoyl-tetrahydrofuran (example 124) (12.845 g, 25.69 mmol) in dry methanol 100 mL was stirred in the presence of anhydrous potassium carbonate (1.77 g, 12.85 mmol) for 3 h. The reaction mixture was neutralized with DOWEX (styrene-divinylbenzene copolymer ion-exchange resin) 50×8-400 (H$^+$) resin. Filtration followed by removal of the solvent under vacuo gave an oil which was chromatographed eluting with EtOAc then with 3% MeOH in EtOAc. The title compound was thus obtained as an oil. (6.161 g, 61%).

[α]$_D$ −5.5 c 1.47 CHCl$_3$ $^1$H NMR (300 MHz, CDCl$_3$) δ: 4.80 (m, 2 H, 2 CH(CH$_3$)$_2$), 4.68 (m, 1 H, H-3), 4.42 (m, 1 H, H-5), 4.10 (t, 1 H, H-2, J=4.6 Hz), 3.80 (dd, 1 H, H-6$^a$, J=3.0 and 12.1 Hz), 3.49 (dd, 1 H, H-6$^b$, J=4.4 and 12.0 Hz), 2.0 (br, 1H, OH), 1.91 (m, 2 H, H-4), 1.31 (d, 12 H, 2 CH(CH$_3$)$_2$, J=6.3 Hz), 0.90 (s, 9 H), 0.12 (s, 3 H), 0.09 (s, 3 H).

Example 126

(2S,3R,5S)-5-METHANESULFONYLOXYMETHYL-3-t-BUTYLDIMETHYLSILYLOXY-2-DIISOPROPYLOXYPHOSPHINOYL-TETRAHYDROFURAN

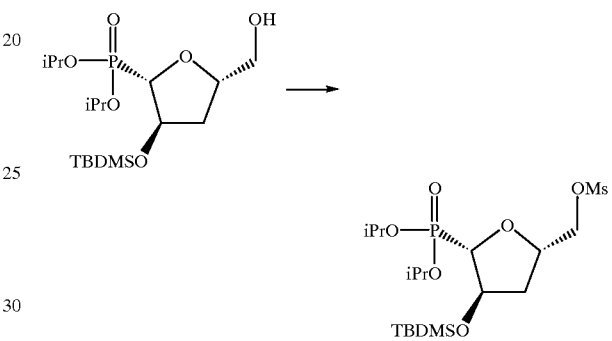

To a solution of (2S,3R,5S)-5-hydroxymethyl-3-t-butyldimethylsilyloxy-2-diisopropyloxyphosphinoyl-tetrahydrofuran (example 125) (700 mg, 1.768 mmol) and dry triethylamine (0.37 mL, 2.652 mmol) in dichloromethane (18 mL) at 0° C. was added methanesulfonyl chloride (0.18 mL, 2.298 mmol). After 1 h at 0° C., the solution was washed with saturated NaHCO$_3$, brine, dried (MgSO$_4$) and concentrated to dryness. The title compound was thus obtained as an oil (835 mg, 100%)

$^1$H NMR (300 MHz, CDCl$_3$) δ: 4.79 (m, 2 H, 2 CH(CH$_3$)$_2$), 4.70 (m, 1 H, H-3), 4.4 (m, 1 H, H-5), 4.35 (dd, 1 H, H-6$^a$, J=3.0 and 11.1 Hz), 4.23 (dd, 1 H, H-6$^b$, J=4.8 and 11.3 Hz), 4.10 (t, 1 H, H-2, J=4.7 Hz), 3.04 (s, 3 H, CH$_3$), 2.01 (m, 1 H, H-4$^a$), 1.90 (m, 1 H, H-4$^b$), 1.30 (d, 12 H, 2 CH(CH$_3$)$_2$, J=6.2 Hz), 0.91 (s, 9 H), 0.13 (s, 3 H), 0.10 (s, 3 H).

Example 127

(2S,3R,5S)-5-[2'-AMINO-6'-CHLOROPURIN-9'-YLMETHYL]-3-t-BUTYLDIMETHYLSILYLOXY-2-DIISOPROPYLOXYPHOSPHINOYL-TETRAHYDROFURAN

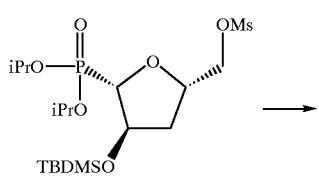

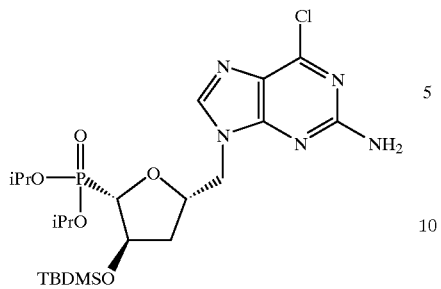

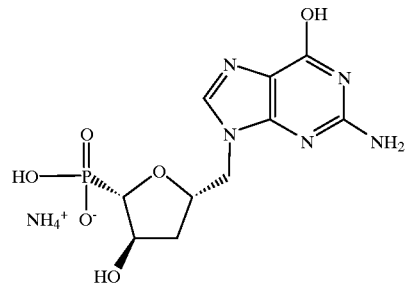

A suspension of 2-amino-6-chloropurine (716 mg, 4.22 mmol) and cesium carbonate (4.22 mmol) in dry DMF (10 mL) at 100° C. was stirred for 30 min. To that mixture was added dropwise a solution of (2S,3R,5S)-5-methanesulfonyloxymethyl-3-t-butyldimethylsilyloxy-2-diisopropyloxyphosphinoyl-tetrahydrofuran (example 126) (800 mg, 1.688 mmol) in DMF (10 mL). After stirring at 100° C. for 3 h, the reaction mixture was cooled to ambient temperature and the suspension was filtered through a CELITE diatomaceous earth. The filtrate was then concentrated to dryness and the residue was purified by chromatography eluting with 2–5% methanol in dichloromethane. The title compound was thus obtained as a white foam (550 mg, 60%).

$[\alpha]_D$ −43.3 c 0.60 CHCl$_3$ $^1$H NMR (300 MHz, CDCl$_3$) δ: 7.90 (s, 1 H, H-8'), 5.0 (br s, 2 H, NH$_2$), 4.7 (m, 3 H. 2 C$\underline{H}$(CH$_3$)$_2$ and H-3), 4.45 (m, 1 H, H-5), 4.32 (dd, 1 H, H-6$^a$, J=3.0 and 14.5 Hz), 4.18 (dd, 1 H, H-6$^b$, J=4.7 and 14.7 Hz), 3.99 (t, 1 H, H-2, J=4.5 Hz), 2.05 (m, 1 H, H-4$^a$), 1.55 (m, 1 H, H-4$^b$), 1.29 (m, 12 H, 2 CH(CH$_3$)$_2$), 0.87 (s, 9 H), 0.07 (s, 3 H), 0.04 (s, 3 H).

Example 128

(2S,3R,5S)-2-DIIHYDROXYPHOSPHINOYL-5-(GUANIN-9'-YLMETHYL)-3-HYDROXY-TETRAHYDROFURAN, MONOAMMONIUM SALT

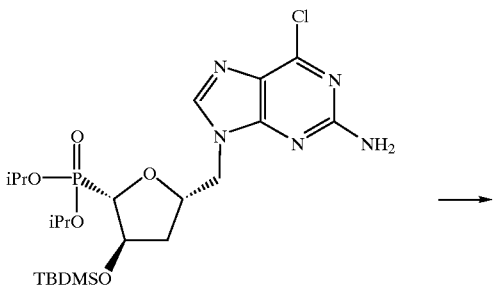

To a solution of (2S,3R,5S)-5-[2'-amino-6'-chloropurin-9'-ylmethyl]-3-t-butyldimethylsilyloxy-2-diisopropyloxyphosphinoyl-tetrahydrofuran (example 127) (175 mg, 0.32 mmol) in dichloromethane (5 mL) at room temperature was added TMSBr (0.84 ml, 6.393 mmol). The solution was stirred for 24 h and it was concentrated to dryness under vacuo. The residue was dissolved in 0.1 n HCl (10 ml) and refluxed for 6 h. The solution was neutralized with aqueous ammonia and purified by C$_{18}$ reverse phase HPLC eluting 0–35% acetonitrile in ammonium acetate (0.01 N) giving the title compound as a white solid.

$[\alpha]_D$ −15.8 c 0.33 H$_2$O $^1$H NMR (300 MHz, D$_2$O) δ: 7.73 (s, 1 H, H-8'), 4.48 (m,1 H, H-5), 4.39 (t, 1 H, H-3, J=3.3 Hz), 4.11 (dd, 1 H, H-6$^a$, J=3.0 and 14.8 Hz), 4.01 (dd, 1 H, H-6$^b$, J=6.1 and 14.8 Hz), 3.76 (dd, 1 H, H-2, J=2.9 and 6.6 Hz), 1.97 (m, H-4$^a$), 1.6 (m, H-4$^b$).

$^{13}$C NMR (75.5 MHz, D$_2$O) δ:159.4, 154.2, 141.3, 116.1, 79.5 (J$_{C-P}$=157.4 Hz), 77.6 (J$_{C-P}$=10.3 Hz), 73.1 (J$_{C-P}$=3.7 Hz), 46.8, 38.3 (J$_{C-P}$=7.9 Hz). UV λmax 251, 265 (sh).

Example 129

CIS AND TRANS 5-(t-BUTYLDIPHENYLSILYLOXYMETHYL)-2-(DIETHYLOXYPHOSPHINOYLMETHYL)-1,3-OXATHIOLANE

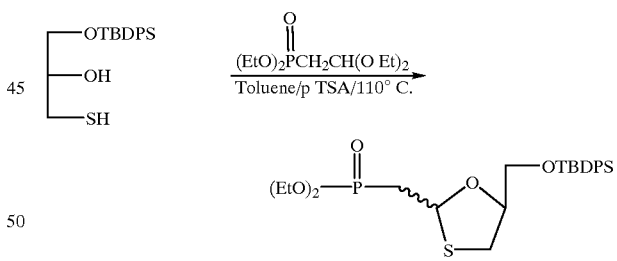

To a solution of diethylphosphonoacetaldehyde diethylacetal (12.23 g, 48.1 mmol, 1.2 eq.) and t-butyldiphenylsilyloxy-3-mercapto-2-propanol (13.63 g, 38.1 mmol, 1.2 eq.) in toluene (500 mL) was added pTSA (0.73 g, 3.8 mmol, 0.1 eq.). The mixture was stirred at reflux for 72 hr and was cooled to room temperature. A saturated solution of sodium bicarbonate was added and the aqueous phase was extracted with dichloromethane. The organic phase was dried with anhydrous magnesium sulphate and evaporated under reduced pressure. The crude material was purified by flash chromatography with ethyl acetate:hexane (2:1), and gave 16.31 g of the compound in a 87% yield.

$^1$H NMR (300 MHz, CDCl$_3$) δ: 7.64 (m, 4H, Ar—H), 7.38 (m, 6H, Ar—H), 5.43 (dd, 0.35H, J=12 Hz, J=6 Hz, H-2), 5.34 (dd, 0.65H, J=12 Hz, J=6 Hz, H-2), 4.39 (q, 0.35H, J=6 Hz, H-5), 4.09 (m, 4H, CH$_2$ and 0.65H, H-5), 3.86 (dd, 0.65H, J=11Hz, J=5 Hz, CH$_A$CH$_B$O), 3.75(dd, 0.65H, J=11 Hz, J=6 Hz, CH$_A$CH$_B$O), 3.72 (d, 0.35H, J=5 Hz, CH$_A$CH$_B$O), 3.71 (d, 0.35H, J=6 Hz, CH$_A$CH$_B$O), 3.09 (m, 1.35H, H-4), 2.92 (dd, 0.65H, J=10 Hz, J=9 Hz, H-4), 2.44 (m, 1H, CH$_2$P), 2.25 (m, 1H, CH$_2$P), 1.28 (m, 6H, CH$_3$), 1.03 (s, 9H, 3 t-butyl).

Example 130

CIS AND TRANS 2-(DIETHYLOXYPHOSPHINOYLMETHYL)-5-(HYDROXYMETHYL)-1,3-OXATHIOLANE

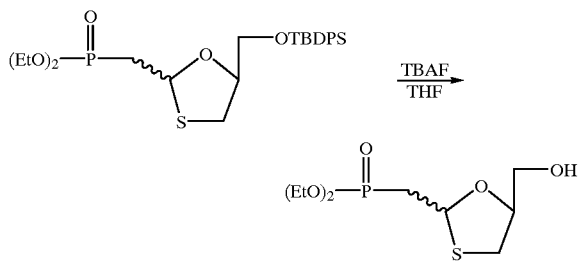

To a solution of cis and trans 5-(t-butyldiphenylsilyloxymethyl)-2-(diethyloxyphosphinoylmethyl)-1,3-oxathiolane (example 129) (15.68 g, 31.83 mmol) in THF (280 mL) was added tetrabutylammoniumfluoride (1 M solution in THF) (38.2 mL, 38.19 mmol, 1.2 eq.) at 0° C. The mixture was stirred at room temperature for 30 min. after which it was evaporated under reduced pressure. The residue was purified by flash chromatography with ethyl acetate: MeOH (95:5 to 93:7) to give 7.39 g of the compound in a 86% yield.

$^1$H NMR (300 MHz, CDCl$_3$) δ: 5.46 (m, 0.35H, H-2), 5.38 (m, 0.65H, H-2), 4.39 (q, 0.35H, J=6 Hz, H-5), 4.08 (m, 4H, CH$_2$ and 0.65H, H-5), 3.84 (dd, 0.65H, J=12 Hz, J=3 Hz, CH$_A$CH$_B$O), 3.66 (d, 0.7 H, J=5 Hz, CH$_2$O), 3.63 (dd, 0.65H, J=12 Hz, J=5 Hz, CH$_A$CH$_B$O), 3.29 (br, 1H, OH), 3.01 (m, 2H, H-4), 2.43 (m, 1H, CH$_A$CH$_B$P), 2.25 (m, 1H, CH$_A$CH$_B$P), 1.30 and 1.29 (2t, 6H, J=7 Hz, CH$_3$).

Example 131

2-BENZOYLOXYMETHYL-5-DIISOPROPOXYPHOSPHINOYL-1,3-OXATHIOLANE

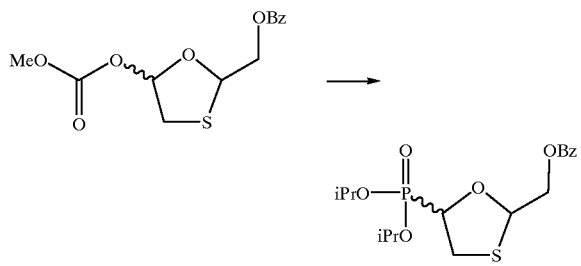

To a solution of 2-benzoyloxymethyl-5-(methyloxycarbonyloxy)-1,3-oxathiolane (4.80 g, 16.11 mmol) and triisopropyl phosphite (4.77 ml, 19.33 mmol) in dry dichloromethane (100 ml) at 0° C. was added dropwise titanium tetrachloride (1.77 ml, 16.11 mmol). After 2 h at 0° C., the reaction mixture was allowed to warm to room temperature and stirred overnight. The reaction mixture was then poured into saturated NaHCO$_3$ (100 ml). The mixture was then filtered and the filtrate was partitioned. The aqueous layer was further extracted with dichloromethane (2×) and the combined extracts were washed with brine (1×), dried and concentrated. Chromatography eluting with 25–50% EtAc in hexanes yielded the title compound as a 1:1 cis trans mixture (4.958 g, 79%).

$^1$H NMR (300 MHz, CDCl$_3$) δ: 8.05 (m, 2 H, ArH), 7.58 (m, 1 H, ArH), 7.40 (t, 2 H, ArH), 5.69 (dd, H-2), J=3.5 and 7.7 Hz), 5.54 (t, H-2, J=e5.3 Hz), 4.8 (m, 2 H, 2 CH(CH$_3$)$_2$), 4.6 (m, 2 H), 4.6 and 4.15 (m, 2 H), 3.27 (m, 2 H, H-4), 1.33 (m, 12 H, 2 CH(CH$_3$)$_2$.

Example 132

ANTIVIRAL ACTIVITY

Compounds were tested in vitro by the following methods:

HERPES SIMPLEX VIRUS PLAQUE REDUCTION ASSAY

Confluent monolayers of Vero cells in 24-well tissue culture dishes were inoculated with 100 μl of HSV-1 (KOS) or HSV-2 (186) diluted in 199 medium. After adsorption at 37° C. for one hour the monolayers were overlaid with medium containing test compound at several concentrations. Infected but otherwise untreated monolayers were included in the assay as virus controls. After incubation at 37° C. in 5% CO$_2$/air post-infection for 48 hours, the plates were fixed and stained with methanol-acetic acid (3:1) and carbol fuchsin. The monolayers were examined for the presence of plaques under a microscope. The percentage plaque reduction was determined for each compound and the 50% inhibitory concentration (IC$_{50}$) established.

The CD$_{50}$ value (cytotoxic dose at 50%) was assessed on virus-free control layers of cells to assess the toxicity of the compounds.

Results of the HSV assay are presented in Table 1:

TABLE 1

| Compounds | HSV-1 IC$_{50}$ (μg/ml) | HSV-2 IC$_{50}$ (μg/ml) | toxicity CD$_{50}$ (μg/ml) |
|---|---|---|---|
| CIS-2-DIHYDROXYPHOSPHINOYL-4-(GUANIN-9'-YLMETHYL)-1,3-DIOXOLANE (BCH-1299) (example 13) | 34 | >100 | 20 |
| CIS-2-(DIHYDROXYPHOSPHINOYL)-5-(GUANIN-9'-YLMETHYL)-1,3-OXATHIOLANE (BCH-1819) (example 32) | 8.0 | 99.0 | >100 |
| TRANS 2-DIHYDROXYPHOSPHINOYL-5-(GUANIN-9'-YLMETHYL)-1,3-OXATHIOLANE (BCH-1550) (example 29) | 32 | >100 | >100 |
| CIS-2-DIHYDROXYPHOSPHINOYL-5-(GUANIN-9'-YLMETHYL)-TETRAHYDROFURAN (BCH-1570) (example 72) | 44 | >100 | >100 |
| TRANS-2-DIHYDROXYPHOSPHINOYL-5-(GUANIN-9'-YLMETHYL)-TETRAHYDROFURAN (BCH-1573) (example 71) | 12.5 | 15 | >100 |

CYTOMEGALOVIRUS PLAQUE REDUCTION ASSAY

Subconfluent monolayers of Flow 2002 cells in 24 well tissue culture dishes were inoculated with 100 μl (containing 30 pfu) of CMV (WF1 strain) diluted in Glasgow's MEM. After adsorption at 37° C. (2 hours) the monolayers were overlaid with medium containing test compounds and 0.75% w/v carboxymethyl-cellulose. After incubation at 37° C. in 5% $CO_2$/air for 6–7 days the monolayers were fixed. Virus induced plaques were counted and the concentration of compound required to inhibit plaque formation by 50% compared to the untreated control cultures was calculated and expressed as the $PD_{50}$ value in micrograms per ml. $CD_{50}$ was assessed on virus-free cell layers.

Visual assessment of the integrity of the treated monolayers at each compound dose was made.

Results of the CMV assay are presented in Table 2:

TABLE 2

| Compounds | HCMV $PD_{50}$ (μg/ml) | toxicity $CD_{50}$ (μg/ml) |
|---|---|---|
| CIS-4-(GUANIN-9'-YLMETHYL)-2-(DIHYDROXY-PHOSPHINOYL)-1,3-DIOXOLANE (BCH-1299) (example 13) | 20 | >100 |
| CIS-2-DIHYDROXYPHOSPHINOYL-5-(GUANIN-9'-YLMETHYL)-TETRAHYDROFURAN (BCH-1570) (example 72) | 50 | >100 |
| TRANS-2-DIHYDROXYPHOSPHINOYL-5-(2',6'-DIAMINOPURIN-9'-YLMETHYL)-TETRAHYDROFURAN (BCH-1572) (example 73) | 65 | >100 |
| TRANS-2-(DIHYDROXYPHOSPHINOYL)-5-(THYMIN-3'-YLMETHYL)-1,3-OXATHIOLANE (BCH-1821) (example 34) | 6.0 | >100 |
| CIS-5-(ADENIN-9'-YLMETHYL)-2-(DIHYDROXYPHOSPHINOYL)-1,3-OXATHIOLANE (BCH-1831) (example 38) | 60 | >100 |
| CIS-2-(DIHYDROXYPHOSPHINOYLMETHYL)-4-(GUANIN-9'-YLMETHYL)-1,3-DIOXOLANE (BCH-1845) (example 86) | 0.1–1.0 | 100 |
| TRANS-2-(DIHYDROXYPHOSPHINOYL-METHYL)-4-(GUANIN-9'-YLMETHYL)-1,3-DIOXOLANE (BCH-1846) (example 86) | 1.2 | >100 |
| (+)-(2S,5S)-2-DIHYDROXYPHOSPHINOYL-5-(GUANIN-9'-Ylmethyl)-TETRAHYDROFURAN (BCH-1850) (example 108) | 0.5 | >100 |
| (+)-(2S,5R)-2-DIHYDROXYPHOSPHINOYL-5-(GUANIN-9'-Ylmethyl)-TETRAHYDROFURAN (BCH-1867) (example 117) | 15 | >100 |
| (−)-(2R,5S)-2-DIHYDROXYPHOSPHINOYL-5-(GUANIN-9'-Ylmethyl)-TETRAHYDROFURAN (BCH-1868) (example 116) | 15 | >100 |
| TRANS-4-(2',6'-DIAMINOPURIN-9'-YLMETHYL)-2-(DIHYDROXYPHOSPHINOYL-METHYL)-1,3-DIOXOLANE (BCH-2589) (example 87) | 8 | 100 |

What is claimed is:

1. A process for producing a compound of formula (I):

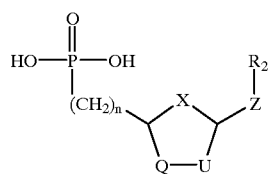

(I)

wherein
n is 0 or an integer,
X is O, S, $CH_2$, CH-halogen, CH—$N_3$ or C=$CH_2$;

Q is $CH_2$;

U is O or S;

Z is selected from: —O—, —O—$C_{1-6}$ alkylene, —S—$C_{1-6}$ alkylene, —NH—$C_{1-6}$ alkylene, —$(CH_2)_m$— wherein m is from 0 to 6, and —NH—$C_{1-6}$ wherein $R_c$ is hydrogen or a $C_{1-6}$ alkyl; and $R_2$ is a purine or pyrimidine nucleotide base or an analogue, wherein $R_2$ is selected from the group consisting of:

A)

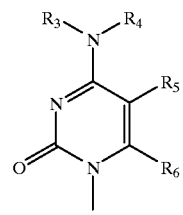

B)

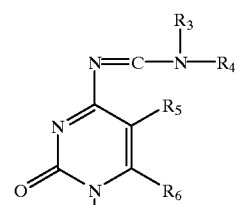

C)

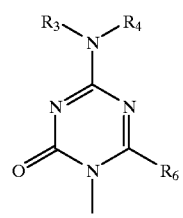

D)

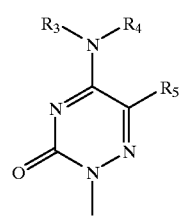

E)

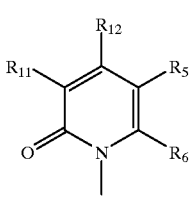

I)

-continued

J)
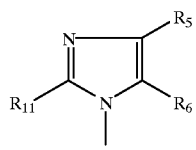

K)
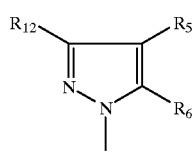

wherein:

x is oxygen or sulfur;

y is oxygen or sulfur;

$R_3$ and $R_4$ are independently selected from the group consisting of hydrogen, hydroxyl, amino, $C_{1-6}$ alkyl or $C_{2-6}$ alkenyl, $C_{2-6}$ alkynyl, $C_{1-10}$ carboxylic-acid-acyl, aryl or carboxyl;

$R_5$, $R_6$, $R_{11}$, and $R_{12}$ are each independently of the group consisting of hydrogen, halogen, hydroxyl, amino, cyano, carboxy, carbamoyl, alkoxycarbonyl, hydroxymethyl, trifluoromethyl, —S-aryl, $C_{1-6}$ alkyl, $C_{2-6}$ alkenyl substituted or unsubstituted with halogen or azido, $C_{2-6}$ alkynyl, $C_{1-10}$ carboxylic-acid-acyloxy, —S—COOH, —S-carbamoyl, carbamate, ureido, amidino, or aryloxy; and M)
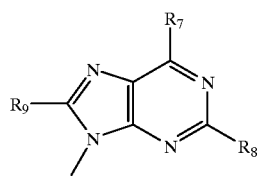

N)
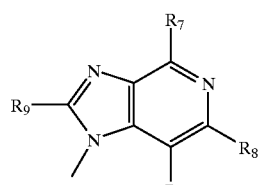

O)
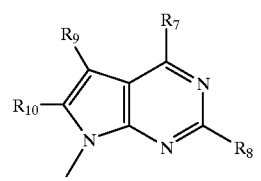

P)
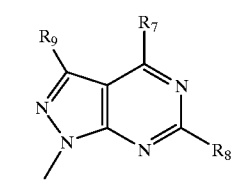

-continued

Q)
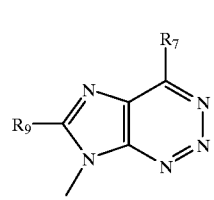

R)
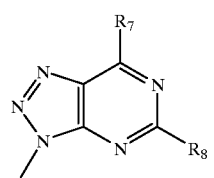

S)
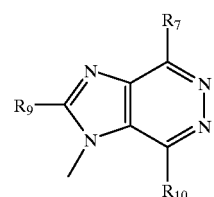

U)
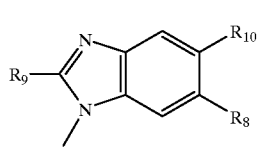

W)
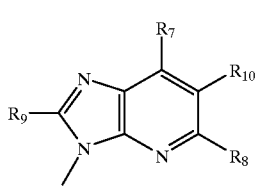

wherein;

$R_7$, $R_8$, $R_9$, and $R_{10}$ are each independently selected from the group consisting of hydrogen, hydroxy, alkoxy, thiol, —S-alkyl, amino, substituted amino, halogen, azido, cyano, carboxy, alkoxycarbonyl, carbamoyl, $C_{1-6}$ alkyl, $C_{2-6}$ alkenyl, or $C_{2-6}$ alkynyl, $C_{1-10}$ carboxylic-acid-acyloxy, aryl, aryloxy, —S—COOH, —S-carbamoyl, carbamate, ureido, amidino, and aryloxy, said process comprising:

a) coupling an intermediate of formula (IIf):

(II)
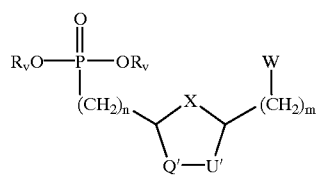

-continued

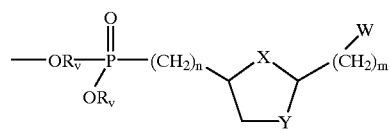
(IIf)

wherein n, m and X are as defined above;
Y is O or S;
$R_v$ is a hydroxy protecting group; and
W is a displaceable group or a hydroxy group;

with a purine or pyrimidine base, or analogue thereof as defined for $R_2$ above to yield an ester of formula (I), and b) optionally, converting said ester to obtain a phoshonate derivative of formula (I).

2. The process according to claim 1, wherein when either one of X or U is S, it may be oxidized to SO or $SO_2$.

3. The process according to claim 2, wherein $R_2$ is selected from the group consisting of:

A)

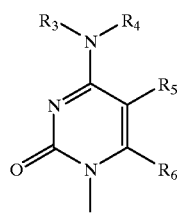

B)

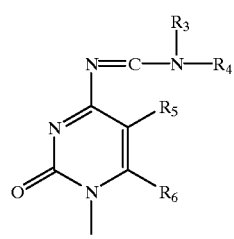

C)

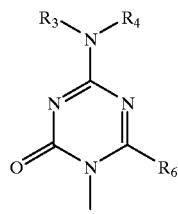

D)

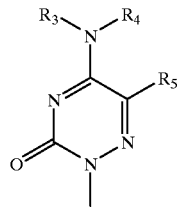

E)

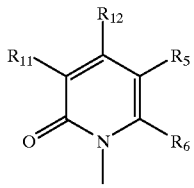

I)

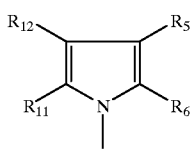

J)

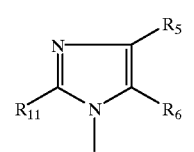

K)

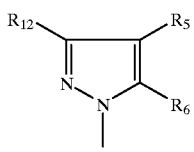

wherein:
x is oxygen or sulfur;
y is oxygen or sulfur;
$R_3$ and $R_4$ are independently selected from the group consisting of hydrogen, hydroxyl, amino, $C_{1-6}$ alkyl or $C_{2-6}$ alkenyl, $C_{2-6}$ alkynyl, $C_{1-10}$ carboxylic-acid-acyl, aryl or carboxyl;

$R_5$, $R_6$, $R_{11}$, and $R_{12}$ are each independently selected from the group consisting of hydrogen, halogen, hydroxyl, amino, cyano, carboxy, carbamoyl, alkoxycarbonyl, hydroxymethyl, trifluoromethyl, —S-aryl', $C_{1-6}$ alkyl, $C_{2-6}$ alkenyl substituted or unsubstituted with halogen or azido, $C_{2-6}$ alkynyl, $C_{1-10}$ carboxylic-acid-acyloxy, —S—COOH, —S-carbamoyl, carbamate, ureido, amidino, or aryloxy; and

M)

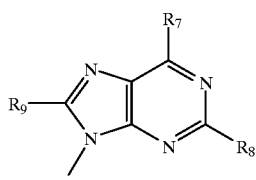

N)

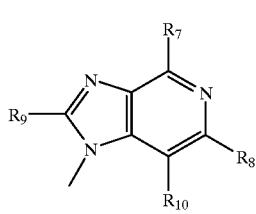

-continued

O) 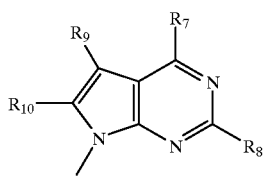

P) 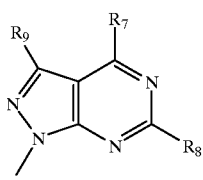

Q) 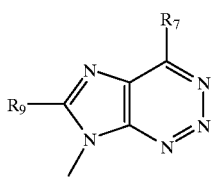

R) 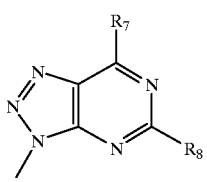

S) 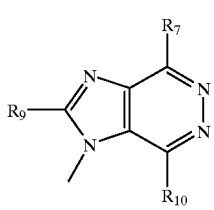

U) 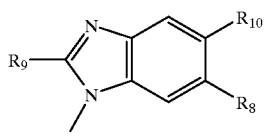

W) 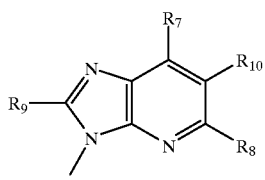

wherein:

$R_7$, $R_8$, $R_9$, and $R_{10}$ are each independently selected from the group consisting of hydrogen, hydroxy, alkoxy, thiol, —S-alkyl, amino, substituted amino, halogen, azido, cyano, carboxy, alkoxycarbonyl, carbamoyl, $C_{1-6}$ alkyl, $C_{2-6}$ alkenyl, or $C_{2-6}$ alkynyl, $C_{1-10}$ carboxylic-acid-acyloxy, aryl, aryloxy, —S—COOH, —S-carbamoyl, carbamate, ureido, amidino, and aryloxy.

4. The process according to claim 2, wherein n is 0 or an integer from 1 to 4.

5. The process according to claim 2, wherein Z is $(CH_2)_m$ or a $C_{1-6}$ alkoxy.

6. The process according to claim 2, wherein X is O, S, $CH_2$, CH-halogen, or OH—$N_3$.

7. The process according to claim 2, wherein n is 0 or 1.

8. The process according to claim 2, wherein X is O or S.

9. The process according to claim 2, wherein Z is $(CH_2)_m$ wherein m is 0 or 1.

10. The process according to claim 3, wherein R2 is selected from A), or M).

11. The process according to claim 3, wherein R2 is selected from: cytosine, adenine, guanine, uracil, thymine, 2-amino-6-chloropurine, 6-chloropurine, and 2,6-diaminopurine.

12. The process according to claim 1, wherein said displaceable group W is selected from: tosylate and halogen groups.

13. A process according to claim 1 wherein, when W is a hydroxy group, said coupling step is carried out under Mitsunobu reaction conditions.

14. The process according to claim 1, wherein said intermediate of formula (IIf) is made by coupling an intermediate of formula (IVb):

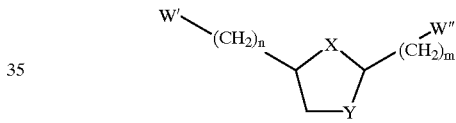

(IVb)

wherein W' and W" are each independently a hydroxy protecting group, a displaceable group, or an ester radical, —C(O)—OR, that can be modified to a displaceable group with a trialkyl phosphite or phosphonate salt.

15. The process according to claim 14, wherein said phosphorus-containing reagent is $PCl_3$ with $P(OR_v)_3$ wherein $R_v$ is a hydroxy protecting group, and the coupling is carried out under Michaelis-Arbuzov conditions with or without the presence of a Lewis acid.

16. The process according to claim 14, wherein said phosphorus-containing reagent is $O=P(OR_v)_2\ M^{\oplus\prime}$ wherein $R_v$ is a hydroxy protecting group and M is a metal, and the coupling is carried out under Michaelis-Becker conditions.

17. The process according to claim 15, wherein said Lewis acid, when present, is $TiCl_4$.

18. The process according to claim 17, wherein $R_v$ is $C_{1-6}$ alkyl or aryl.

19. The process according to claim 14, wherein W' is silyloxy, carboxylic-acid-acyloxy, ar-carboxylic-acid-acyloxy, mesyloxy, tosyloxy, or halogen.

20. The process according to claim 16, wherein $R_v$ is $C_{1-6}$ alkyl or aryl.

* * * * *